United States Patent
Ameil et al.

(10) Patent No.: US 10,702,391 B2
(45) Date of Patent: Jul. 7, 2020

(54) VERTEBRAL IMPLANT, DEVICE FOR VERTEBRAL ATTACHMENT OF THE IMPLANT AND INSTRUMENTATION FOR IMPLANTATION THEREOF

(71) Applicant: LDR Medical, Sainte-Savine (FR)

(72) Inventors: Marc Ameil, Reims (FR); Daniel D. Lee, Las Vegas, NV (US); Paul Henry Cho, Colleyville, TX (US)

(73) Assignee: LDR Medical, S.A.S., Sainte-Savine (FR)

( * ) Notice: Subject to any disclaimer, the term of this patent is extended or adjusted under 35 U.S.C. 154(b) by 639 days.

(21) Appl. No.: 15/309,197

(22) PCT Filed: May 6, 2015

(86) PCT No.: PCT/EP2015/060001
§ 371 (c)(1),
(2) Date: Nov. 6, 2016

(87) PCT Pub. No.: WO2015/169878
PCT Pub. Date: Nov. 12, 2015

(65) Prior Publication Data
US 2017/0056198 A1   Mar. 2, 2017

Related U.S. Application Data

(63) Continuation of application No. 14/638,746, filed on Mar. 4, 2015.

(30) Foreign Application Priority Data

May 6, 2014 (FR) ..................................... 14 54102

(51) Int. Cl.
*A61F 2/44* (2006.01)
*A61F 2/46* (2006.01)
(Continued)

(52) U.S. Cl.
CPC ............ *A61F 2/4425* (2013.01); *A61B 17/86* (2013.01); *A61B 17/8872* (2013.01); *A61F 2/44* (2013.01);
(Continued)

(58) Field of Classification Search
CPC ......................... A61F 2002/443; A61F 2/4425
See application file for complete search history.

(56) References Cited

U.S. PATENT DOCUMENTS

| 344,683 A | 6/1886 | Sherer |
|---|---|---|
| 1,025,596 A | 5/1912 | Strawser |

(Continued)

FOREIGN PATENT DOCUMENTS

| AU | 2015257671 A1 | 11/2016 |
|---|---|---|
| CA | 2946234 A1 | 11/2015 |

(Continued)

OTHER PUBLICATIONS

"U.S. Appl. No. 14/246,442, Final Office Action dated Mar. 6, 2017", 10 pgs.

(Continued)

*Primary Examiner* — Olivia C Chang
(74) *Attorney, Agent, or Firm* — Schwegman Lundberg & Woessner, P.A.

(57) ABSTRACT

The present invention relates to a vertebral implant, in particular for corpectomy, to a device for attaching a vertebral implant and to implantation instrumentation, the implant including at least one first body (2) and at least one second body (3) each having at least one face having shapes and dimensions mating those of at least one face of another body (3, 2) and forming mutual fitting means, in order to allow assembling of said bodies (2, 3) by sliding along a sliding axis and, on the other hand, at least one locking means (4) retained in at least one of the bodies (2, 3) and at (Continued)

least one abutment portion of which is laid out for passing from a so-called open position, allowing sliding for the assembling of said bodies (2, 3), to a so-called closed position, locking said bodies (2, 3) assembled together by the contact between at least said abutment portion and at least one abutment (42, 43) of at least one of said bodies (2, 3), said abutment (42, 43) being oriented not parallel to the sliding axis and said abutment portion passing from the open position to the closed position elastically by flexure or torsion.

19 Claims, 28 Drawing Sheets

(51) Int. Cl.
*A61B 17/86* (2006.01)
*A61B 17/88* (2006.01)
*A61F 2/30* (2006.01)

(52) U.S. Cl.
CPC .............. *A61F 2/442* (2013.01); *A61F 2/447* (2013.01); *A61F 2/4455* (2013.01); *A61F 2/4465* (2013.01); *A61F 2/4611* (2013.01); *A61F 2/4637* (2013.01); *A61F 2/4603* (2013.01); *A61F 2002/30387* (2013.01); *A61F 2002/30481* (2013.01); *A61F 2002/30505* (2013.01); *A61F 2002/30579* (2013.01); *A61F 2002/30593* (2013.01); *A61F 2002/30604* (2013.01); *A61F 2002/30841* (2013.01); *A61F 2002/448* (2013.01); *A61F 2002/4629* (2013.01); *A61F 2220/0016* (2013.01)

(56) References Cited

U.S. PATENT DOCUMENTS

| | | | |
|---|---|---|---|
| 1,121,484 A | 12/1914 | Crites | |
| 3,875,595 A | 4/1975 | Froning | |
| 3,948,262 A | 4/1976 | Zaffaroni | |
| 4,135,506 A | 1/1979 | Ulrich | |
| 4,349,921 A | 9/1982 | Kuntz | |
| 4,507,115 A | 3/1985 | Kambara et al. | |
| 4,790,303 A | 12/1988 | Stefee | |
| 4,834,757 A | 5/1989 | Brantigan | |
| 4,863,476 A | 9/1989 | Shepperd | |
| 4,892,545 A | 1/1990 | Day et al. | |
| 4,904,261 A | 2/1990 | Dove et al. | |
| 5,108,442 A * | 4/1992 | Smith ................... A61F 2/389 |
| | | | 623/20.33 |
| 5,326,205 A | 7/1994 | Anspach, Jr. et al. | |
| 5,443,514 A | 8/1995 | Steffee | |
| 5,501,695 A | 3/1996 | Anspach, Jr. et al. | |
| 5,522,899 A | 6/1996 | Michelson | |
| 5,571,109 A | 11/1996 | Bertagnoli | |
| 5,609,635 A | 3/1997 | Michelson | |
| 5,658,335 A | 8/1997 | Allen | |
| 5,683,394 A | 11/1997 | Rinner | |
| 5,776,199 A | 7/1998 | Michelson | |
| 5,800,547 A | 9/1998 | Schafer et al. | |
| 5,810,820 A | 9/1998 | Santori et al. | |
| 5,849,004 A | 12/1998 | Bramlet | |
| 5,888,228 A | 3/1999 | Knothe et al. | |
| 5,976,139 A | 11/1999 | Bramlet | |
| 6,066,175 A | 5/2000 | Henderson et al. | |
| 6,099,531 A | 8/2000 | Bonutti | |
| 6,102,950 A | 8/2000 | Vaccaro | |
| 6,113,638 A | 9/2000 | Williams et al. | |
| 6,143,032 A | 11/2000 | Schafer et al. | |
| 6,174,311 B1 | 1/2001 | Branch et al. | |
| 6,179,873 B1 | 1/2001 | Zientek | |
| 6,183,474 B1 | 2/2001 | Bramlet et al. | |
| 6,206,923 B1 | 3/2001 | Boyd et al. | |
| 6,210,442 B1 | 4/2001 | Wing et al. | |
| 6,231,610 B1 | 5/2001 | Geisler | |
| 6,258,089 B1 | 7/2001 | Campbell et al. | |
| 6,267,764 B1 | 7/2001 | Elberg | |
| 6,302,914 B1 | 10/2001 | Michelson | |
| 6,342,074 B1 | 1/2002 | Simpson | |
| 6,371,987 B1 | 4/2002 | Weiland et al. | |
| 6,383,186 B1 | 5/2002 | Michelson | |
| 6,419,703 B1 | 7/2002 | Fallin et al. | |
| 6,419,706 B1 | 7/2002 | Graf | |
| 6,423,063 B1 | 7/2002 | Bonutti | |
| 6,447,544 B1 | 9/2002 | Michelson | |
| 6,447,546 B1 | 9/2002 | Bramlet et al. | |
| 6,447,547 B1 | 9/2002 | Michelson | |
| 6,471,724 B2 | 10/2002 | Zdeblick et al. | |
| 6,478,823 B1 | 11/2002 | Michelson | |
| 6,485,517 B1 | 11/2002 | Michelson | |
| 6,500,205 B1 | 12/2002 | Michelson | |
| 6,527,803 B1 | 3/2003 | Crozet et al. | |
| 6,540,753 B2 | 4/2003 | Cohen | |
| 6,558,423 B1 | 5/2003 | Michelson | |
| 6,558,424 B2 | 5/2003 | Thalgott | |
| 6,565,605 B2 | 5/2003 | Goble et al. | |
| 6,607,530 B1 | 8/2003 | Carl et al. | |
| 6,610,065 B1 | 8/2003 | Branch et al. | |
| 6,620,163 B1 | 9/2003 | Michelson | |
| 6,648,893 B2 | 11/2003 | Dudasik | |
| 6,695,846 B2 | 2/2004 | Richelsoph et al. | |
| 6,706,067 B2 | 3/2004 | Shimp et al. | |
| 6,709,458 B2 | 3/2004 | Michelson | |
| 6,712,818 B1 | 3/2004 | Michelson | |
| 6,716,247 B2 | 4/2004 | Michelson | |
| 6,723,128 B2 | 4/2004 | Uk | |
| 6,733,535 B2 | 5/2004 | Michelson | |
| 6,749,636 B2 | 6/2004 | Michelson | |
| 6,767,367 B1 | 7/2004 | Michelson | |
| 6,770,096 B2 | 8/2004 | Bolger et al. | |
| 6,793,679 B2 | 9/2004 | Michelson | |
| 6,805,714 B2 | 10/2004 | Sutcliffe | |
| 6,808,537 B2 | 10/2004 | Michelson | |
| 6,835,206 B2 | 12/2004 | Jackson | |
| 6,849,093 B2 | 2/2005 | Michelson | |
| 6,890,355 B2 | 5/2005 | Michelson | |
| 6,902,580 B2 | 6/2005 | Fallin et al. | |
| 6,923,811 B1 | 8/2005 | Carl et al. | |
| 6,923,830 B2 | 8/2005 | Michelson | |
| 6,955,691 B2 | 10/2005 | Chae et al. | |
| 6,962,606 B2 | 11/2005 | Michelson | |
| 6,972,019 B2 | 12/2005 | Michelson | |
| 6,972,035 B2 | 12/2005 | Michelson | |
| 6,981,975 B2 | 1/2006 | Michelson | |
| 6,984,234 B2 | 1/2006 | Bray | |
| 6,994,727 B2 | 2/2006 | Khandkar et al. | |
| 7,001,385 B2 | 2/2006 | Bonutti | |
| 7,008,453 B1 | 3/2006 | Michelson | |
| 7,033,394 B2 | 4/2006 | Michelson | |
| 7,041,135 B2 | 5/2006 | Michelson | |
| 7,041,136 B2 | 5/2006 | Goble et al. | |
| 7,051,610 B2 | 5/2006 | Stoianovici et al. | |
| 7,060,097 B2 | 6/2006 | Fraser et al. | |
| 7,063,701 B2 | 6/2006 | Michelson | |
| 7,063,702 B2 | 6/2006 | Michelson | |
| 7,066,961 B2 | 6/2006 | Michelson | |
| 7,074,237 B2 | 7/2006 | Goble et al. | |
| 7,090,698 B2 | 8/2006 | Goble et al. | |
| 7,094,239 B1 | 8/2006 | Michelson | |
| 7,112,206 B2 | 9/2006 | Michelson | |
| 7,118,579 B2 | 10/2006 | Michelson | |
| 7,118,598 B2 | 10/2006 | Michelson | |
| 7,128,760 B2 | 10/2006 | Michelson | |
| 7,128,761 B2 | 10/2006 | Kuras et al. | |
| 7,137,984 B2 | 11/2006 | Michelson | |
| 7,153,325 B2 | 12/2006 | Kim et al. | |
| 7,163,561 B2 | 1/2007 | Michelson | |
| 7,211,112 B2 | 5/2007 | Baynham et al. | |
| 7,217,291 B2 | 5/2007 | Zucherman et al. | |
| 7,217,293 B2 | 5/2007 | Branch | |
| 7,223,289 B2 | 5/2007 | Trieu et al. | |
| 7,232,463 B2 | 6/2007 | Falahee | |

(56) References Cited

U.S. PATENT DOCUMENTS

| | | |
|---|---|---|
| 7,232,464 B2 | 6/2007 | Mathieu |
| 7,235,082 B2 | 6/2007 | Bartish et al. |
| 7,238,205 B2 | 7/2007 | Karahalios |
| 7,255,698 B2 | 8/2007 | Michelson |
| 7,303,583 B1 | 12/2007 | Schär et al. |
| 7,326,248 B2 | 2/2008 | Michelson |
| 7,361,196 B2 | 4/2008 | Fallin et al. |
| 7,410,501 B2 | 8/2008 | Michelson |
| 7,431,735 B2 | 10/2008 | Liu et al. |
| 7,435,262 B2 | 10/2008 | Michelson |
| 7,442,209 B2 | 10/2008 | Michelson |
| 7,445,636 B2 | 10/2008 | Liu et al. |
| 7,445,635 B2 | 11/2008 | Fallin et al. |
| 7,455,684 B2 | 11/2008 | Gradel et al. |
| 7,455,692 B2 | 11/2008 | Michelson |
| 7,465,317 B2 | 12/2008 | Malberg et al. |
| 7,473,276 B2 | 1/2009 | Aebi et al. |
| 7,503,933 B2 | 3/2009 | Michelson |
| 7,540,882 B2 | 6/2009 | Michelson |
| 7,563,284 B2 | 7/2009 | Coppes et al. |
| 7,563,286 B2 | 7/2009 | Gerber et al. |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,604,654 B2 | 10/2009 | Fallin et al. |
| 7,608,107 B2 | 10/2009 | Michelson |
| 7,611,538 B2 | 11/2009 | Belliard et al. |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,625,393 B2 | 12/2009 | Fallin et al. |
| 7,637,951 B2 | 12/2009 | Michelson |
| 7,637,953 B2 | 12/2009 | Branch et al. |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,727,280 B2 | 6/2010 | McLuen |
| 7,744,602 B2 | 6/2010 | Teeny et al. |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,188 B2 | 12/2010 | Moskowitz et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,080,062 B2 | 12/2011 | Armstrong et al. |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | McLuen |
| 8,216,312 B2 | 7/2012 | Gray |
| 8,257,443 B2 | 9/2012 | Kamran et al. |
| 8,267,999 B2 | 9/2012 | Beaurain et al. |
| 8,303,663 B2 | 11/2012 | Jimenez et al. |
| 8,313,528 B1 | 11/2012 | Wensel |
| 8,323,345 B2 | 12/2012 | Sledge |
| 8,343,197 B2 | 1/2013 | Gonzalez-Hernandez |
| 8,343,219 B2 | 1/2013 | Allain et al. |
| 8,349,015 B2 | 1/2013 | Bae et al. |
| 8,460,388 B2 | 6/2013 | Kirwan et al. |
| 8,535,352 B2 | 9/2013 | Altarac et al. |
| 8,545,563 B2 | 10/2013 | Brun et al. |
| 8,617,245 B2 | 12/2013 | Brett |
| 8,696,681 B2 | 4/2014 | Harris et al. |
| 8,979,932 B2 | 3/2015 | Rashbaum et al. |
| 9,039,774 B2 | 5/2015 | Chataigner et al. |
| 9,044,337 B2 | 6/2015 | Dinville et al. |
| 9,078,765 B2 | 7/2015 | Louis et al. |
| 9,125,750 B2 * | 9/2015 | Farris ..................... A61F 2/442 |
| 2002/0016592 A1 | 2/2002 | Branch et al. |
| 2002/0026243 A1 | 2/2002 | Lin |
| 2002/0040243 A1 | 4/2002 | Attali et al. |
| 2002/0059938 A1 | 5/2002 | Fogarty et al. |
| 2002/0070565 A1 | 6/2002 | Szapucki et al. |
| 2002/0161444 A1 | 10/2002 | Choi |
| 2002/0165613 A1 | 11/2002 | Lin et al. |
| 2002/0193880 A1 | 12/2002 | Fraser |
| 2003/0069640 A1 | 4/2003 | Ferreira et al. |
| 2003/0074075 A1 | 4/2003 | James, Jr. et al. |
| 2003/0135279 A1 | 7/2003 | Michelson |
| 2003/0149484 A1 | 8/2003 | Michelson |
| 2003/0187436 A1 | 10/2003 | Bolger et al. |
| 2003/0191531 A1 | 10/2003 | Berry et al. |
| 2003/0195514 A1 | 10/2003 | Trieu et al. |
| 2004/0010312 A1 | 1/2004 | Enayati |
| 2004/0030387 A1 | 2/2004 | Landry et al. |

(56) References Cited

U.S. PATENT DOCUMENTS

| | | |
|---|---|---|
| 2004/0073307 A1 | 4/2004 | Keller |
| 2004/0073313 A1 | 4/2004 | Link et al. |
| 2004/0117022 A1 | 6/2004 | Marnay et al. |
| 2004/0199254 A1 | 10/2004 | Louis et al. |
| 2004/0210219 A1 | 10/2004 | Bray |
| 2004/0210227 A1 | 10/2004 | Trail et al. |
| 2004/0210313 A1 | 10/2004 | Michelson |
| 2004/0243238 A1 | 12/2004 | Arnin et al. |
| 2004/0243240 A1 | 12/2004 | Beaurain et al. |
| 2004/0254643 A1 | 12/2004 | Jackson |
| 2005/0015149 A1 | 1/2005 | Michelson |
| 2005/0027359 A1 | 2/2005 | Mashburn |
| 2005/0027362 A1 | 2/2005 | Williams et al. |
| 2005/0038512 A1 | 2/2005 | Michelson |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0085917 A1 | 4/2005 | Marnay et al. |
| 2005/0096745 A1 | 5/2005 | Andre et al. |
| 2005/0143733 A1 | 6/2005 | Petit |
| 2005/0143825 A1 | 6/2005 | Enayati |
| 2005/0149189 A1 | 7/2005 | Mokhtar et al. |
| 2005/0159814 A1 | 7/2005 | Karahalios |
| 2005/0177236 A1 | 8/2005 | Mathieu et al. |
| 2005/0209697 A1 | 9/2005 | Paponneau et al. |
| 2005/0283236 A1 | 12/2005 | Razian |
| 2005/0288788 A1 | 12/2005 | Dougherty-shah |
| 2006/0058878 A1 | 3/2006 | Michelson |
| 2006/0069437 A1 | 3/2006 | Weber |
| 2006/0085071 A1 | 4/2006 | Lechmann et al. |
| 2006/0085076 A1 | 4/2006 | Krishna et al. |
| 2006/0089717 A1 | 4/2006 | Krishna et al. |
| 2006/0095136 A1 | 5/2006 | McLuen |
| 2006/0121084 A1 | 6/2006 | Borden et al. |
| 2006/0122703 A1 | 6/2006 | Aebi et al. |
| 2006/0129244 A1 | 6/2006 | Ensign |
| 2006/0142863 A1 | 6/2006 | Fraser et al. |
| 2006/0155377 A1 | 7/2006 | Beaurain et al. |
| 2006/0206208 A1 | 9/2006 | Michelson |
| 2006/0235426 A1 | 10/2006 | Lim et al. |
| 2006/0241621 A1 | 10/2006 | Moskowitz et al. |
| 2006/0241761 A1 | 10/2006 | Gately |
| 2006/0241764 A1 | 10/2006 | Michelson |
| 2006/0253201 A1 | 11/2006 | McLuen |
| 2006/0276899 A1 | 12/2006 | Zipnick et al. |
| 2007/0016297 A1 | 1/2007 | Johnson |
| 2007/0032871 A1 | 2/2007 | Michelson |
| 2007/0049943 A1 | 3/2007 | Moskowitz et al. |
| 2007/0073404 A1 | 3/2007 | Rashbaum et al. |
| 2007/0093850 A1 | 4/2007 | Harris et al. |
| 2007/0106388 A1 | 5/2007 | Michelson |
| 2007/0142843 A1 | 6/2007 | Dye |
| 2007/0162128 A1 | 7/2007 | DeRidder et al. |
| 2007/0179623 A1 | 8/2007 | Trieu et al. |
| 2007/0208345 A1 | 9/2007 | Marnay et al. |
| 2007/0233253 A1 | 10/2007 | Bray et al. |
| 2007/0250167 A1 | 10/2007 | Bray et al. |
| 2007/0260249 A1 | 11/2007 | Boyajian et al. |
| 2007/0270954 A1 | 11/2007 | Wu |
| 2007/0270960 A1 | 11/2007 | Bonin, Jr. et al. |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0027547 A1 | 1/2008 | Yu et al. |
| 2008/0027550 A1 | 1/2008 | Link et al. |
| 2008/0033432 A1 | 2/2008 | McGraw et al. |
| 2008/0033562 A1 | 2/2008 | Krishna et al. |
| 2008/0132949 A1 | 6/2008 | Aferzon et al. |
| 2008/0177306 A1 | 7/2008 | Lamborne et al. |
| 2008/0195211 A1 | 8/2008 | Lin et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0054988 A1 | 2/2009 | Hess |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112271 A1 | 4/2009 | Moskowitz et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0138086 A1 | 5/2009 | Dewey |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216331 A1 | 8/2009 | Grotz et al. |
| 2009/0222092 A1 | 9/2009 | Davis et al. |
| 2009/0222100 A1 | 9/2009 | Cipoletti et al. |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0016903 A1 | 1/2010 | Matityahu et al. |
| 2010/0016974 A1 | 1/2010 | Janowski et al. |
| 2010/0049259 A1 | 2/2010 | Lambrecht et al. |
| 2010/0050276 A1 | 2/2010 | Depaepe |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0125334 A1 | 5/2010 | Krueger |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0298941 A1 | 11/2010 | Hes et al. |
| 2010/0305700 A1 | 12/2010 | Ben-arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |

(56) References Cited

U.S. PATENT DOCUMENTS

| | | | |
|---|---|---|---|
| 2011/0112587 A1 | 5/2011 | Patel et al. | |
| 2011/0118843 A1 | 5/2011 | Mathieu et al. | |
| 2011/0125267 A1 | 5/2011 | Michelson | |
| 2011/0137420 A1 | 6/2011 | Michelson | |
| 2011/0144703 A1 | 6/2011 | Krause et al. | |
| 2011/0160860 A1 | 6/2011 | Johnston et al. | |
| 2011/0166655 A1 | 7/2011 | Michelson | |
| 2011/0166656 A1 | 7/2011 | Thalgott et al. | |
| 2011/0166657 A1 | 7/2011 | Thalgott et al. | |
| 2011/0166658 A1 | 7/2011 | Garber et al. | |
| 2011/0172774 A1 | 7/2011 | Varela | |
| 2011/0178599 A1 | 7/2011 | Brett | |
| 2011/0196492 A1 | 8/2011 | Lambrecht et al. | |
| 2011/0196493 A1 | 8/2011 | Pimenta | |
| 2011/0196494 A1 | 8/2011 | Yedlicka et al. | |
| 2011/0202136 A1 | 8/2011 | Brittan et al. | |
| 2011/0208311 A1 | 8/2011 | Janowski | |
| 2011/0208313 A1 | 8/2011 | Michelson | |
| 2011/0230969 A1 | 9/2011 | Biedermann et al. | |
| 2011/0230971 A1 | 9/2011 | Donner et al. | |
| 2011/0264227 A1 | 10/2011 | Boyajian et al. | |
| 2011/0295371 A1 | 12/2011 | Moskowitz et al. | |
| 2011/0301713 A1 | 12/2011 | Theofilos | |
| 2011/0301714 A1 | 12/2011 | Theofilos | |
| 2011/0313528 A1 | 12/2011 | Laubert et al. | |
| 2012/0022654 A1 | 1/2012 | Farris et al. | |
| 2012/0078371 A1 | 3/2012 | Gamache et al. | |
| 2012/0191196 A1 | 7/2012 | Louis et al. | |
| 2012/0197403 A1 | 8/2012 | Merves | |
| 2012/0197404 A1 | 8/2012 | Brun et al. | |
| 2012/0265259 A1 | 10/2012 | Laposta et al. | |
| 2013/0085573 A1* | 4/2013 | Lemoine | A61F 2/4465 623/17.16 |
| 2013/0123926 A1 | 5/2013 | Bae et al. | |
| 2013/0150968 A1 | 6/2013 | Dinville et al. | |
| 2013/0166029 A1 | 6/2013 | Dinville et al. | |
| 2013/0226300 A1 | 8/2013 | Chataigner et al. | |
| 2015/0051702 A1 | 2/2015 | Chataigner et al. | |
| 2015/0127107 A1 | 5/2015 | Kim et al. | |
| 2015/0209089 A1 | 7/2015 | Chataigner et al. | |
| 2015/0320568 A1 | 11/2015 | Ameil et al. | |
| 2016/0058564 A1 | 3/2016 | Zappacosta et al. | |
| 2016/0058565 A1 | 3/2016 | Zappacosta et al. | |

FOREIGN PATENT DOCUMENTS

| | | |
|---|---|---|
| EP | 3139867 A1 | 3/2017 |
| FR | 2916956 A1 | 12/2008 |
| FR | 2954692 A1 | 7/2011 |
| FR | 3005569 A1 | 11/2014 |
| FR | 3020756 A1 | 11/2015 |
| WO | WO-0049977 A1 | 8/2000 |
| WO | WO-2006026425 A2 | 3/2006 |
| WO | WO-2008150724 A1 | 12/2008 |
| WO | WO-2013062716 A1 | 5/2013 |
| WO | WO-2015169878 A1 | 11/2015 |

OTHER PUBLICATIONS

"U.S. Appl. No. 14/246,442, Non Final Office Action dated Aug. 15, 2017", 11 pgs.

"U.S. Appl. No. 14/246,442, Non Final Office Action dated Nov. 1, 2016", 8 pgs.

"U.S. Appl. No. 14/246,442, Response filed Feb. 1, 2017 to Non Final Office Action dated Nov. 1, 2016", 10 pgs.

"U.S. Appl. No. 14/246,442, Response filed May 6, 2017 to Final Office Action dated Mar. 6, 2017", 17 pgs.

"U.S. Appl. No. 14/246,442, Response filed Nov. 15, 2017 to Non Final Office Action dated Aug. 15, 2017", 15 pgs.

"U.S. Appl. No. 14/638,746, Examiner Interview Summary dated Nov. 15, 2017", 3 pgs.

"U.S. Appl. No. 14/638,746, Final Office Action dated Oct. 12, 2017", 8 pgs.

"U.S. Appl. No. 14/638,746, Non Final Office Action dated Feb. 6, 2018", 10 pgs.

"U.S. Appl. No. 14/638,746, Non Final Office Action dated Jun. 13, 2017", 16 pgs.

"U.S. Appl. No. 14/638,746, Response filed Jan. 12, 2018 to Final Office Action dated Oct. 12, 2017", 9 pgs.

"U.S. Appl. No. 14/638,746, Response filed Apr. 12, 2018 to Non Final Office Action dated Feb. 6, 2018", 11 pgs.

"U.S. Appl. No. 14/638,746, Response filed Sep. 13, 2017 to Non Final Office Action dated Jun. 13, 2017", 12 pgs.

"Chinese Application Serial No. 201480028167.7, Office Action dated May 16, 2016".

"Chinese Application Serial No. 201480028167.7, Office Action dated May 26, 2016", w/English Translation, 18 pgs.

"France Application Serial No. 1354421, Search Report dated Feb. 12, 2014", 5 pgs.

"France Application Serial No. 1454102, Search Report dated Jan. 29, 2015".

"International Application Serial No. PCT/EP2014/060135, International Preliminary Report on Patentability dated Sep. 18, 2015", 16 pgs.

"International Application Serial No. PCT/EP2014/060135, International Search Report dated Aug. 26, 2014", 7 pgs.

"International Application Serial No. PCT/EP2014/060135, Response filed Jun. 27, 2016 to Written Opinion dated Aug. 26, 2014".

"International Application Serial No. PCT/EP2014/060135, Written Opinion dated Aug. 26, 2014", 14 pgs.

"International Application Serial No. PCT/EP2015/060001, International Preliminary Report on Patentability dated Nov. 17, 2016", 6 pgs.

"International Application Serial No. PCT/EP2015/060001, International Search Report dated Oct. 2, 2015", 3 pgs.

"International Application Serial No. PCT/EP2015/060001, Written Opinion dated Oct. 2, 2015", 4 pgs.

"U.S. Appl. No. 14/638,746, Non Final Office Action dated Feb. 5, 2019", 4 pgs.

"European Application Serial No. 15724950.9, Response filed Jul. 13, 2017 to Communication Pursuant to Rules 161(1) and 162 EPC dated Jan. 3, 2017", 15 pgs.

"U.S. Appl. No. 14/638,746, Notice of Allowance dated Jul. 18, 2019", 6 pgs.

"U.S. Appl. No. 14/638,746, Response filed May 6, 2019 to Non Final Office action dated Feb. 5, 2019", 6 pgs.

\* cited by examiner

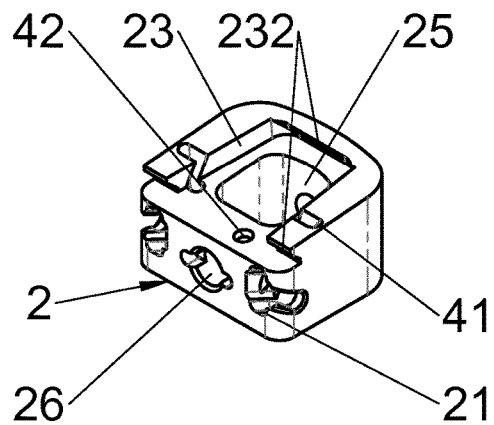
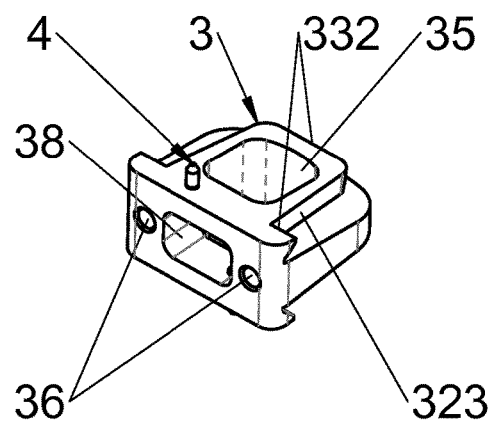
Figure 6A
Figure 6B
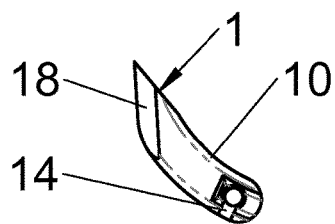
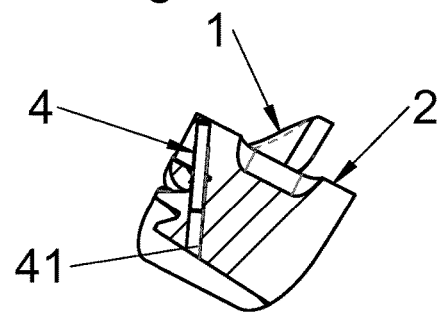
Figure 6C
Figure 6D
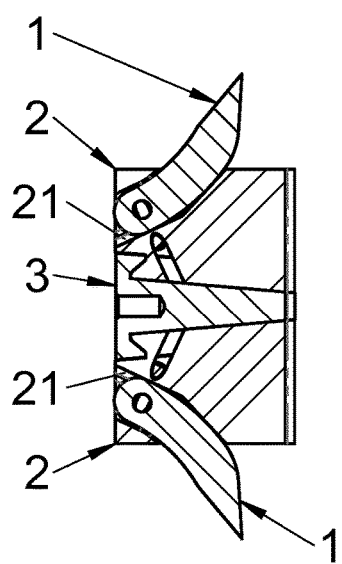
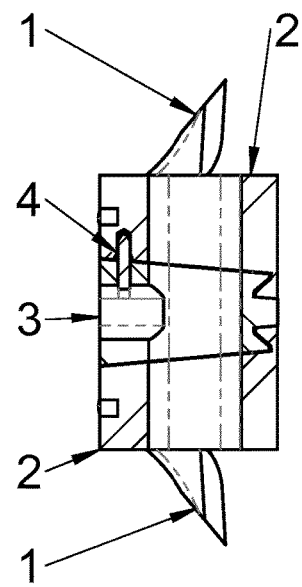
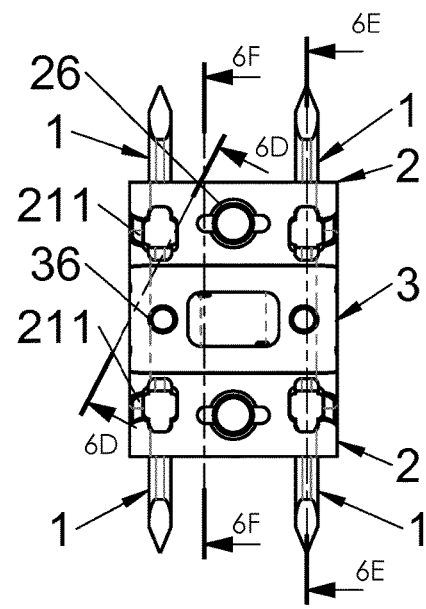
Figure 6E
Figure 6F
Figure 6G

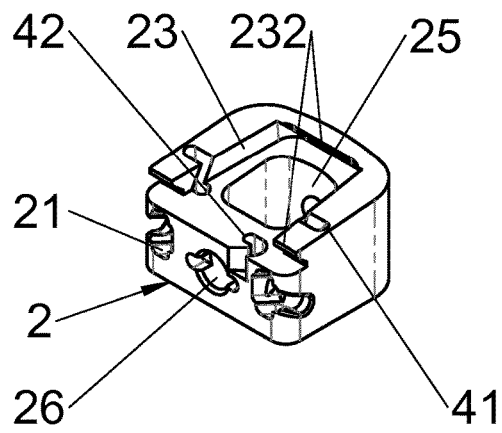
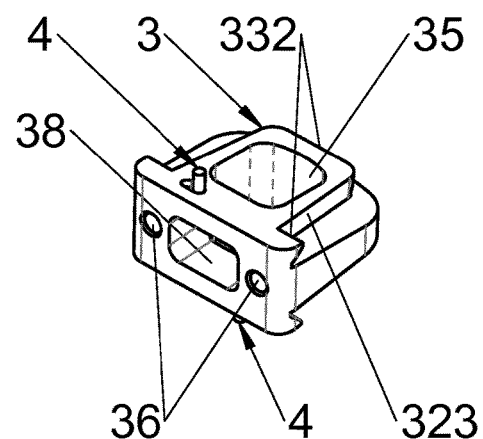
Figure 7A
Figure 7B
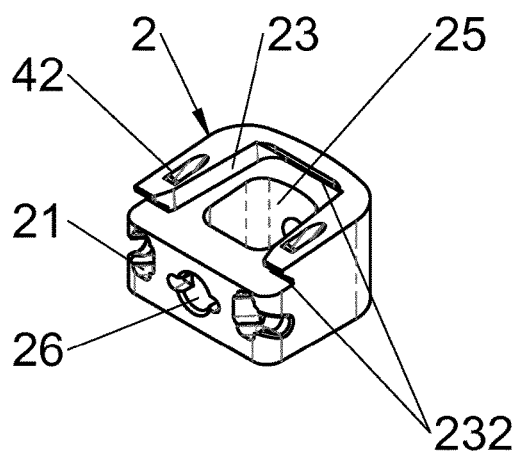
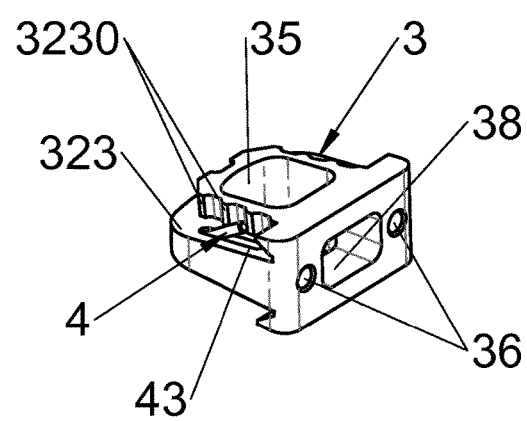
Figure 7C
Figure 7D
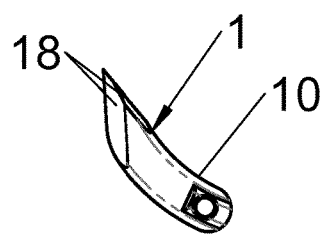
Figure 7E

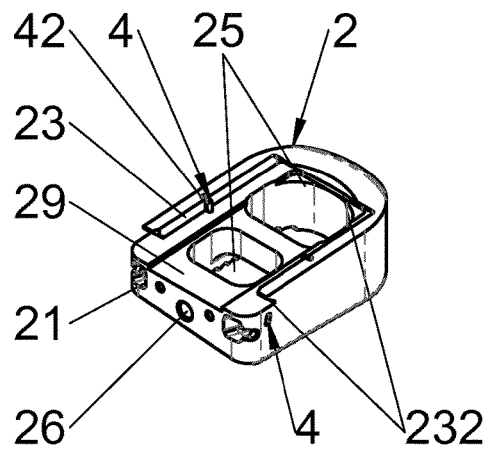
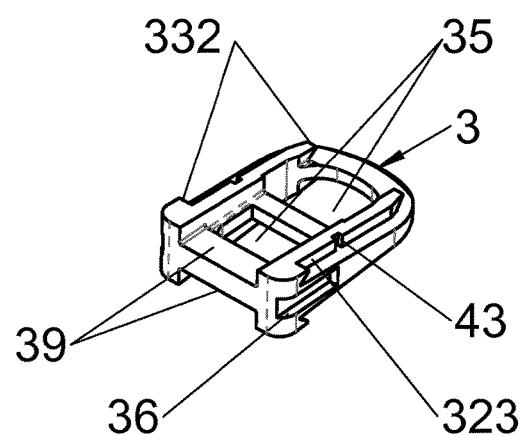
Figure 11A
Figure 11B
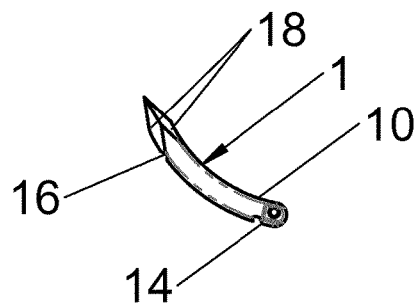
Figure 11C
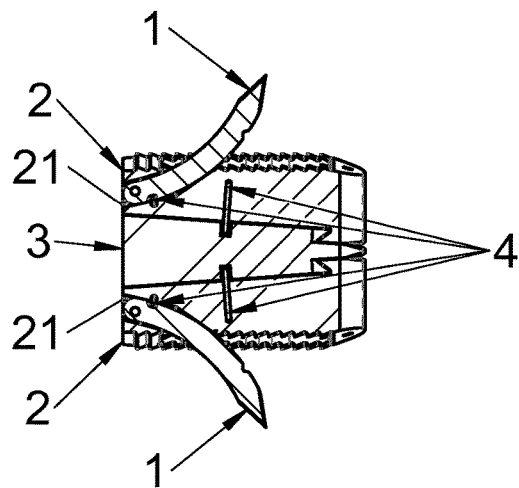
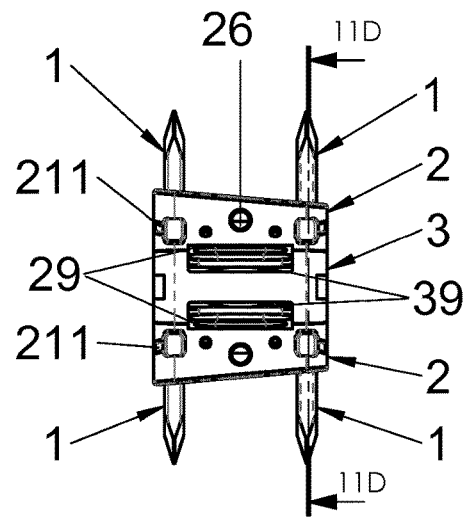
Figure 11D
Figure 11E

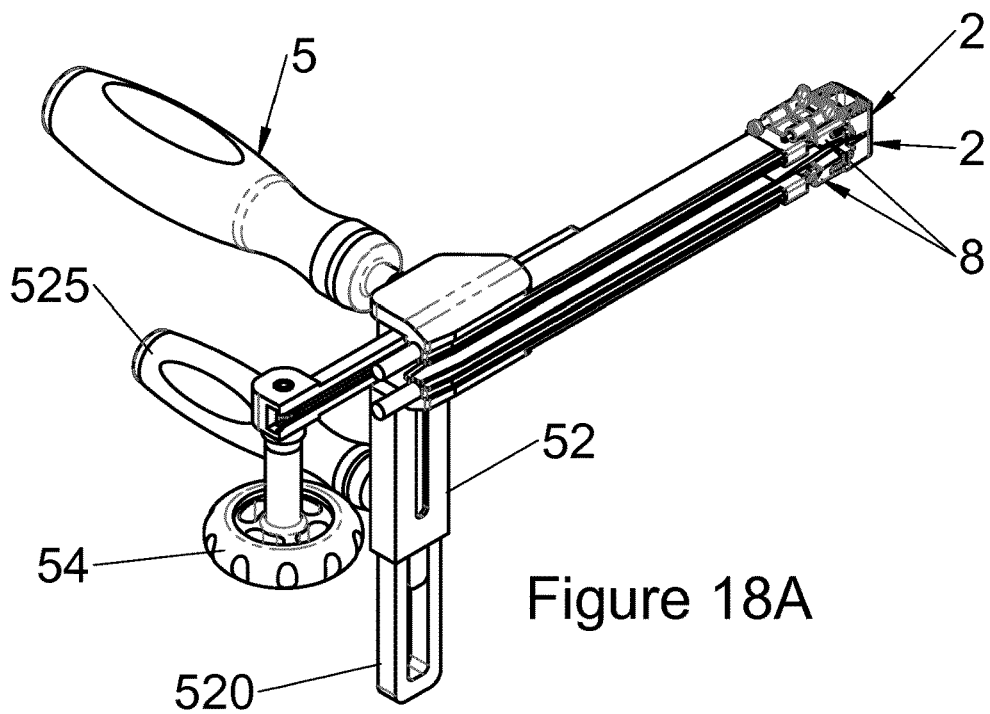
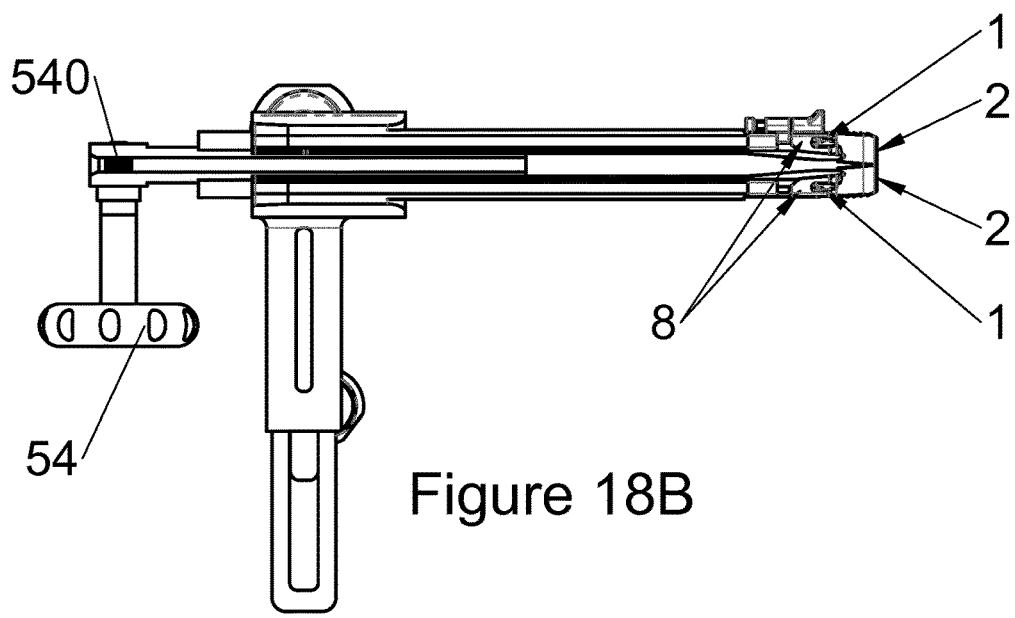
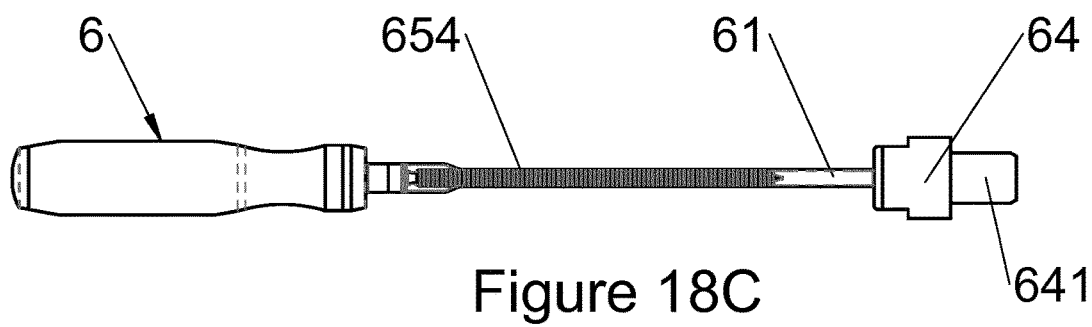
Figure 18A
Figure 18B
Figure 18C

VERTEBRAL IMPLANT, DEVICE FOR VERTEBRAL ATTACHMENT OF THE IMPLANT AND INSTRUMENTATION FOR IMPLANTATION THEREOF

CROSS-REFERENCE TO RELATED APPLICATIONS

This application is a National Stage entry of International Application No. PCT/EP2015/060001 filed May 6, 2015, which claims priority in accordance with 35 U.S.C. §§ 365 and 120 to U.S. patent application Ser. No. 14/638,746 filed Mar. 4, 2015, and priority is claimed in accordance with 35 U.S.C. §§ 365 and 119 to French Patent Application No. FR1454102 filed in FRANCE on May 6, 2014, through International Application No. PCT/EP2015/060001 and U.S. patent application Ser. No. 14/638,746. International Application No. PCT/EP2015/060001 and U.S. patent application Ser. No. 14/638,746 are incorporated herein by reference.

TECHNICAL FIELD OF THE INVENTION

The present application relates to the field of vertebral implants, including corpectomy cages and intersomatic cages, intended to replace a vertebral segment, i.e. all or part of at least one vertebral body and/or at least one intervertebral disc. The present application also relates to devices for vertebral attachment of such implants and to instrumentation for implantation thereof.

TECHNOLOGICAL BACKGROUND OF THE INVENTION

A problem in the field of vertebral implants and notably of corpectomy cages sometimes relates to the deployment of an implant capable of replacing a vertebral segment, sometimes with a large size, at least in height, for a corpectomy cage since the vertebral segment may correspond to all or part of at least one vertebral body and/or at least one intervertebral disc. Indeed, certain pathologies, notably cancer diseases, may result in a degradation of the vertebral bodies (either partly or completely) and/or of the intervertebral discs. It is then sometimes desirable to replace the lesioned vertebral segments(s) with an implant of significant height. Further, it is often desirable to be able to modulate the height of the implant during surgery since the ablation of the lesioned structures generally require distraction of the vertebrae for restoring a physiological (or less pathological) height to the treated vertebral segment and this height varies according to the extent of the lesions (for inserting the implant between healthy tissues).

A problem related to the height of the implants sometimes involves the stabilization of the implant against the vertebral structures between which it is inserted. The required distraction is sometimes not very compatible with numerous stabilization solutions, such as notches on the contact surfaces of the implants, since these notches often make it necessary to make an additional distraction for inserting the implant. Further, the anchoring of the implant is generally preferable to simple notches which generally only limit the risk of movement but do not enhance reliable immobilization.

In the prior art, solutions are known, notably for corpectomy, such as expandable cages in situ, generally comprising a body including moveable elements providing the vertebral contact surfaces and giving the possibility of increasing the height of the implant once the latter is inserted between the vertebrae. These solutions have the drawbacks of relying on generally complex and costly mechanisms, which often make the implant and/or the vertebrae fragile since the distraction obtained by the implant during its expansion often does not give the possibility of estimating the exerted force because the surgeon often does not feel enough the force he/she generates during the distraction (such that the implants sometimes collapse in the vertebrae). Further, they often provide a reduced grafting space, not allowing the addition of a bone graft or substitute, sufficient for quality arthrodesis. Similarly, such implants are often made of metallic material, which does not allow viewing of the bone growth into the cage during inspections by post-operative imaging. On the other hand, these solutions often have a small expansion ratio (1/3) and therefore generally require that the compressed implant already have a significant size so that its size is satisfactory when it is expanded and the design of these cages makes it often necessary to release the distraction in order to allow insertion into the vertebral segment. Moreover, as the vertebrae can be deformed or crushed or even packed, the implant must be able to be inserted with the smallest possible height and then to be enlarged to the maximum. These types of expandable cages are often incompatible with notches or teeth for stabilization (since the latter reduce the actual distraction capability, interfere with the positioning and risk making the adjacent vertebral structures fragile) and/or with anchoring (since the cages generally do not provide a sufficiently wide structure for retaining an anchoring means). Moreover, anchoring with screws may prove to be tedious to set into place and requires an overly invasive approach.

Other problems, often related to expandable cages in situ and to the drawbacks of certain of the solutions of the prior art, sometimes relate to the insertion of the implant into the rachis, which is generally difficult on the one hand and the assembling and locking of the various elements of the implant, which have to be sufficiently easy and reliable for providing a solution limiting the dislocation risks of the implant on the other hand.

Another problem in the field relates to invasivity and in particular to accessing the intervertebral spaces (discal spaces) which is often particularly delicate because of the congestion, notably because of the presence of blood vessels and nerves in the neighborhood of the intervertebral space, as well as the proximity of the spinal cord. The bone anchoring devices which have to penetrate sufficiently deeply into the vertebrae for ensuring proper attachment, therefore also have to have a small enough size and allow attachment of the implant without jeopardizing the surrounding blood vessels and nerve tissues (for example not requiring more space in the surroundings of the intervertebral space than necessary for implanting the actual rachidian implant). Such anchoring means therefore preferably also have to address the problem of limiting invasivity, in addition to reliability and stability.

Another problem for bone anchoring means often related to the drawbacks of certain of the solutions of the prior art, sometimes relates to the removal of the bone anchoring means and/or of the implant, since removal is generally impossible or difficult. Indeed, it is generally desired to be able to remove the bone anchoring means (and generally the implant). Therefore the bone anchoring means preferably can be retained in the implant in a stable way but they may also be removed as easily as possible. Further, easy removal should also be preferably achieved with an invasivity as limited as possible.

In this context, it is worth proposing various embodiments of implants that address one or more of the known problems, for example by being easily implantable, robust and reliable, and adaptable in different sizes and preferably expandable within the patient, perhaps notably by limiting the dislocation risks and/or which may limit the risks of making the adjacent vertebral structures fragile and/or which allow anchoring in the vertebral bodies without compromising the final positioning, for example while allowing removal and/or avoiding greater distraction than required for inserting the implant.

GENERAL DESCRIPTION OF THE INVENTION

Various embodiments of the present application are configured for removing or reducing at least one of the drawbacks of the prior art, including those from among the drawbacks discussed above, for example by proposing a vertebral implant, such as for corpectomy, that has an adaptable size, that is easy to implant and that reliably attaches to the vertebral structures adjacent to the replaced vertebral segment.

Various of such goals, for example, may be achieved with various embodiments of this disclosure, such as implants for corpectomy or fusion, intended to be inserted into the rachis according to at least one approach route, for replacing a vertebral segment, the implant extending along a vertical axis, between upper and lower surfaces of the implant each intended to be placed in contact with a respectively upper and lower structure, of said vertebral segment. In various embodiments, the implant includes at least one first body and at least one second body each having at least mutual fitting means in order to allow assembling of said bodies by sliding along a sliding axis, and at least one locking means retained in or on at least one of the bodies, and at least one abutment portion of which is laid out for passing from a so-called open position, allowing sliding for the assembling of said bodies, to a so-called closed position locking said bodies assembled together by the contact between at least said abutment portion and at least one abutment of at least one of said bodies, said abutment being oriented not parallel to the sliding axis and said abutment portion passing from the open position to the closed position elastically by flexure or torsion, by means of at least one flexible portion of the locking means allowing withdrawal of said abutment portion of the locking means in an open position during the sliding of the bodies on the one hand and elastic return of said abutment portion into the closed position when it is found facing said abutment of said body on the other hand.

According to some other features, in some embodiments, the locking means are retained on the implant by being disposed in at least one groove around at least part of at least one of the bodies and by the abutment portion of the same or other body.

According to some other features, in some embodiments, the locking means are retained on the implant by being disposed in at least one groove around at least part of at least one of the bodies and by the abutment portion of the same or other body.

According to some other features, in some embodiments, the implant may include two first bodies each comprising one of said upper and lower surfaces of the implant and at least one second body inserted between the two first bodies by means of said mating faces allowing assembling of the bodies by sliding.

According to some other features, in some embodiments the sliding axis of the bodies is substantially parallel to the approach route provided for inserting the implant into the rachis.

According to some other features, in some embodiments said mating faces of the bodies are tilted relatively to the plane(s) of the upper and lower surfaces of the implant, so that the assembling of the bodies is accomplished by starting from their respective side with a lower height and the sliding occurs according to a tilted plane allowing restoration of a determined height to the implant and compression of the implant.

According to some other features, in some embodiments said mating faces of the bodies are substantially parallel to the plane(s) of the upper and lower surfaces of the implant and/or perpendicular to the vertical axis, so that the sliding of the bodies occurs in this plane with which it is possible to retain a determined height of the implant.

According to some other features, in some embodiments the mutual fitting means of said mating faces of the bodies prevent the movements of the two bodies along at least one direction not parallel to the sliding axis.

According to some other features, in some embodiments the mutual fitting means of said mating faces of the bodies include at least one abutment limiting the sliding travel of the bodies relatively to each other.

According to some other features, in some embodiments the mutual fitting means of said mating faces of the bodies include at least one abutment preventing both bodies from moving away from each other in at least one direction substantially parallel to the vertical axis.

According to some other features, in some embodiments the implant includes bone anchoring means, the deployment of which allows anchoring of the implant in said lower and upper vertebral structures, each of said bone anchoring means being deployed by sliding inside the implant, along a curvilinear path, through a passage between the outside of the peripheral wall and one of the upper and lower surfaces of the implant, and comprising at least one curved plate, at least one posterior portion of which remains inside the passage at the end of the deployment on the one hand and, at least one anterior end jutting out from one of the upper and lower surfaces of the implant in order to penetrate into one of said vertebral structures at the end of the deployment on the other hand.

According to some other features, in some embodiments the bone anchoring means are locked in the implant with at least one locking means retained in at least one of the bodies and at least one abutment portion of which is laid out for passing from a so-called open position allowing the sliding of the bone anchoring means in their passage to a so-called closed position locking, preventing sliding of the bone anchoring means by the contact between at least said abutment portion and at least one abutment of the bone anchoring means, said abutment being oriented not parallel to the path of said passage and said abutment portion passing from the open position to the closed position, elastically by flexure or by torsion, by means of at least one flexible portion of the locking means allowing withdrawal of said abutment portion of the locking means in an open position during the sliding of the bone anchoring means on the one hand and, elastic return of said abutment portion into a closed position when it is found facing said abutment of the bone anchoring means on the other hand.

According to some other features, in some embodiments at least one posterior portion of the curve plate includes at least one notch engaging into the wall of the passage of the implant for immobilizing the bone anchoring means at the end of the deployment.

According to some other features, in some embodiments at least one posterior portion of the curved plate includes at least one abutment mating an abutment in the passage of the implant for immobilizing the bone anchoring means at the end of the deployment, said curved plate including, on at least one posterior portion, a slot crossing the whole of its thickness giving the possibility of providing elasticity to this posterior portion and the possibility of mutual engagement of these abutments and their clearing upon withdrawal of the bone anchoring means.

According to some other features, in some embodiments a same locking means locks at least two bodies and at least one bone anchoring means at a time.

According to some other features, in some embodiments the bodies and the bone anchoring means are locked by different locking means.

According to some other features, in some embodiments the implant includes at least one means for accessing at least one locking means for placing the latter in an open position in order to obtain unlocking.

According to some other features, in some embodiments said at least one locking means is substantially oriented parallel to the vertical axis and its abutment portion moves elastically, between the open position and the closed position, along a direction perpendicular to the vertical axis and not parallel to the sliding axis.

According to some other features, in some embodiments at least one locking means is positioned in a closed position, in a transverse plane substantially perpendicular to the vertical axis and its abutment portion is positioned outside this plane when the locking means is in the open position.

According to some other features, in some embodiments said at least one locking means is positioned, in an open position, in a plane substantially perpendicular to the vertical axis, preferably along a direction parallel to the sliding axis and its abutment portion is positioned outside this plane when it is in a closed position.

According to some other features, in some embodiments said at least one locking means is positioned in a transverse plane substantially perpendicular to the vertical axis and its abutment portion moves elastically, between the open position and the closed position, substantially in this transverse plane.

According to some other features, in some embodiments said curved plate is positioned in a vertical plane inside the passage of the implant and the curvature of the plate is oriented in this vertical plane.

According to some other features, in some embodiments said curve plate includes, in proximity to its posterior end, at least one abutment surface, not parallel to the surface of the plate for limiting the penetration of the bone anchoring means into the implant.

According to some other features, in some embodiments said anterior end includes at least one spike and/or at least one sharpened portion facilitating penetration into the vertebral structures.

According to some other features, in some embodiments the peripheral wall includes hooking-up means for implantation instrumentation.

According to some other features, in some embodiments the implant is hollow, by means of at least one opening extending from said upper surface as far as said lower surface.

According to some other features, in some embodiments the peripheral wall includes at least one conduit for allowing insertion of a bone graft and/or substitute.

Various other embodiments of implants also give the possibility of serving at least one of the purposes of the present application.

Various of such goals, for example, may be achieved with various embodiments of this disclosure, such as a vertebral, in particular corpectomy, implant intended to be inserted into the rachis according to at least one approach route, for replacing a vertebral segment, the implant extending along a vertical axis, between upper and lower surfaces of the implant each intended to be placed in contact with a respectively upper and lower structure, of said vertebral segment, the implant being characterized in that it includes at least one first body and at least one second body each having at least mutual fitting means in order to allow assembling of said bodies by sliding along a sliding axis and on the other hand, at least one locking means retained in or on at least one of the bodies and comprising actuating means causing translation of the locking means parallel to the sliding axis and enabling at least one abutment portion of the locking means to come into contact with at least one portion of another body, along a surface of each of these portions which are oriented substantially parallel to said sliding axis, preferably with a light tilted orientation.

According to some other features, in some of these embodiments, the actuation means comprise locking means for locking the actuation and therefore locking the locking means.

Some of these embodiments include a vertebral implant, for example corpectomy or fusion, intended to be inserted into the rachis according to at least one approach route, for replacing a vertebral segment, the implant extending along a vertical axis, between upper and lower surfaces of the implant each intended to be placed in contact with a respectively upper and lower structure, of said vertebral segment, in which the implant includes at least one first body and at least one second body each having at least one face having shapes and dimensions mating those of at least one face of another body and forming mutual fitting means in order to allow assembling of said bodies by sliding along a sliding axis not parallel to the vertical axis and on the other hand, at least one locking means retained in at least one of the bodies and at least one abutment portion of which is laid out for passing from a so-called open position, allowing sliding for the assembling of said bodies, to a so-called closed position locking said bodies assembled together by the contact between at least said abutment portion and at least one abutment of at least one of said bodies, said abutment being oriented not parallel to the sliding axis and said abutment portion passing from the open position to the closed position, by actuating said locking means in translation along a direction not parallel to the sliding axis.

Some other embodiments may include a vertebral implant, for example corpectomy or fusion, intended to be inserted into the rachis according to at least one approach route, for replacing a vertebral segment, the implant extending along a vertical axis, between upper and lower surfaces of the implant each intended to be placed in contact with a respectively upper and lower structure, of said vertebral segment, in which the implant includes at least one first body and at least one second body each having at least one face having shapes and dimensions mating those of at least one face of another body and forming mutual fitting means in order to allow assembling of said bodies by sliding along a sliding axis not parallel to the vertical axis and on the other hand, at least one locking means retained in at least one of the bodies and at least one abutment portion of which is laid out for passing from a so-called open position, allowing sliding for the assembling of said bodies, to a so-called closed position locking said bodies assembled together by the contact between at least said abutment portion and at least one abutment of at least one of said bodies, said abutment being oriented not parallel to the sliding axis and said abutment portion passing from the open position to the closed position, by actuating means actuated in rotation around an axis parallel to the sliding axis and leading to either:

A pivoting of said abutment around this axis parallel to the sliding axis, or

A translation of the locking means along a direction not parallel to the sliding axis, or A translation of the locking means along a direction parallel to the sliding axis.

Some others of these embodiments include a vertebral implant, for example corpectomy or fusion, intended to be inserted into the rachis according to at least one approach route, for replacing a vertebral segment, the implant extending along a vertical axis, between upper and lower surfaces of the implant each intended to be placed in contact with a respectively upper and lower structure, of said vertebral segment, in which the implant includes at least one first body and at least one second body each having at least one face having shapes and dimensions mating those of at least one face of another body and forming mutual fitting means in order to allow assembling of said bodies by sliding along a sliding axis not parallel to the vertical axis and on the other hand, at least one locking means retained in at least one of the bodies and at least one abutment portion of which is laid out for passing from a so-called open position, allowing sliding for the assembling of said bodies, to a so-called closed position locking said bodies assembled together by the contact between at least said abutment portion and at least one abutment of at least one of said bodies, said abutment being oriented not parallel to the sliding axis and said abutment portion passing from the open position to the closed position, by actuating means actuated in translation along a direction parallel to the sliding axis and leading to either:

A translation of the locking means along a direction not parallel to the sliding axis, or A pivoting of said abutment around an axis parallel to the sliding axis.

Other particularities and advantages of various embodiments of the present application are detailed in the description which follows.

DESCRIPTION OF THE ILLUSTRATIVE FIGURES

Other particularities and advantages of the present disclosure will become more clearly apparent upon reading the description hereafter, made with reference to the appended drawings, wherein:

FIGS. 1A and 1B illustrate perspective views of a first body and of a second body of an implant according to certain embodiments, respectively, FIG. 1C illustrates a profile view of an anchoring device according to certain embodiments, FIG. 1F illustrates a front view of an implant provided with anchoring devices of FIG. 1C and consisting of the assembly of two first bodies of FIG. 1A and of a second body of FIG. 1B, FIG. 1E illustrates a sectional view along the sectional plane 1E-1E of FIG. 1F and FIG. 1D illustrates a sectional view along the sectional plane 1D-1D of FIG. 1E;

FIGS. 2A and 2B illustrate perspective views of a first body and of a second body of an implant according to certain embodiments, respectively, FIG. 2C illustrates a profile view of an anchoring device according to certain embodiments, FIG. 2G illustrates a front view of an implant provided with anchoring devices of FIG. 2C and consisting of the assembly of two first bodies of FIG. 2A and of a second body of FIG. 2B, FIG. 2F illustrates a sectional view along the sectional plane 2F-2F of FIG. 2G, FIG. 2D illustrates a sectional view along the sectional plane 2D-2D of FIG. 2F, and FIG. 2E illustrates a perspective view of a guiding means according to various embodiments;

FIGS. 3A and 3B illustrate perspective views of a first body and of a second body of an implant according to certain embodiments, respectively, FIG. 3C illustrates a profile view of an anchoring device according to certain embodiments, FIG. 3D illustrates a perspective view of a first body according to an alternative embodiment of FIG. 3A, FIG. 3F illustrates a front view of an implant provided with anchoring devices of FIG. 3C and consisting of the assembly of two first bodies of FIG. 3D and of a second body of FIG. 3B, and FIG. 3E illustrates a sectional view along the sectional plane 3E-3E of FIG. 3F;

FIGS. 4A and 4B illustrate perspective views of a first body and of a second body of an implant according to certain embodiments, respectively, FIG. 4C illustrates a profile view of an anchoring device according to certain embodiments, FIG. 4D illustrates a perspective view of a locking means according to certain embodiments, FIG. 4F illustrates a front face of an implant provided with anchoring devices of FIG. 4C and consisting of the assembly of two first bodies of FIG. 4A and of a second body of FIG. 4B, and FIG. 4E illustrates a sectional view along the sectional plane 4E-4E of FIG. 4F;

FIGS. 5A and 5B represent perspective views of a first body and of a second body of an implant according to certain embodiments, respectively, FIG. 5C represents a profile view of an anchoring device according to certain embodiments, FIG. 5F illustrates a front view of an implant provided with anchoring devices of FIG. 5C and consisting of the assembly of two first bodies of FIG. 5A and of a second body of FIG. 5B, FIG. 5E illustrates a sectional view along the section plane 5E-5E of FIG. 5F and FIG. 5D illustrates a sectional view along the sectional plane 5D-5D of FIG. 5F;

FIGS. 6A and 6B illustrate perspective views of a first body and of a second body of an implant according to certain embodiments, respectively, FIG. 6C illustrates a profile view of an anchoring device according to certain embodiments, FIG. 6G illustrates a front face of an implant provided with anchoring devices of FIG. 6C and consisting of the assembly of two first bodies of FIG. 6A and of a second body of FIG. 6B, FIGS. 6D, 6E and 6F illustrate sectional views along the sectional planes, 6D-6D, 6E-6E and 6F-6F of FIG. 6G respectively;

FIGS. 7A and 7B illustrate perspective views of a first body and of a second body of an implant according to certain embodiments, respectively, FIGS. 7C and 7D illustrate perspective views, of a first body and of a second body of an implant according to other embodiments, respectively, and FIG. 7E illustrates a profile view of an anchoring device according to certain embodiments, FIGS. 8A and 8B illustrate perspective views of a first body and a second body of an implant according to certain embodiments, respectively, FIG. 8C illustrates a profile view of an anchoring device according to certain embodiments, FIG. 8E illustrates a front view of an implant provided with anchoring devices of FIG. 8C and consisting of the assembly of two first bodies of FIG. 8A and of a second body of FIG. 8B and FIG. 8D illustrates a sectional view along the sectional plane 8D-8D of FIG. 8E;

FIG. 9A illustrates a perspective view of a first body of an implant according to various embodiments, FIGS. 9B, 9C and 9D illustrate perspective views of a second body according to the three different alternative embodiments, FIG. 9F illustrates a front view of an implant provided with anchoring devices of FIG. 9C and consisting of the assembly of two first bodies of FIG. 9A and of a second body of FIG. 9B and FIG. 9E illustrates a sectional view along the sectional plane 9E-9E of FIG. 9F;

FIGS. 10A and 10B illustrate perspective views of a first body and of a second body according to certain embodiments, respectively, FIG. 10C illustrates a perspective view of a locking means according to a certain embodiment, FIG. 10F illustrates a means for actuating the locking means according to various embodiments, FIG. 10G illustrates a front view of an implant according to various embodiments consisting of an assembly comprising two first bodies according to FIG. 10A and of a second body according to FIG. 10B and provided with a locking means of FIG. 10C equipped with the actuation of FIG. 10F, FIG. 10E illustrates a sectional view along the sectional plane 10E-10E of FIG. 10G and FIG. 10D illustrates a sectional view of the implant of FIG. 10G along the sectional plane 10D-10D.

FIGS. 11A and 11B illustrate perspective views of a first body and of a second body according to various embodiments, respectively, FIG. 11C illustrates a profile view of an anchoring device according to certain embodiments, FIG. 11E illustrates a front view of a vertebral implant consisting of an assembly of two first bodies of FIG. 11A and of a second body of FIG. 11B provided with anchoring devices according to FIG. 11C, and FIG. 11D illustrates a sectional view of the implant of FIG. 11E along the sectional plane 11D-11D;

Figure 14A:
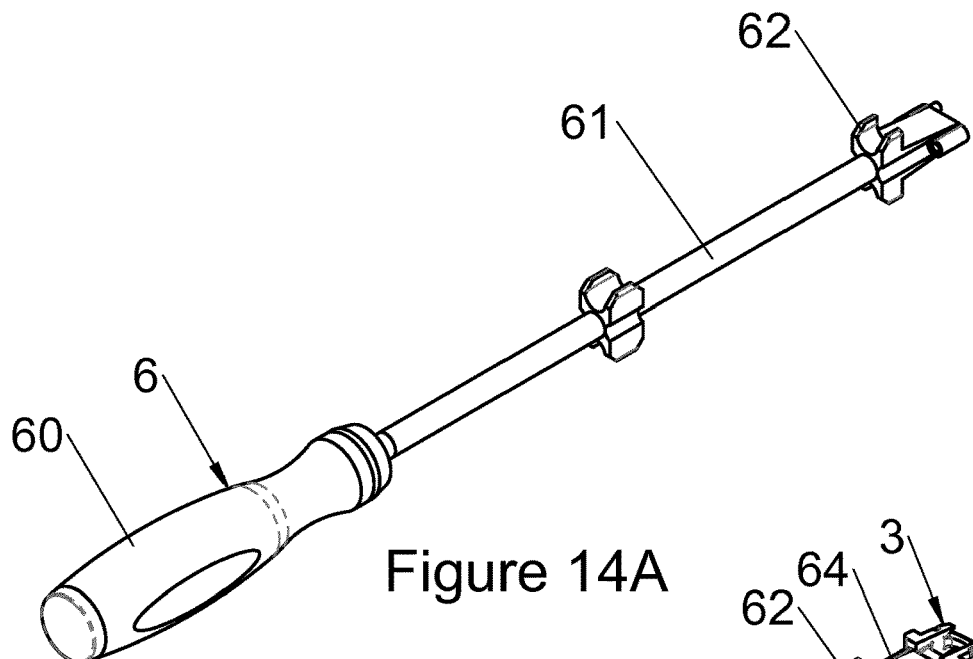
Figure 14B:
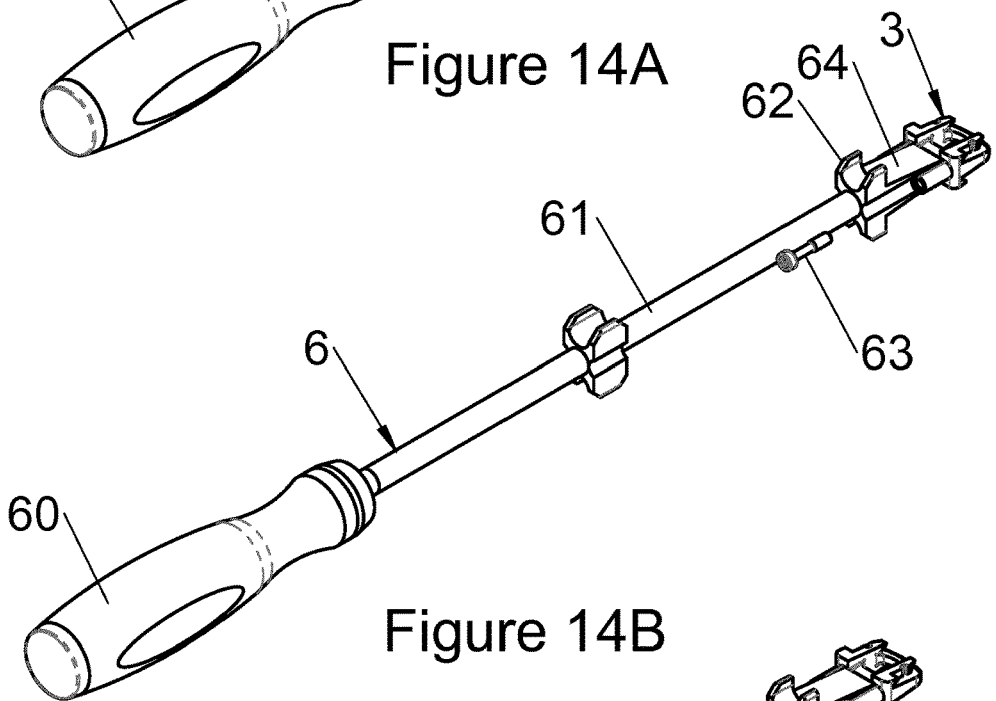
Figure 14C:
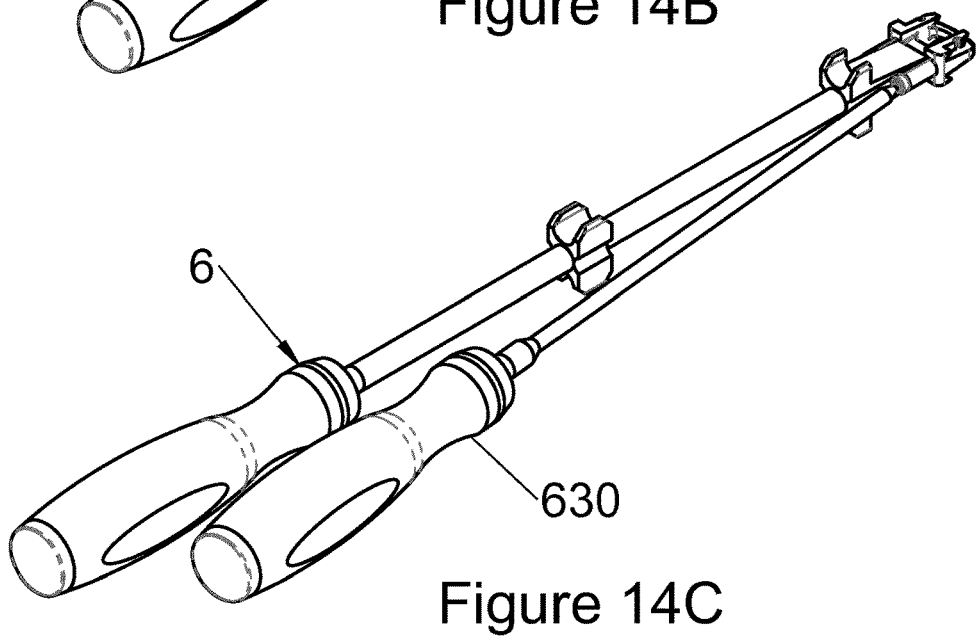
Figure 15A:
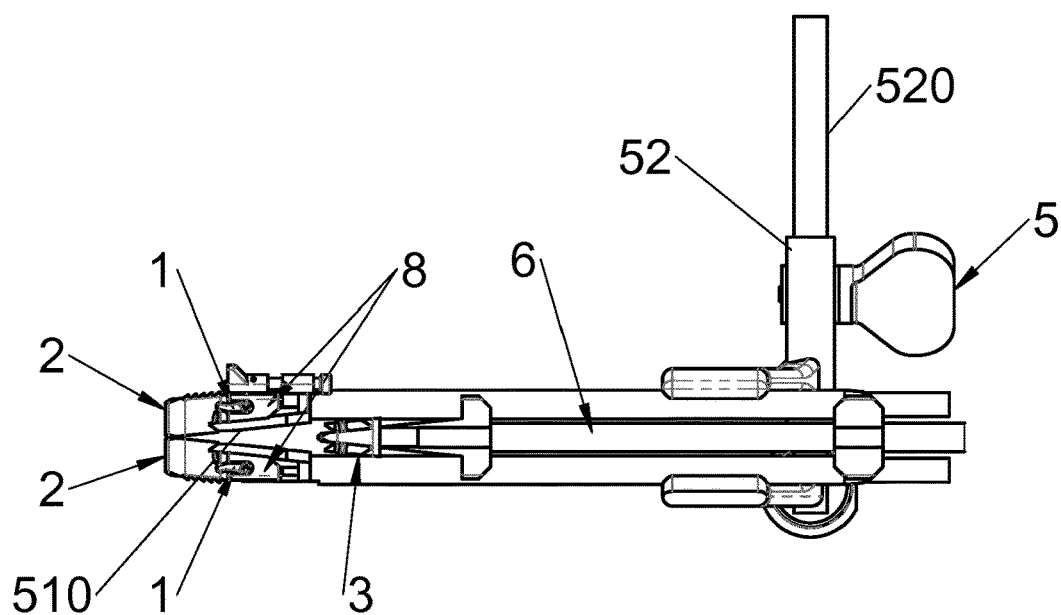
Figure 15B:
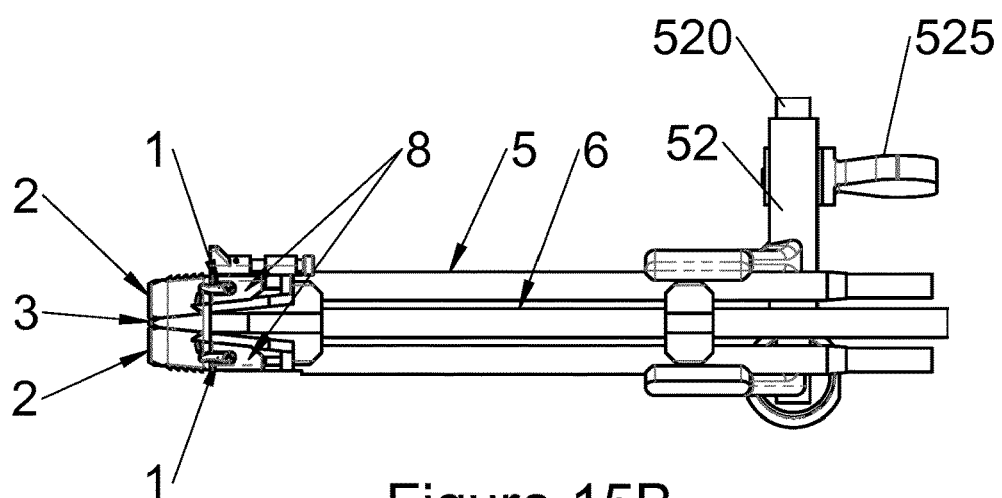
Figure 15C:
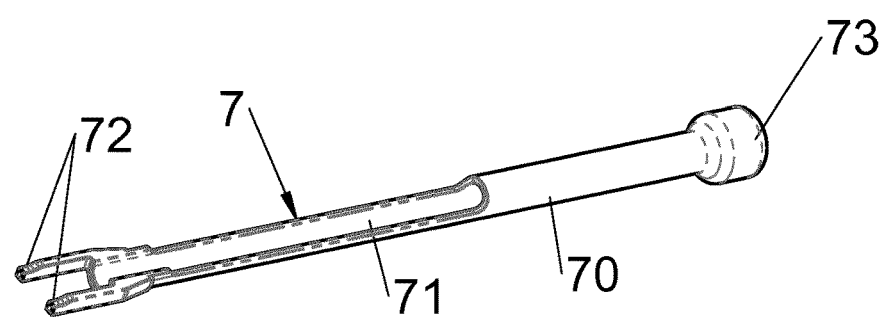
Figure 16A:
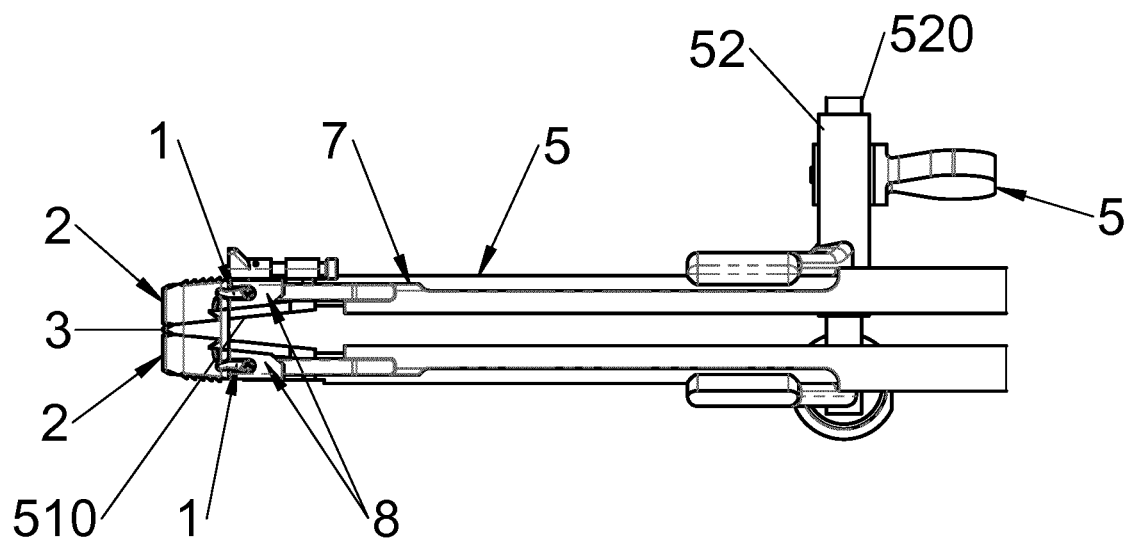
Figure 16B:
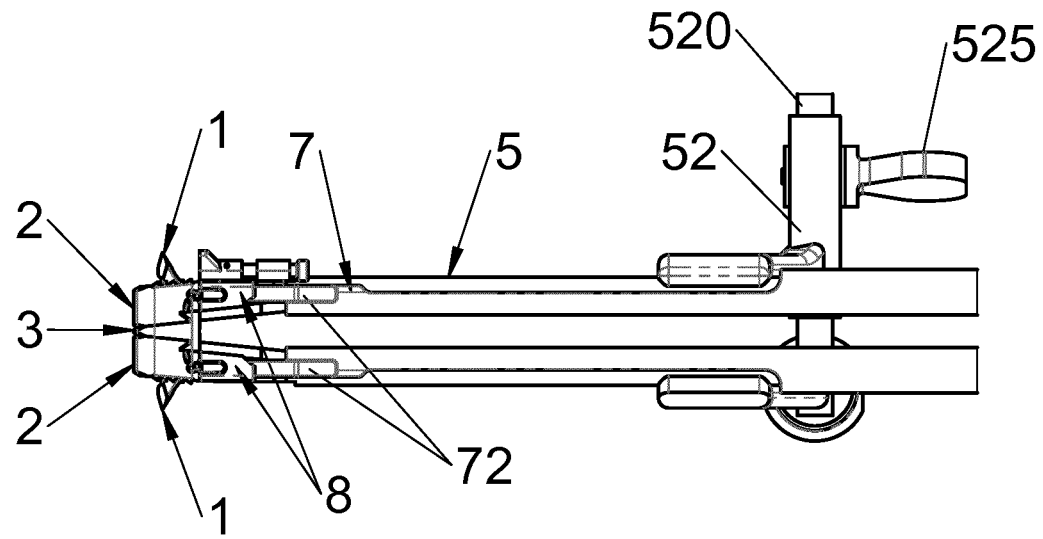
Figure 17A:
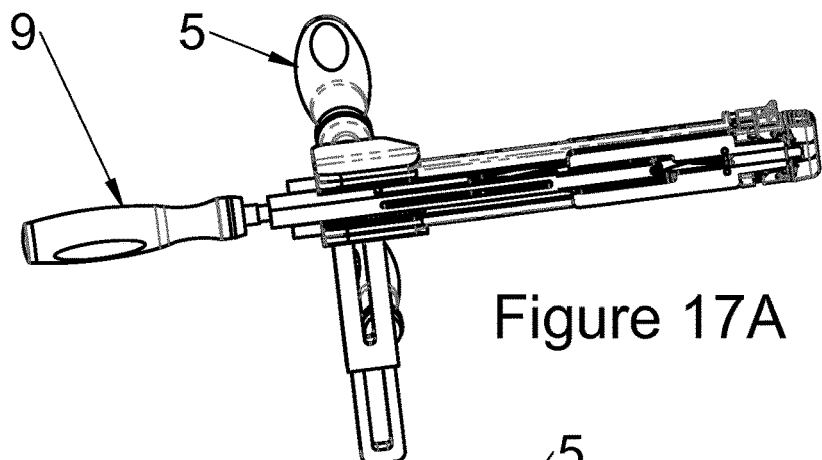
Figure 17B:
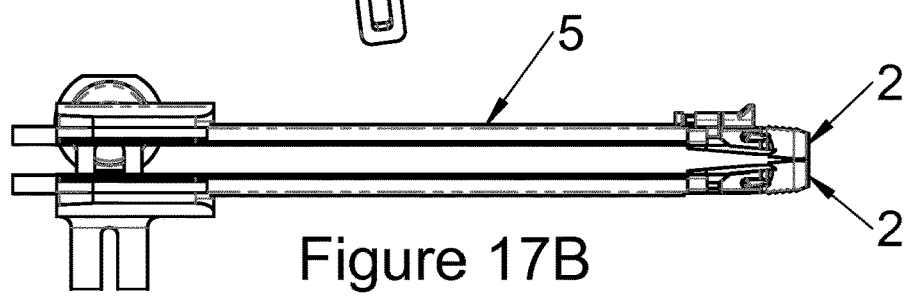
Figure 17C:
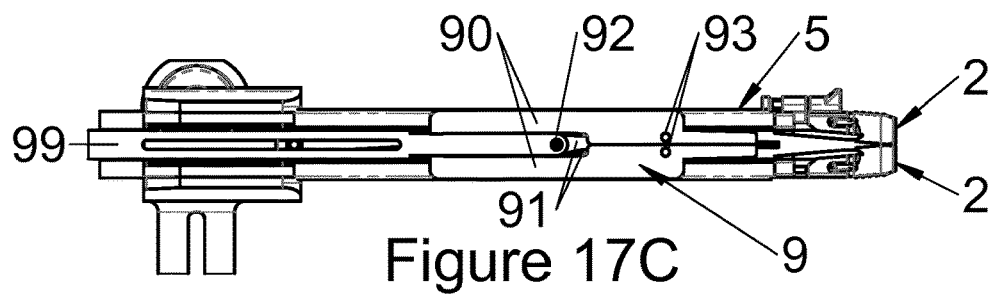
Figure 17D:
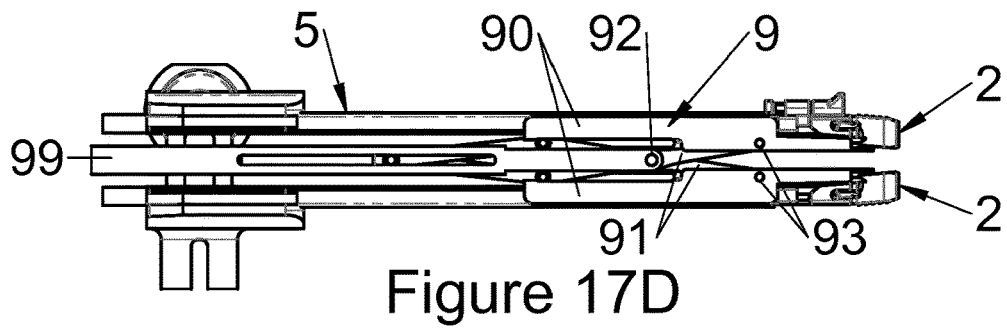
Figure 17E:
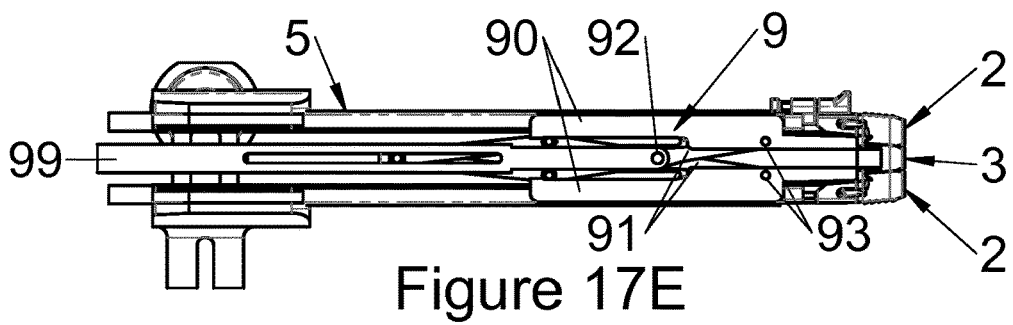
Figure 19A:
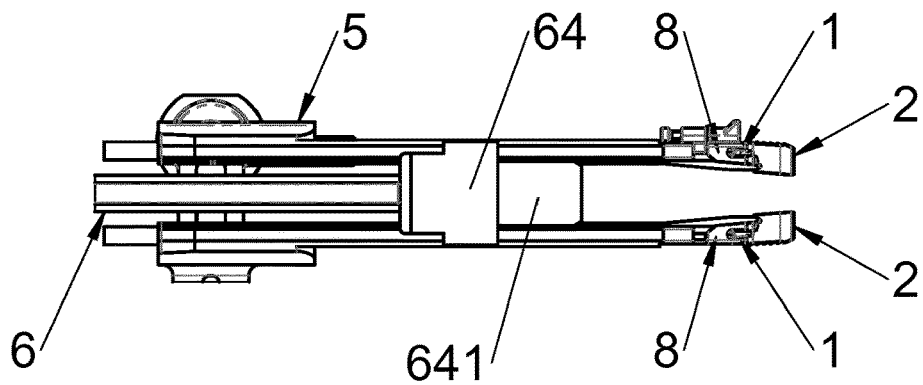
Figure 19B:
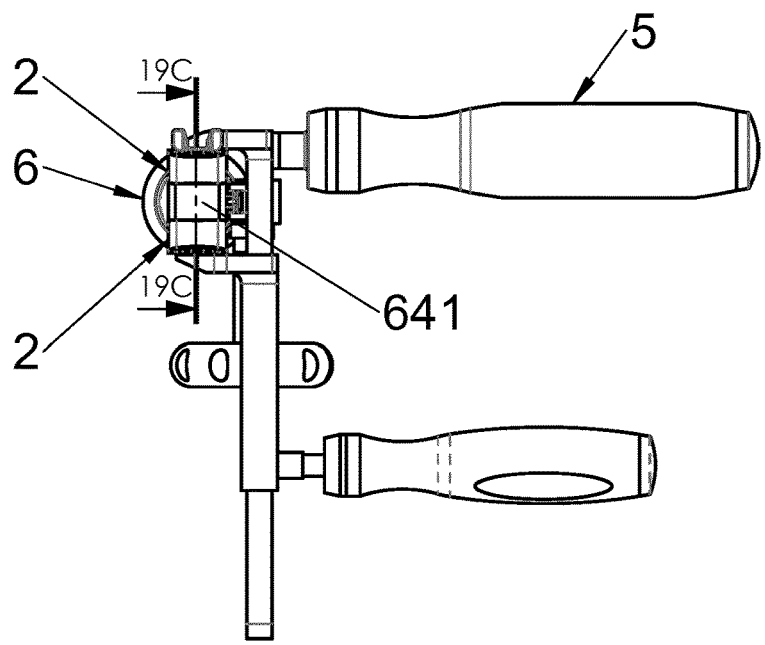
Figure 19C:
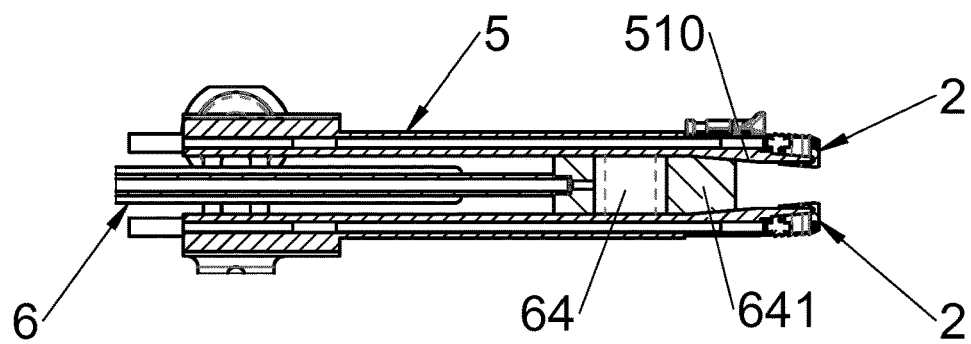
Figure 20A:
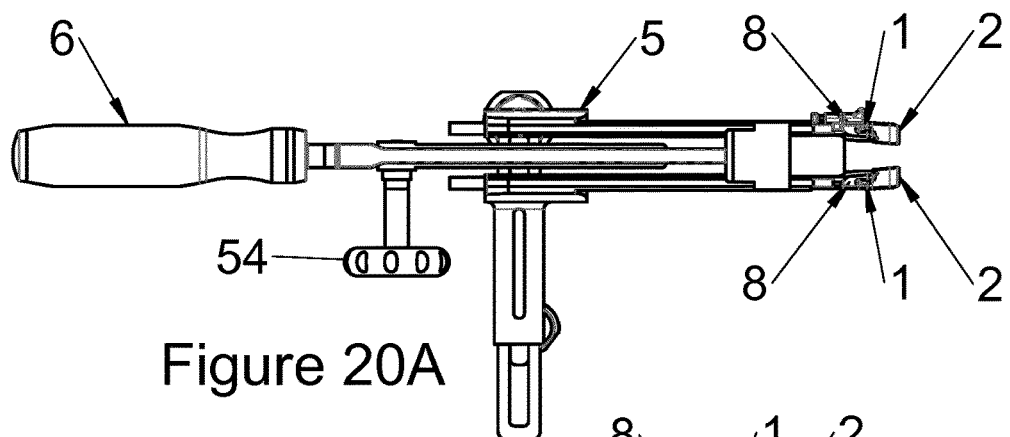
Figure 20B:
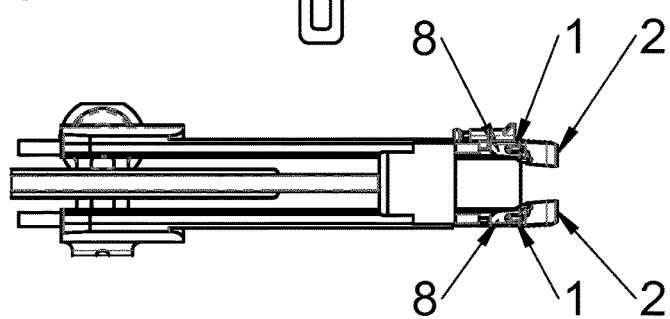
Figure 20C:
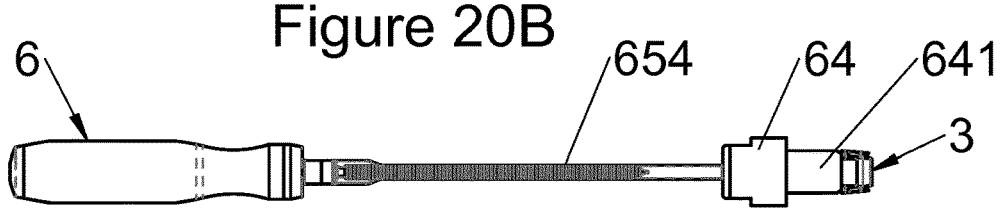
Figure 20D:
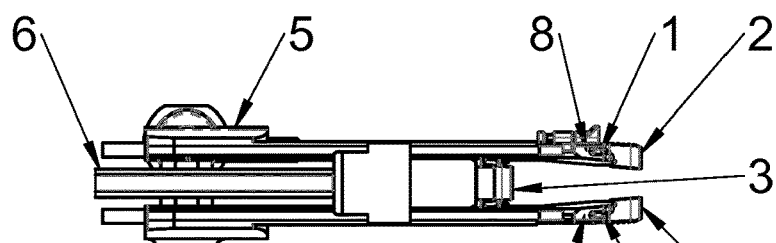
Figure 20E:
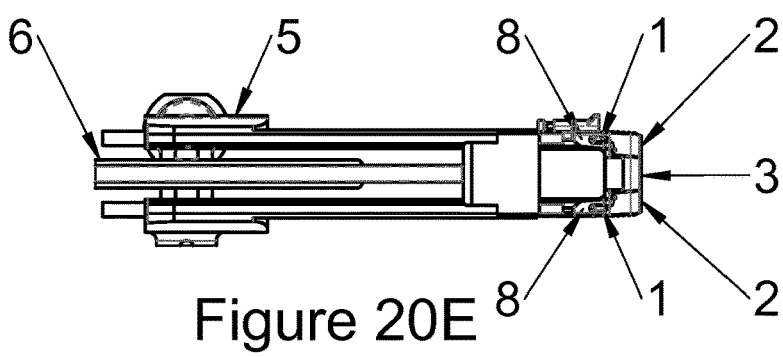
Figure 21A:
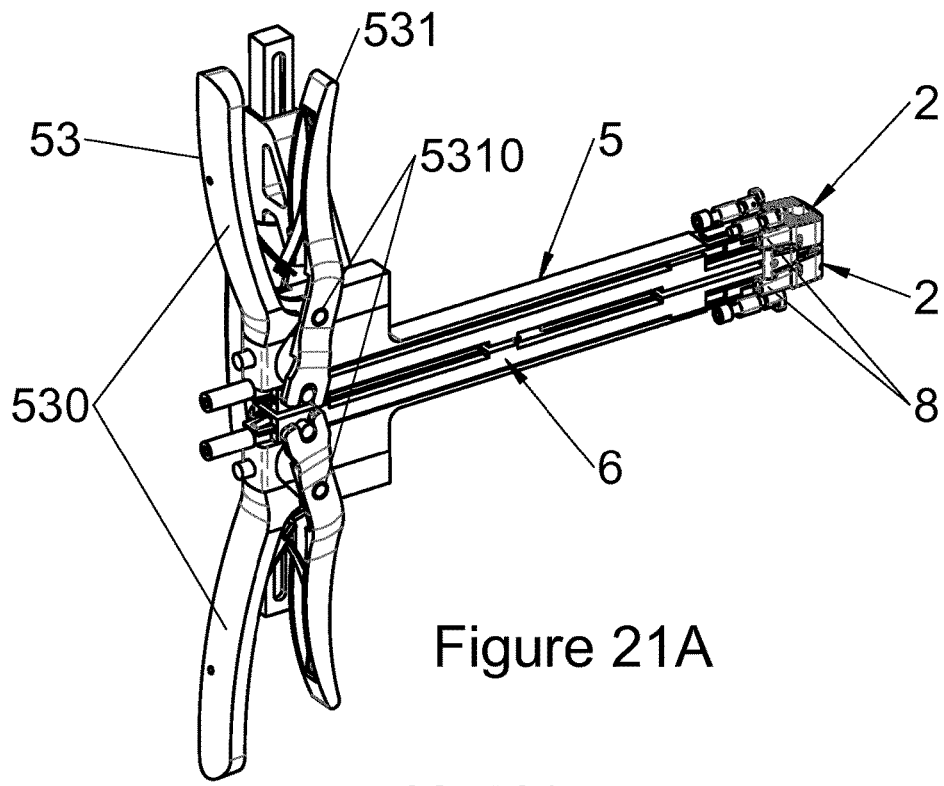
Figure 21B:
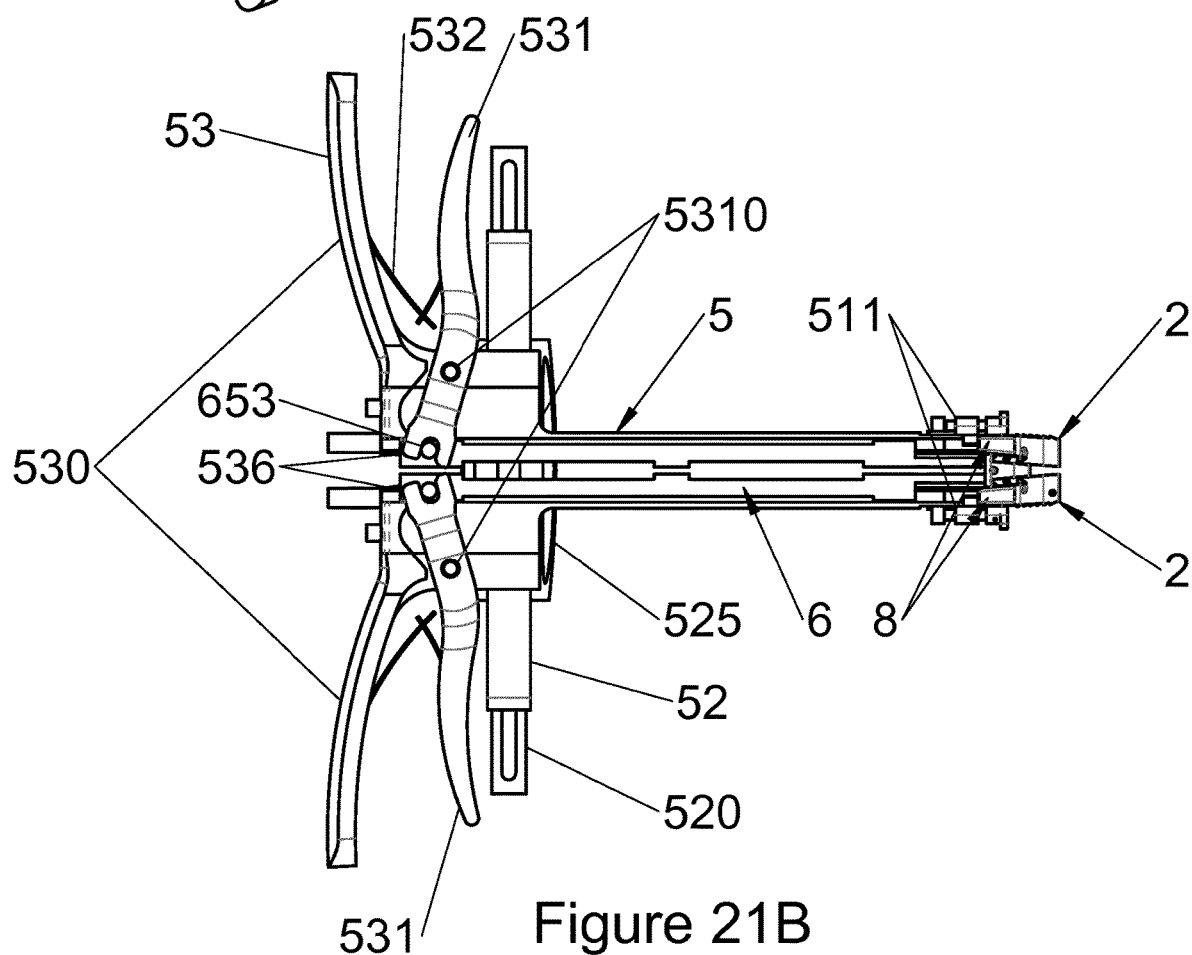
Figure 22A:
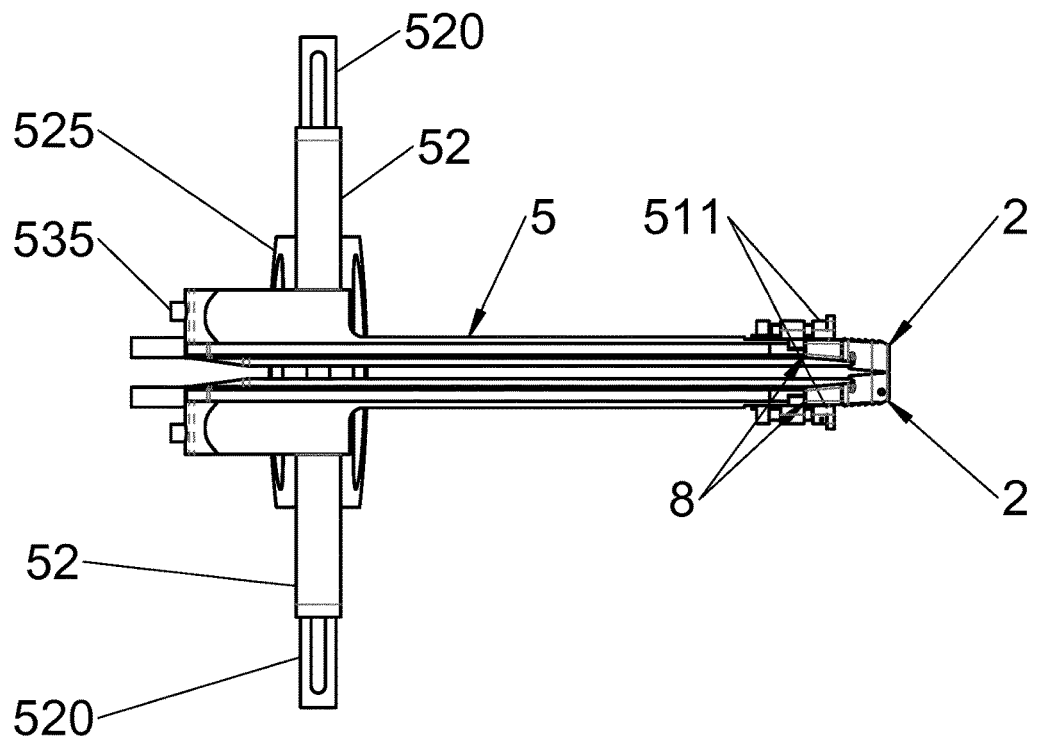
Figure 22B:
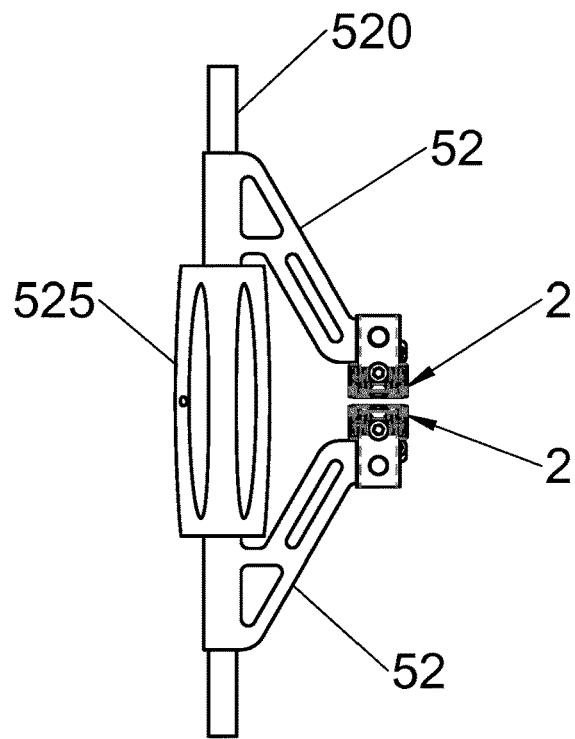
Figure 23A:
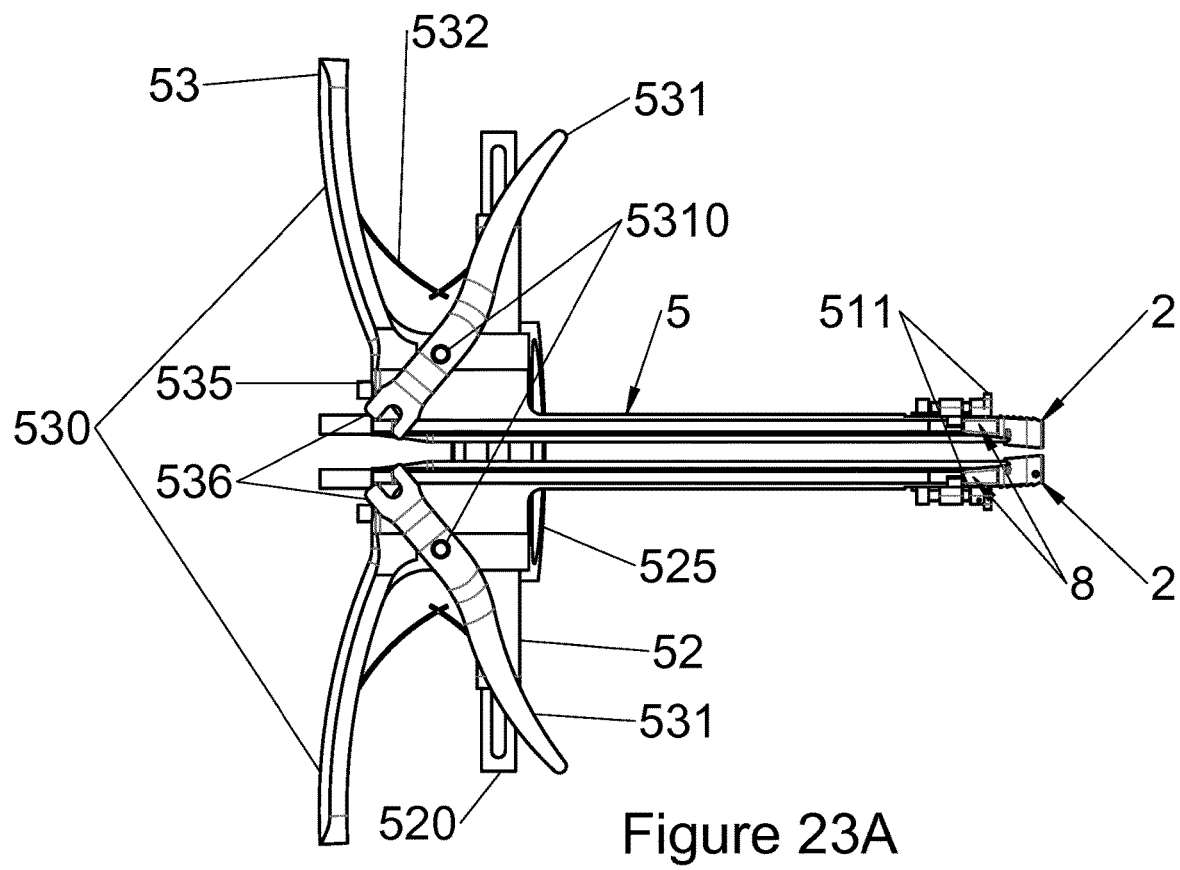
Figure 23B:
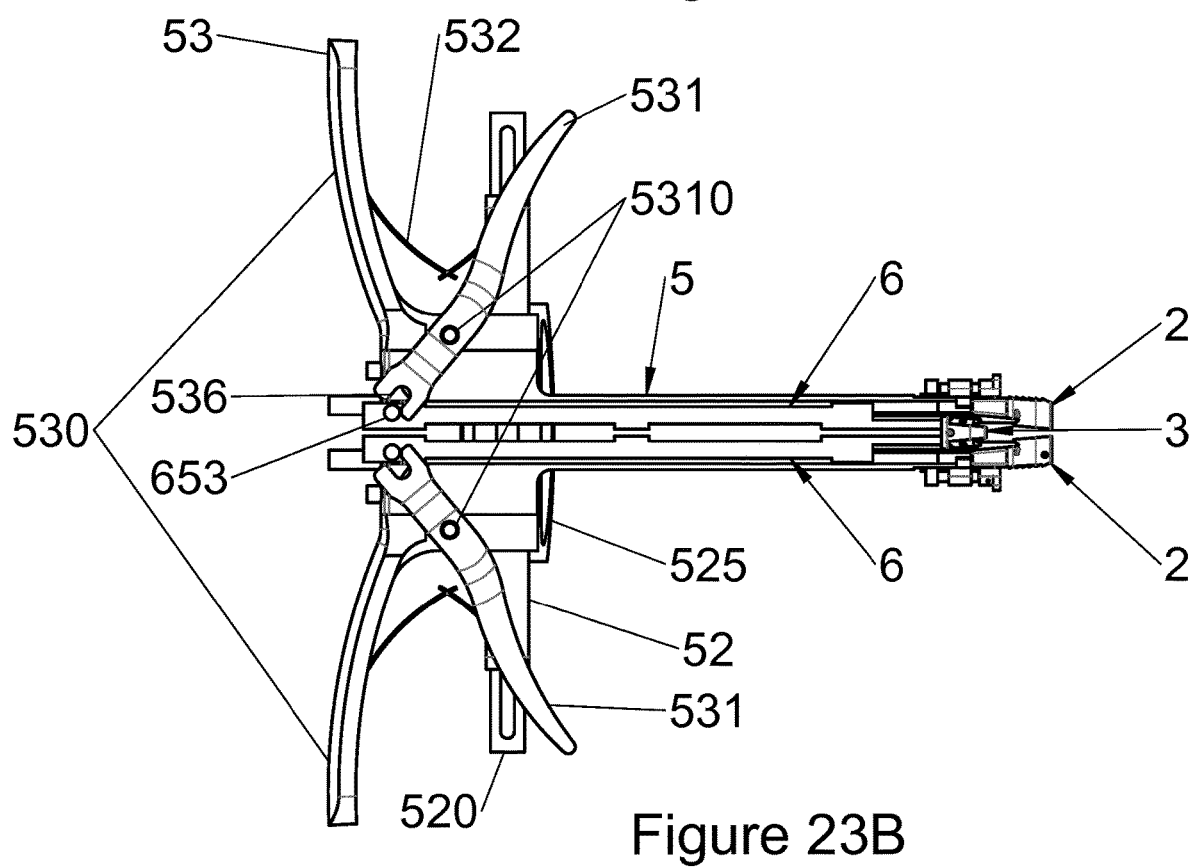
Figure 24A:
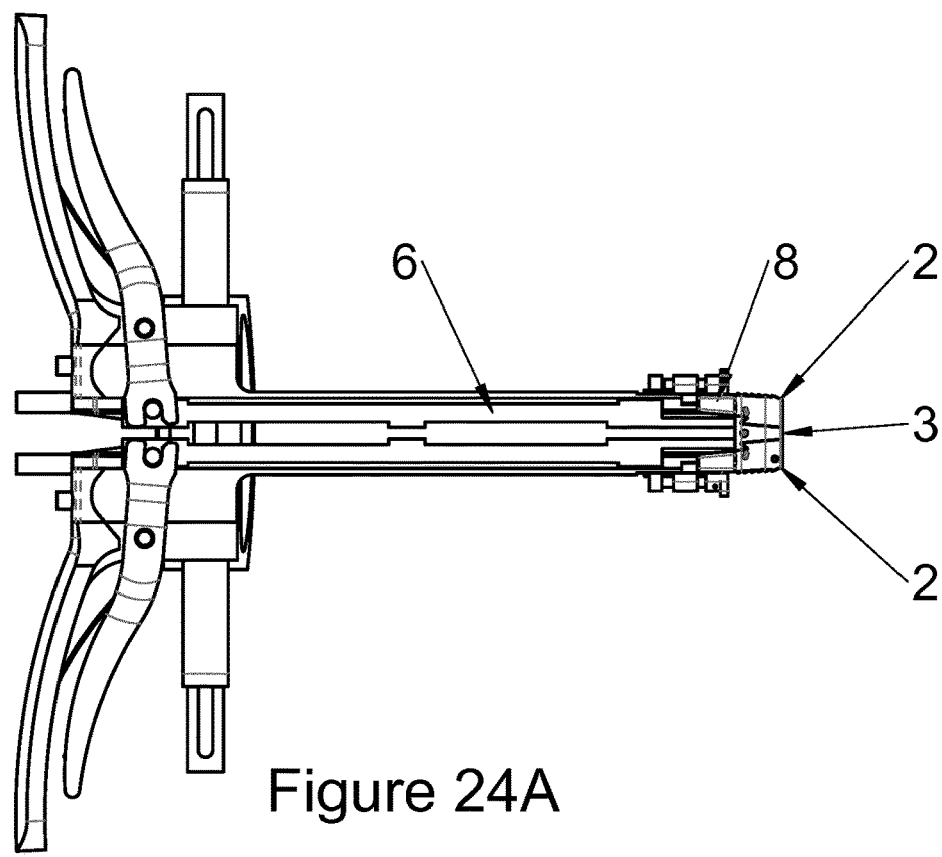
Figure 24B:
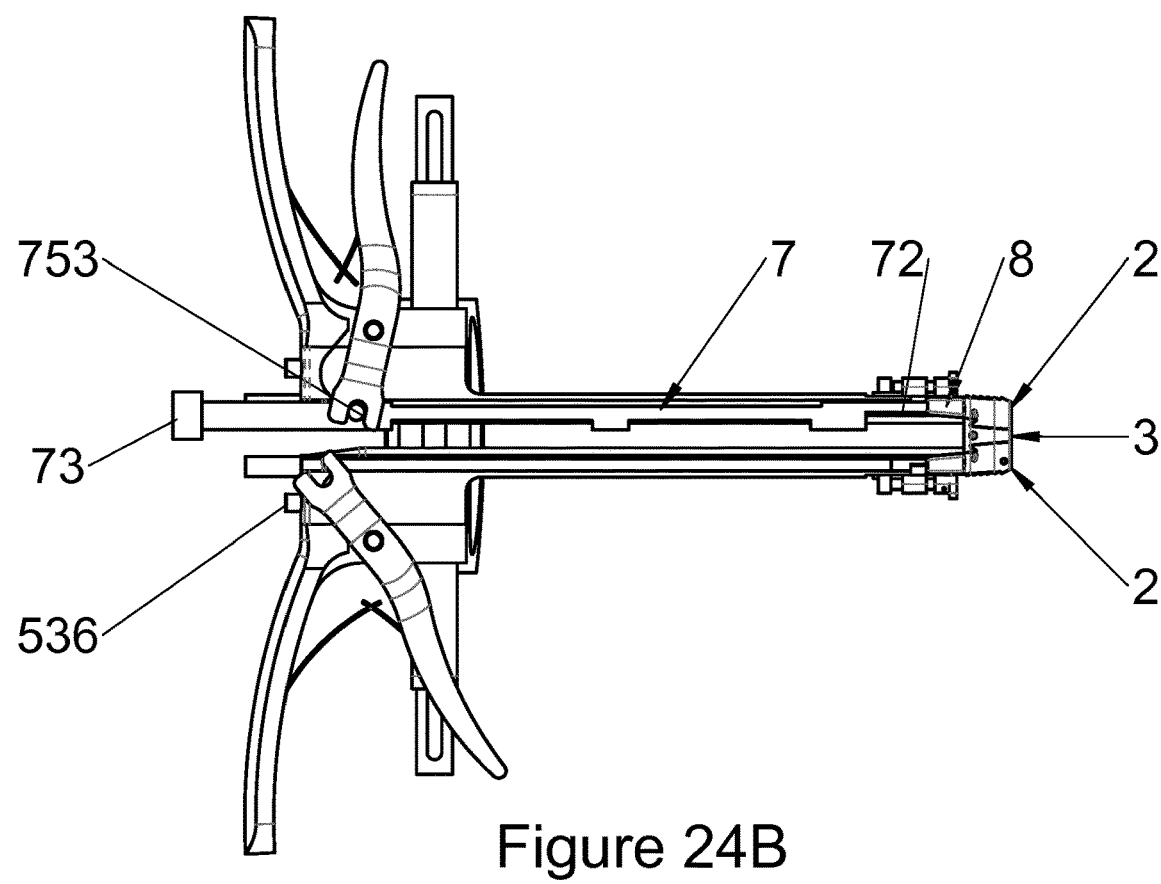
Figure 25A:
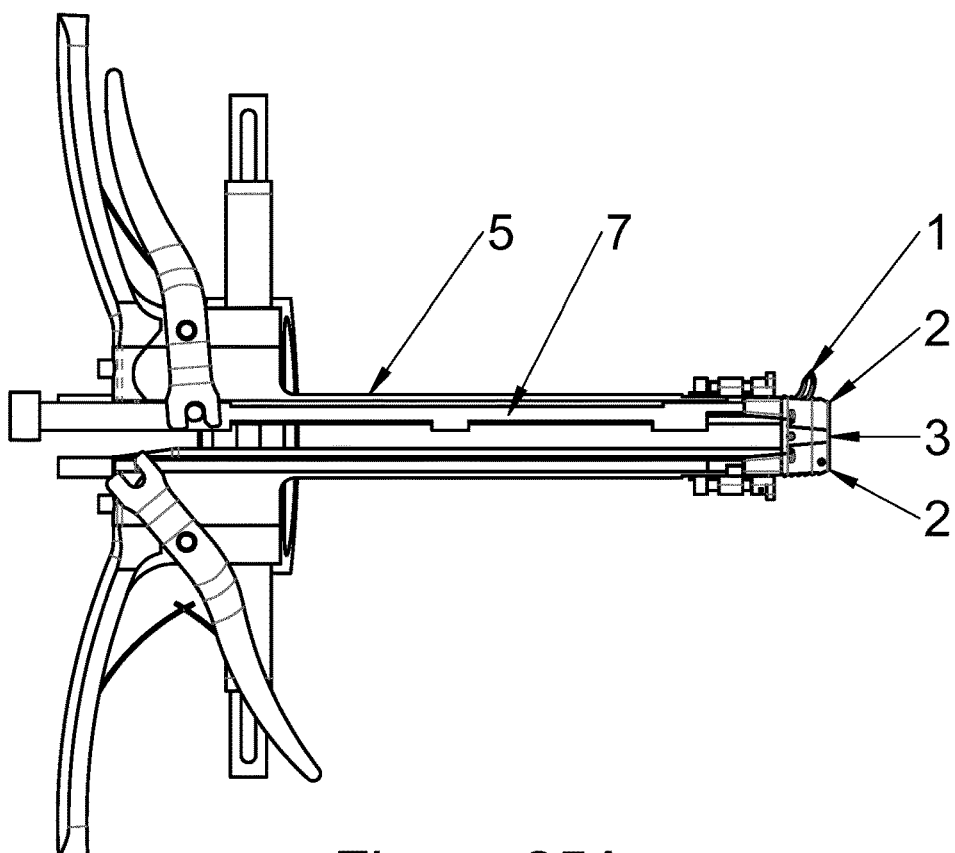
Figure 25B:
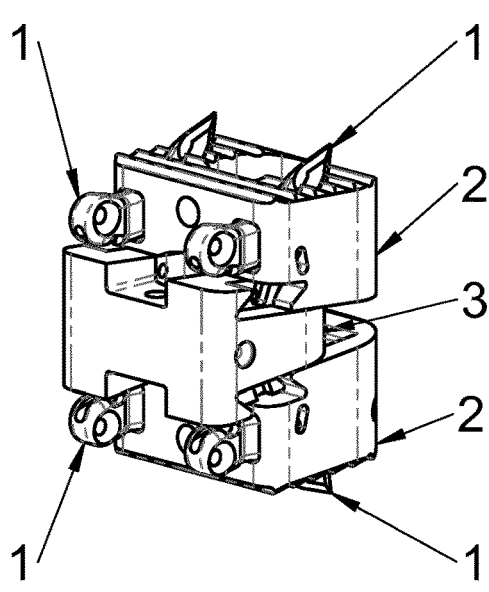
Figure 25C:
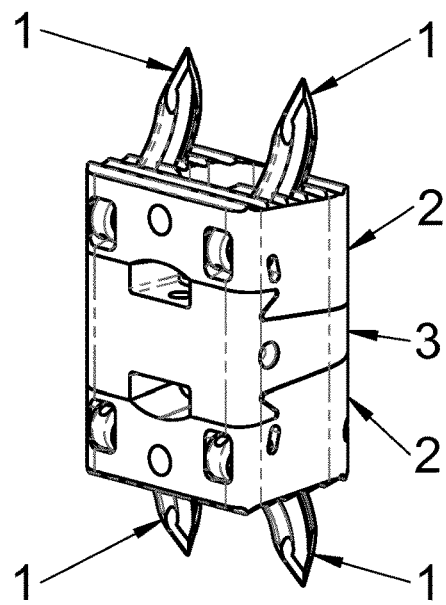
Figure 26A:
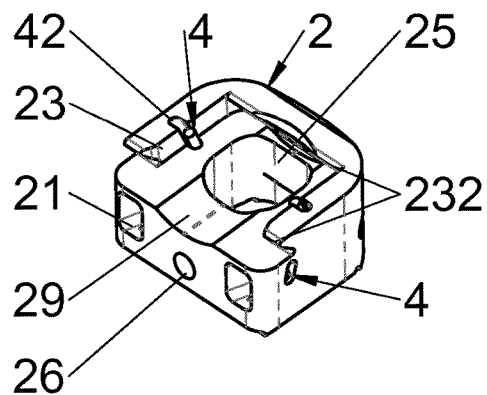
Figure 26B:
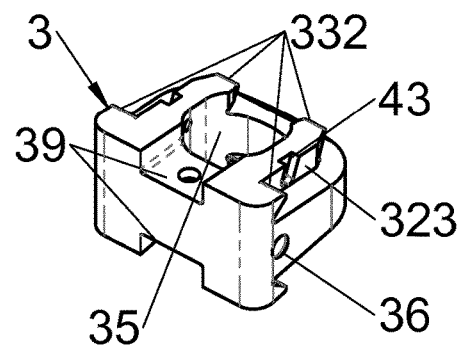
Figure 26C:
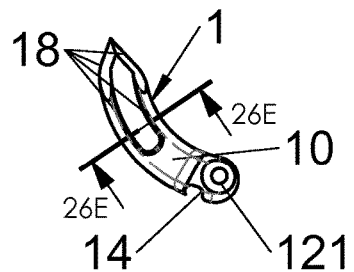
Figure 26D:
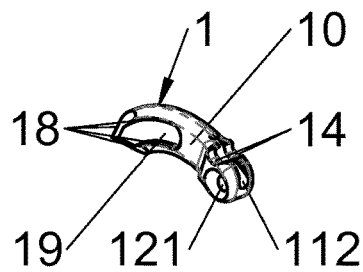
Figure 26E:
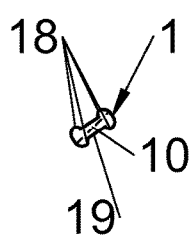
Figure 26F:
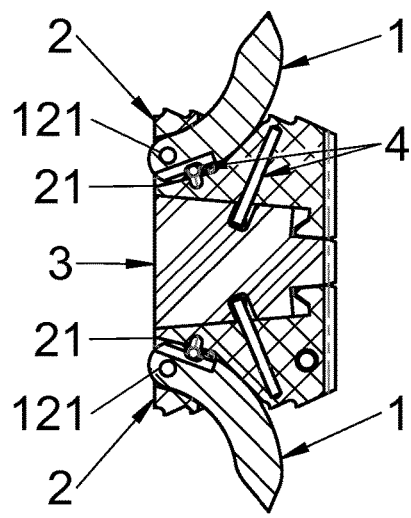
Figure 26G:
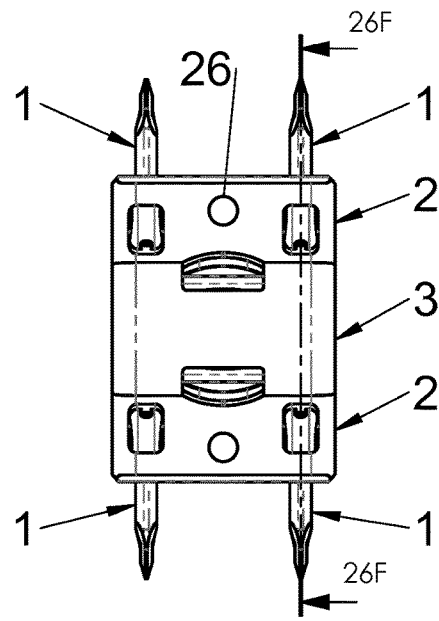

FIGS. 14A, 14B and 14C illustrate perspective views of a shim holder respectively, alone, with the shim and with a tool for attaching the shim, according to various embodiments, FIGS. 15A and 15B, illustrate profile views of an implant holder, respectively before and after distraction by inserting a shim of the implant with a shim holder according to various embodiments, and FIG. 15C illustrates a perspective view of an impactor according to various embodiments;

FIGS. 16A and 16B, illustrate profile views of an implant holder, respectively, before and after impaction of bone anchoring devices by impactors according to various embodiments, FIG. 17A illustrates a perspective view of an implant holder equipped with a distractor according to various embodiments, FIGS. 17B, 17C, 17D and 17E illustrate profile views of this implant holder, respectively before inserting the distractor, after inserting the distractor, after inserting the distractor and after inserting the shim by the distractor;

FIGS. 18A and 18B respectively illustrate a perspective view and a profile view, of an implant holder according to various embodiments and FIG. 18C illustrates a profile view of a shim holder which may be used with the implant holder of these embodiments, FIGS. 19A and 19B respectively illustrate a partial profile view and a front view, of an implant holder according to various embodiments with, inserted therein, a shim holder alone and a shim holder bearing a shim according to certain embodiments, respectively, and FIG. 19C illustrates a sectional view along the sectional plane 190-19C of FIG. 19B;

FIGS. 20A and 20B respectively illustrate a complete profile view and a partial enlargement of this profile view, of an implant holder during distraction by a shim holder according to certain embodiments, FIG. 20C illustrates a profile view of such a shim holder and FIGS. 20D and 20E illustrate partial profile views of this implant holder upon inserting a shim by the shim holder;

FIGS. 21A and 21B respectively illustrate a perspective view and a profile view of an implant holder according to certain embodiments;

FIGS. 22A and 22B respectively illustrate a profile view before distraction and a rear view after distraction of an implant holder according to certain embodiments;

FIGS. 23A and 23B illustrate profile views of an implant holder according to certain embodiments, respectively, before and during insertion of a shim by a shim holder;

FIGS. 24A and 24B illustrate profile views of an implant holder according to certain embodiments, respectively, after inserting a shim by a shim holder and during the impaction of bone anchoring devices by an impactor;

FIG. 25A illustrates a profile view of an implant holder according to certain embodiments, after impaction of bone anchoring devices by an impactor, FIGS. 25B and 25C show perspective views of an implant having a second body and two first bodies each equipped with two fixing devices according to various embodiments, respectively during and after assembly and fixation;

FIGS. 26A and 26B show perspective views, respectively, of a first body and a second body according to various embodiment, FIGS. 26C, 26D and 26E show, respectively, a side view, a perspective view and a sectional view along the plane 26E-26E, of an anchoring device according to some embodiments, FIG. 26G shows a front view of a spinal implant comprising an assembly of two first bodies of FIG. 26A and a second body of FIG. 26B provided with anchoring devices according to FIG. 26C and FIG. 26F shows a sectional view of the implant of FIG. 26G according the section plane 26F-26F.

Figure 27A:
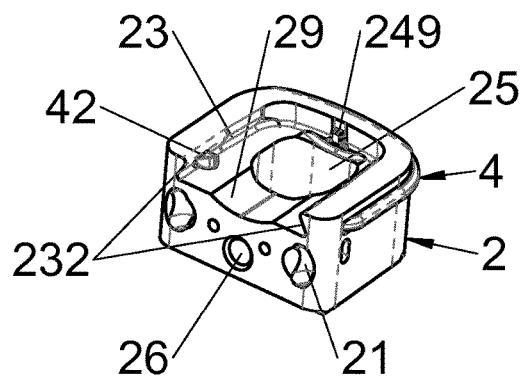
Figure 27B:
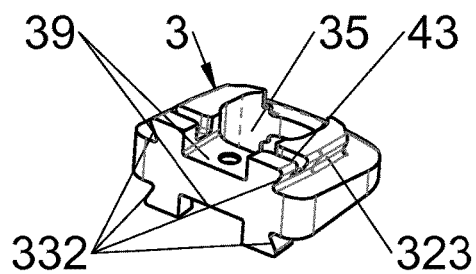
Figure 27C:
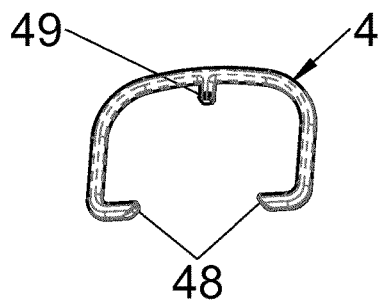
Figure 27D:
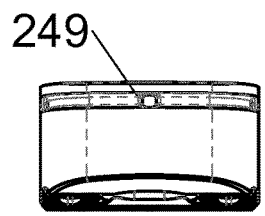
Figure 27E:
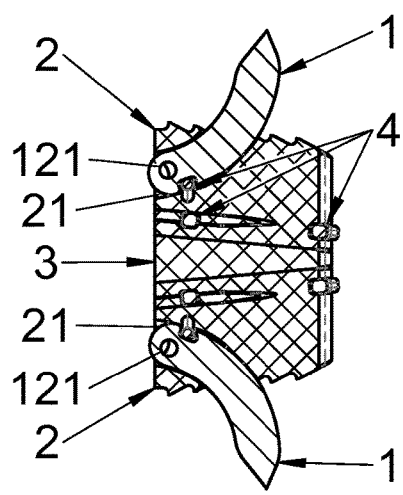
Figure 27F:
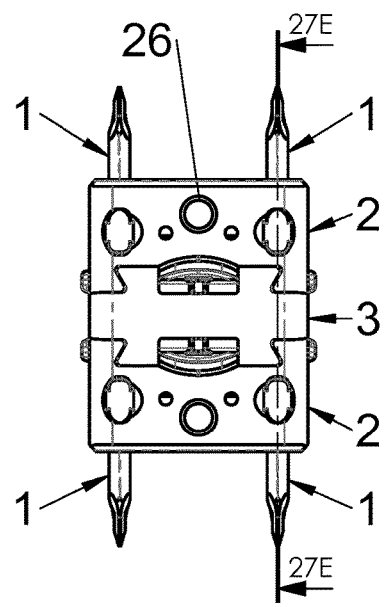

FIGS. 27A and 27B show perspective views, respectively, of a first body and a second body according to various embodiment, FIG. 27C shows a perspective view of a locking means according to certain embodiments, FIG. 27D shows a rear view of a first body of FIG. 27A, FIG. 27F shows a front view of a spinal implant comprising an assembly of two first bodies of FIG. 27A and a second body of FIG. 27B, and FIG. 27E shows a sectional view of the implant of FIG. 27F according the section plane 27E-27E.

Figure 28A:
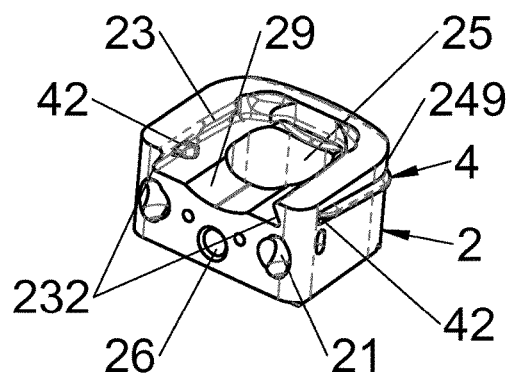
Figure 28B:
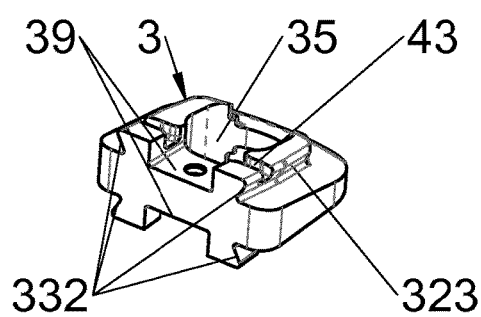
Figure 28C:
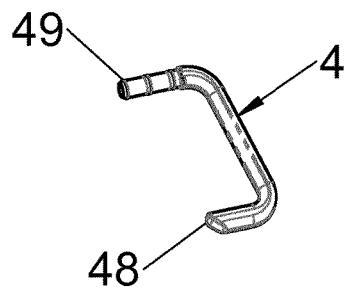
Figure 28D:
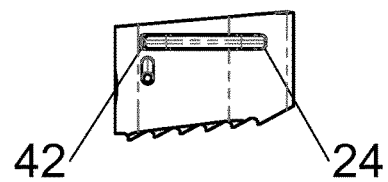
Figure 28E:
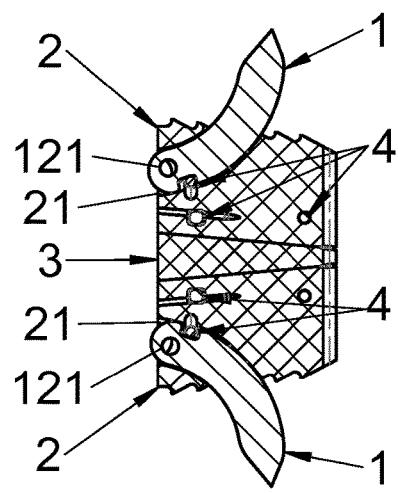
Figure 28F:
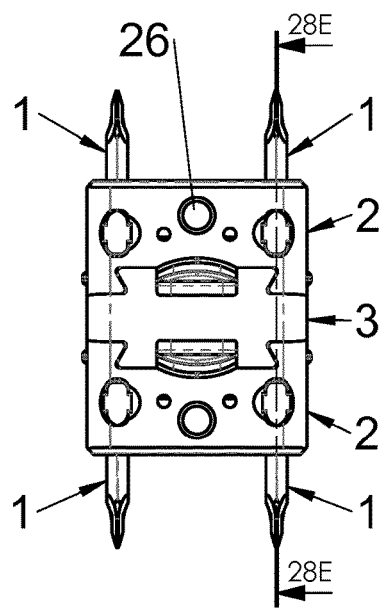

FIGS. 28A and 28B show perspective views, respectively, of a first body and a second body according to various embodiment, FIG. 28C shows a perspective view of a locking means according to certain embodiments, FIG. 28D shows a side view of a first body of FIG. 28A, FIG. 28F shows a front view of a spinal implant comprising an assembly of two first bodies of FIG. 28A and a second body of FIG. 28B, and FIG. 28E shows a sectional view of the implant of FIG. 28F according the section plane 28E-28E.

DESCRIPTION OF PREFERRED EMBODIMENTS OF THE INVENTION

The present application relates to vertebral implants, for example for corpectomy involving ablation of a vertebral segment and insertion of an implant replacing the removed tissues. The present application also describes various bone anchoring means (or attachment devices) for implants in general, for example of the type of those of the present application. These attachment devices are also designated in the present disclosure with the terms of "anchor" or "anchoring" or further "attachment means". The present disclosure also relates to implantation instrumentation for inserting an implant and to instrumentation for attaching implants. The term of "vertebral segment" is used in the present description in its generally accepted meaning of "a portion of the rachis" since it may correspond to all or part of at least one vertebral body and/or at least one intervertebral disc. Indeed, corpectomy may concern at least one entire vertebral body, or even an entire vertebra and its adjacent intervertebral discs and may only concern a portion of a vertebral body or of several vertebral bodies, either completely or partly, or at least one portion of at least one of the adjacent intervertebral discs. For example, notably in the case of cancer diseases, a vertebral body may only be partly affected and it is possible to take advantage of the fact of preserving the healthy portion for receiving an implant. Thus, the present description teaches the attachment of the implant in a "vertebral structure" and this term is used in the present description in its generally accepted meaning of "at least one portion of at least one constitutive element of the rachis" since it may correspond to all or part of at least one vertebral body and/or of at least one intervertebral disc. The terms specified above, as well as the whole of the terms used in the present description, should therefore not be interpreted in a limiting way and it will be understood from the present application that this is generally a functional definition which is given to the described elements and characteristics. For example, the term of "vertebral implant" may be used for designating the fact that the implant may concern a vertebral segment, i.e. at least one vertebral body and at least one intervertebral disc. The implant may therefore correspond to a corpectomy cage but also to an intersomatic cage, for example. Further, the vertebral attachment devices, allowing attachment in a "vertebral structure", may be used for attaching various types of vertebral implants, notably corpectomy cages, intersomatic cages, discs prostheses or osteosynthesis plates, etc.

Various embodiments of the disclosure will now be described with reference to the figures of the present application and the discussion mainly relates to 3 groups of objects:
- anchoring device(s) (1) (or "attachment device(s)" or further "anchor(s)"), and/or anchoring system(s) including several anchoring devices (1) which may be identical or different, or even complementary to each other;
- vertebral implant(s), for example corpectomy cage(s) or intervertebral cage(s) such as intersomatic cage(s), including for example implants laid out for receiving one or more of such anchoring devices (1) or systems;
- instrumentation(s) (5, 6, 7, 8, 9) for implanting these implants, for example with attachment by such anchoring devices (1) or systems.

Each of these groups of objects may include various possible embodiments, relating to a given object. Each of the objects includes various elements (generally constituents of the object) characterized by at least one technical feature. Each object (of a given group) concerned by at least one technical feature may be associated with at least one other object (of the same or of another group), for example with regard to at least one complementary technical feature, so that the object groups share a common concept. The present disclosure may therefore also relate to an assembly comprising at least 2 of these objects, as well as to each object individually. These various elements (for example a plate, abutment, slot, chamfer, or bevel, etc.) as well as their technical features (for example curvature, orientation, length, width, height etc.), are described in more detail hereafter in the present application. At least one technical feature (or combination of features) for example corresponding to an element of a given object generally solves at least one technical problem, for example from among those mentioned in the preamble of the present application. The present application therefore describes various embodiments or configurations for each object or group of objects (by specifying at least one technical feature of at least one element). It will be understood upon reading the present application that each of the technical features of each element, described in at least one embodiment or configuration, may be isolated from the other features of the relevant object (or of the relevant and/or associated objects) by said embodiment or said configuration (and therefore relating to the same element or to a different element) and/or may be combined with any other technical feature described here, in various embodiments or configurations, unless the opposite is explicitly mentioned, or that these features are incompatible with each other and/or that their combination does not work. Indeed, the structural adaptations which may be required by such isolations or combinations of features may be directly derived from the appreciation of the functional and structural considerations provided in the present application. Also, although certain technical features are discussed here with reference to the anchoring device, they may be incorporated into various embodiments or configurations of the anchoring systems. Generally, the specific technical feature(s) relating to a given element should not be considered as exclusive of those relating to another element, except when it is clearly apparent that the combination is impossible or non-functional, although the present application details various embodiments or configurations (including preferred embodiments), its spirit and its scope should not be limited to the given examples.

Various embodiments relate to a vertebral implant, for example for corpectomy, intended to be inserted into the rachis along at least one approach route for replacing a vertebral segment. This implant extends, along a vertical axis between upper and lower surfaces of the implant each intended to be placed in contact with an upper and lower vertebral structure, respectively, of said vertebral segment. In a particularly useful way, the implant includes at least one first body (2) and at least one second body (3) each having at least one face with shapes and dimensions mating those of at least one face of another body (3, 2) and forming mutual fitting means of said bodies (2, 3) for their assembling. Such assembling will generally be performed by sliding the elements (bodies) along a sliding axis which is generally not parallel to the vertical axis. However, bodies slidably assembled so that the implant can be expanded by sliding the body parallel to the vertical axis are know from the prior art and the locking means of the present application can also apply to such arrangement, so as to easily and reliably lock the vertically sliding bodies when the desired size (height) of the implant is reached. Is such cases, the locking means may have dimensions larger than locking means locking the sliding not parallel to the vertical axis, because the forces applied around the vertical axis are generally stronger. The implant may therefore include at least two bodies (2, 3), but it is generally preferred to use at least three bodies, so that the first two bodies (2) are each placed in contact with a vertebral structure and that a third body (3) is inserted between the first two bodies by means of their respective mating faces. Thus, the first bodies (2) may be designated in the present application by the term of "plate" or "end member", while the second bodies (3) may be designated in the present application by the term of "shim" or "spacer". It is understood that provision may be made for more than three bodies and that the shims will in this case also mate each other for allowing assembling by stacking the various elements. Thus, a distinction is made between the end bodies or (members) (2) or (plates), intended to be in contact with part of the vertebral segment, which should have a vertebral contact face and a face for assembly with another body (whether this is also an end body or an intermediate body), on the one hand, and the intermediate bodies (3) (shims or spacers) which should have two faces for assembly with other bodies. This type of layout facilitates implantation and allows the various bodies of the implant to be assembled together during the implantation, which is notably useful because of the distraction of the vertebral structures required by any rachidian implantation. The mating faces of the bodies (2, 3), typically have complementarity, form fitting means (23, 223, 323, 232, 332) allowing assembling (and detailed later on in the present application). This sliding axis will preferably be substantially perpendicular to the vertical axis, so that it is easier to assemble the bodies during implantation, but diverse orientations are possible. Further, the mating faces of the bodies generally correspond to their upper and/or lower faces, as illustrated on most figures of the present application, but it is possible to provide assembly by mutual sliding along side faces of the bodies. However, it is preferred to have at least one portion of the bodies slide relatively to each other on their upper and/or lower faces for facilitating implantation because of the distraction of the adjacent vertebral structures. Thus, the plates (2) or the shim(s) in contact with these plates will preferably slide on these upper and/or lower faces, but if the implant includes other additional intermediate shims (3), preference will not necessarily be given to having them slide on the upper and/or lower faces since the advantage regarding distraction will have already been obtained with sliding of the plates (2). The vertebral implant preferably includes at least one locking means (4) retained in at least one housing/recess of the bodies (2, 3) and at least one abutment portion of which is laid out in order to pass from a so-called open position, allowing sliding of the assembly of said bodies (2, 3), to a so-called closed position, locking said bodies (2, 3) assembled together by the contact between at least said abutment portion and at least one abutment (42, 43) of at least one of said bodies (2, 3). The term "housing" used here may also refer to a grove or a recess or any cavity enclosing the locking means, although channel or ducts are preferred for their small size. The term "laid our" used in the present description generally means "arranged for" and usually designates a specific function. Said abutment (42, 43) of said at least one of said bodies (2, 3) is oriented not parallel to the sliding axis, as well as the abutment portion of the locking means (4) which comes into contact with it. It should be noted that the term "not parallel" may in fact mean "not along" (parallel, tangential, etc.) the travel of the anchor and/or bodies or not along the forces applied (for example when the patient moves). Furthermore, several features are described herein as being "not parallel" or "not perpendicular" to the vertical axis or to the direction of sliding of the bodies (2, 3) or of the insertion or withdrawal of the anchor and it will be understood that this should be interpreted widely (as "substantially" or "generally" not parallel or not perpendicular) because this axis may in fact refer to the forces applied and thus to the travel of the anchor within the implant. Furthermore, because this travel may be curvilinear, this designation of not parallel or not perpendicular may in fact mean not tangential or not radial, and in fact more generally mean that the feature is not oriented along the direction of insertion or withdrawal of the anchor or the bolt from the implant. Thus, at least one surface of these mating abutments is oriented so as to provide good resistance and prevent the bodies from being able to move relatively to each other, for example by a substantially perpendicular orientation to the sliding axis. In various embodiments facilitating implantation, said locking means (4) is laid out for automatically locking the bodies (2, 3) when they are placed in the final position relatively to each other, i.e. generally at the end of travel of their mutual sliding. In some of these embodiments, said abutment portion passes from the open position to the closed position elastically, by flexure and/or by torsion, by means of at least one flexible portion of the locking means (4) allowing said abutment portion to be withdrawn from the locking means (4) in the open position during the sliding of the bodies (2, 3) on the one hand and said abutment portion to elastically return to the closed position when it is found facing said abutment (42, 43) of said body (2, 3). Thus, for example, the abutment portion may jut out from one of the bodies on one of the sliding faces and be pushed back into a housing of this body when both bodies slide relatively to each other, but this portion may return to the closed position as soon as the abutment of the other body is facing it, ready to receive it. Automatic locking of the bodies (2, 3) may thereby be obtained which facilitates their assembling, notably when this assembling is carried out during implantation, for example by first inserting the first two bodies (or "plates") for providing vertebral contact surfaces, and then by subsequently inserting another body (or "shim") for providing the definitive height of the assembly, with automatic locking of the assembly facilitating the task of the surgeon.

It will be thus understood that, in many embodiments, the locking means have reduced dimensions compared to the implant. In several preferred embodiments, said abutment portion may be small compared to the size of the implant, thus improving the reliability of the implant which is less fragile than if a large abutment portion was used, by avoiding as much as possible, thanks to these reduced dimensions, any weakening of the implant by the presence of said abutment portion and said abutment in which the abutment portion is intended to be housed. Furthermore, such arrangement of small locking means may improve the reliability of the locking functions, in particular when these small locking means are housed in a recess (or housing or duct, etc) within the implant (generally housed within at least two bodies of the implant). Indeed, this provides the advantage of improving the reliability of the implant, by limiting the risk that it breaks apart because of a too large abutment portion against the abutment in which the abutment portion is intended to be housed. Moreover, only the shearing of the locking means (at or close to the abutment portion or at the abutment surface on which the abutment portion abuts) can break the locking means. Indeed, a reliable fixation is obtained by the fact that such small locking means in fact locks the bodies (and/or anchor) by a contact over portions which are larger that the abutment portions alone. For example, the locking means may rest against a portion of the body implant having dimensions larger than the dimensions of the locking means (e.g., there is more matter, for example PEEK, of the body around the locking means than the matter constituting these locking means), so that the locking means are retained by a portion of the implant which is unlikely to suffer from the forces applied by the locking means on the implant under constraints applied to the system (the anchor in particular). In particular, in many embodiments, the locking means generally only have an abutment portion, a flexible portion and an abutment, and the abutment portion is generally very small and may just comprise an abutment surface, while the flexible portion and the abutment may be larger than the abutment portion but are still small compared to the bodies (and may generally have approximately the same size). More precisely, the locking means for locking the anchor may have a length comprised between 1% and 50% of the length of the anchor, preferably between 5% and 30%, generally about 10%. In width or height/thickness, the locking means may have a size comprised between 5% and 90% of the width or height/thickness of the anchor, preferably between 10% and 50%, generally about 30%. Furthermore, these percentages may generally be divided by a factor between 1.5 and 4 when comparing the size of the locking means to the size of the implant. The same dimensions ratio may generally apply to locking means intended to lock the anchors and for locking means intended to lock the bodies of the implant. It is thus understood that these embodiments avoid the implant to be weakened by the locking means (and its associated housing, recess or conduit) within its own body and/or by the anchor (and its associated passage) through its body.

It will also be understood from various embodiments disclosed herein that the locking means (lock/bolt) is retained directly within the body of the implant, without requiring any further element for mounting the lock and/or the anchor into the implant and/or for mounting the bodies on each other (except sliding reciprocal surfaces in most cases). This provides the advantage of limiting the need for metallic or alloy elements which may induce MRI flashes and of limiting the cost of manufacture of the implant. This also provides the advantage of improving the reliability of the implant by limiting the number of assembled elements which may move in relation to each other, or even risk to disassemble, break or spread apart, under the constraints applied to them within the patient.

Figure 2A:
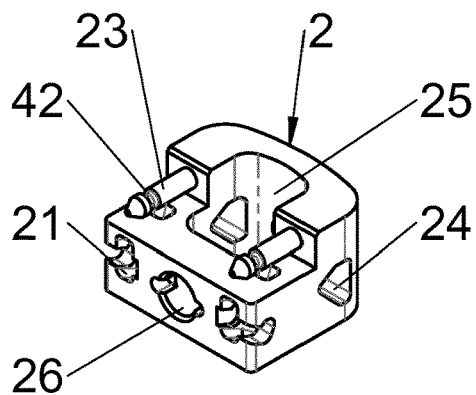
Figure 2B:
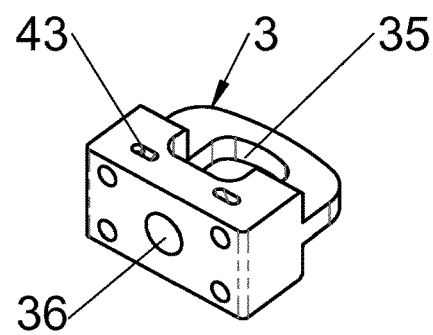
Figure 2C:
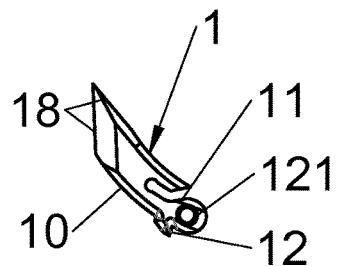
Figure 2D:
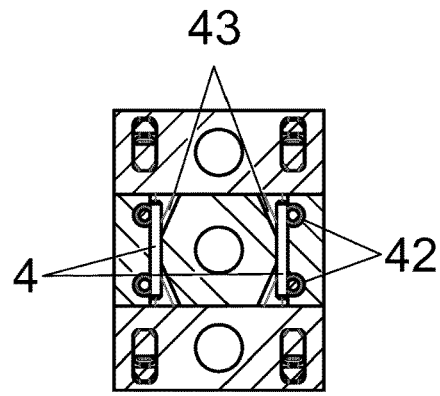
Figure 2E:
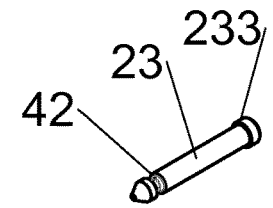
Figure 2F:
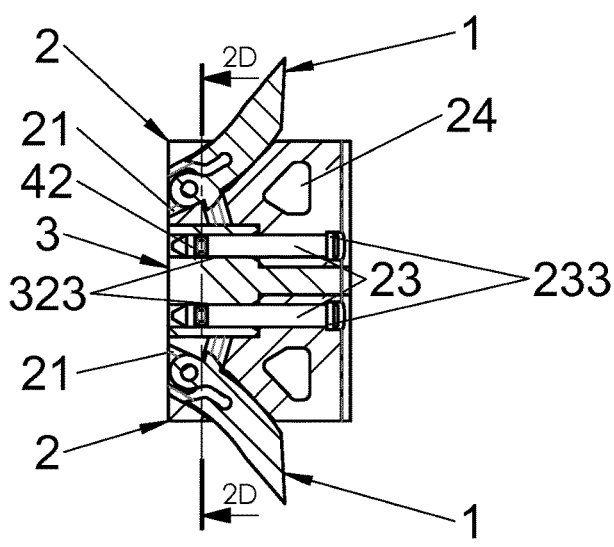

In certain embodiments, the mutual fitting means of said mating faces of the bodies (2, 3) prevent the movements of both bodies (2, 3) along at least one direction not parallel to the sliding axis. Thus, by guiding the sliding of both bodies, these fitting means prevent the bodies from being shifted relatively to each other, even under the effect of stresses to which the implant is subject and promotes stable stacking. Further, in certain embodiments, these mutual fitting means of said mating faces of the bodies (2, 3) include at least one abutment (232, 332) limiting the travel of the sliding of the bodies (2, 3) relatively to each other, for example as visible on most of the figures illustrating the implant. Thus, the assembling is assisted by the sliding which ends by an abutment facilitating proper positioning, which corresponds to the position in which the locking means (4) is in a closed position and locks the bodies (2, 3) together. Further, in various embodiments, the mutual fitting means of said mating faces of the bodies (2, 3) include at least one abutment (232, 332) inhibiting both bodies from moving away from each other in at least one direction substantially parallel to the vertical axis. This type of abutment may be obtained, for example, with substantially dovetail-shaped profiles on at least certain portions of the mating faces of the bodies (2, 3). FIGS. 4A, 5A, 6A and 6B, 7A and 7B, 8A and 8B, 9A and 9B or 11A and 11B, or further 26A and 26B show illustrative and non-limiting examples of such fitting means preventing lifting, i.e. the bodies from being moved away relatively to each other. In these examples, the mating faces including abutments (232, 332) of each of the bodies have at least one tilted surface, not perpendicular and not parallel to the sliding axis and allowing it to be fitted with a surface of the same orientation on the other body, so that the contact between these tilted surfaces prevents lifting. In various embodiments, in order to improve the fitting of the bodies (2, 3) through their mating faces, the bodies (2, 3) may for example include mutual guiding means (23, 323), facilitating the assembling of said bodies (2, 3) by sliding along a sliding axis not parallel to the vertical axis. In various embodiments, these guiding means are formed by mating surfaces (23, 323) of the bodies (2, 3), which are oriented parallel to the sliding axis, such as for example on the illustrative and non-limiting FIGS. 4A and 4B or 5A and 5B or 6A and 6B or 7A and 7B or 8A and 8B or 9A and 9B or 10A and 10B or 11A and 11B or 26A and 26B. Such guiding means may for example be at least one rod (23) of a body, for example the plate (2), intended to penetrate a mating conduit (323) of the other body, for example the shim (3), as illustrated for example in the illustrative and non-limiting FIGS. 1A and 1B or 2A, 2E and 2F or further 3A, 3D and 3E. It will be noted that these guiding means also may give the possibility of preventing the bodies (2, 3) from moving away from each other. Further, it will be noted that these guiding means (23) may have various shapes and be an integral part of one of the bodies or be separate elements retained in the body with various means such as for example a clamped fitting or even attached with diverse attachment means, such as for example screwing or a shoulder (233) as in FIG. 2E for example. It will be noted that in various embodiments, the abutment (42) of a body, intended to cooperate with the abutment portion of the locking means (4), may be formed on the fitting means, such as on the surfaces or guiding means for example. In the examples of FIGS. 2A, 2D and 2F, the locking means (4) comes into contact with a portion (42) of the guiding rods (23), while in the examples of FIGS. 1A and 1B, 3A and 3B, 4A and 4B, 5A and 5B, 6A and 6B, 7A and 7B, 8A and 8B, 9A and 9B or 11A and 11B or 26A and 26B, the abutments (42, 43) are made in (or on) the sliding surfaces. In certain embodiments, an illustrative and non-limiting example of which is illustrated in FIG. 7D, the fitting means, such as for example the sliding surfaces allowing guiding of the sliding (or the guiding rods), may include notches, teeth or irregularities (3230) with which the movements of the bodies relatively to each other may be limited, notably once the implant is assembled.

Generally, the implant preferably has suitable dimensions for replacing the treated vertebral segment and the assembling of the various bodies with each other allows adjustment of the height of the implant according to the height of the vertebral segment to be replaced. The general shape of the implant may vary according to various configurations (cylindrical, parallelepipedal configurations, etc.) and it is not necessary to detail it per se, except for the fact that it defines a vertical axis (designated here as an axis parallel to the axis of the rachis for the sake of simplicity). In certain embodiments, this is particularly useful when the vertebral structures have great irregularities (for example because the entirety of a vertebral body is not removed during the surgical operation), the implant may include additional adaptation elements to be added onto the plates or include plates of various shapes. In particular, the plates (2) may have various heights but also various widths and/or depths so as to be adaptable onto vertebral segments of various sizes. The use of such plates (2) can limit the number of shims (3) necessary for the adaptation of the implant into various vertebral segments. For example, when a vertebral segment extending over several vertebrae has to be replaced by the implant, such configuration allows shims (3) of various height to be used in combination with plates (2) of various widths and/or depths (and possibly heights), so that the implant fits the sizes of the vertebrae between which it's intended to be inserted: the upper vertebrae being smaller than the lower vertebrae in the spine. However, shims of various widths and/or depths may also be used. Further, the body may have a shape with which it is possible to impose or correct lordosis, kyphosis or scoliosis by means of upper and lower surfaces not parallel with each other, as for example represented as an illustration and not as a limitation in FIG. 11E. It will be noted that these upper and/or lower surfaces may be provided, on the whole or part of them, with notches limiting the movements of the implant for example before its attachment with at least one bone anchoring device. On the other hand, some of the implants of the present application preferably consist at least partly of PEEK (polyetheretherketone) which has physical properties, notably rigidity, close to that of bone tissues and which improves the post-operative follow-up in radiology (unlike the implants of the prior art often in titanium or in another metal or alloy which generates "MRI flashes", worsened by the fact that the implants used for arthrodesis are often accompanied by osteosynthesis plates). On the other hand, the attachment devices are preferably in a biocompatible metal or alloy, such as titanium, for guaranteeing significant strength, but other materials are possible. Further, in various embodiments, the implants include at least one first body (2) in PEEK and at least one second body (3) which is either in PEEK or in a biocompatible metal or alloy. The locking means (4) of the present application are also preferably in a biocompatible metal or alloy but other materials are possible.

As regards implantation, diverse approach routes for placing the implant are possible, even if a given route is generally preferred for each of the various rachidian stages. For example preference may be given (in a non-limiting way) to a mini-invasive approach (MIS "Mini-Invasive Spine Surgery), a median anterior approach for cervical vertebrae and a lateral or antero-lateral mini-invasive approach for thoracic or lumbar vertebrae.

In certain embodiments, the implant includes two first bodies (2) each comprising one of said upper and lower surfaces of the implant and at least one second body (3) inserted between the first two bodies (2) by means of said mating faces allowing assembling of the bodies (2, 3) by sliding. Various figures represent illustrative examples of these embodiments. Generally, the sliding axis of the bodies (2, 3) is provided substantially parallel to the intended approach route for inserting the implants into the rachis, so that the assembly of the implant may be achieved during implantation, for example by first inserting both plates (2) into the implantation space (in the place of the vertebral segment to be replaced) and then by sliding the shim (3) between the latter. In some of these embodiments, said mating faces of the bodies (2, 3) are substantially parallel to the plane(s) of the upper and lower surfaces of the implant and/or perpendicular to the vertical axis, so that the sliding of the bodies (2, 3) occurs in this plane giving the possibility of retaining a determined height of the implant. Illustrative and non-limiting examples of such embodiments are for example visible in FIG. 1A, 1B, 1E or 2A, 2B, 2E. In other embodiments, said mating faces of the bodies (2, 3) are tilted relatively to the plane(s) of the upper and lower surfaces of the implants, so that assembling of the bodies (2, 3) is accomplished by starting from their respective sides with a smaller height and sliding occurs along a tilted plane giving the possibility of restoring a determined height to the implant which is compressed in the implantation space by the adjacent vertebral structures. Illustrative and non-limiting examples of such embodiments are for example visible in FIG. 4A, 4B, 4E or 5A, 5B, 5E and the increase in height, as well as the compression, obtained are understood by comparing FIGS. 25B and 25C. It is understood that it is also possible to provide intermediate or mixed embodiments wherein one of said mating faces is substantially parallel to the vertebral contact surface, but where the other face is tilted. It will be noted that these various embodiments may facilitate the implantation and various insertion sequences are possible. For example, FIGS. 25B and 25C may suggest that the anchor (1) are inserted together with the shim, but different implantation sequences are possible and it is understood from the figures and the following description, relating to instrument, that it is generally preferred to introduce the elements one after the other. For example, it may be helpful to insert first the plates (2) into the spine and then to fix a plate by the bone anchoring means (or devices) (1), to obtain a first intermediate stabilized configuration. Then, one insert the shim (3) between the plates (2) to obtain the desired final height and finally fix the second plate to obtain the final stable configuration. However, one can also choose to fix the two plates before inserting the shim or to fix the plates only at the end, after insertion of the shim.

The present application also describes various embodiments of anchoring devices (1) which may be used with intervertebral implants, such as for example intersomatic cages (cages for replacing an intervertebral disc for achieving arthrodesis) or corpectomy cages (cages for replacing a vertebral segment for achieving arthrodesis), which are the subject of the present application, but also with intervertebral disc prosthesis (a prosthesis for replacing an intervertebral disc for preserving a certain degree of freedom of movement) or even osteosynthesis plates (plates attached onto the vertebrae for achieving arthrodesis). Other uses of the anchors (1) may of course be contemplated if the characteristics of the anchor comply with the functional parameters provided in the present application. The intervertebral implants are generally intended to be implanted between two adjacent vertebrae of the spinal column (rachis) or for making a junction between two vertebrae, at their periphery in the case of osteosynthesis plates (which may be used alone or associated with an intersomatic cage for example). The anchoring device (1) is intended to be anchored in one of the vertebrae so as to attach the implant on/against this vertebra. Various embodiments of anchoring devices (1) may include at least one rigid plate, preferably a curved plate (but not mandatorily), laid out for penetrating into a vertebra through an implant in order to retain this implant against this vertebra. The technical characteristics of "curvature" and of "rigidity" relating to the "plate" element of the "anchor" object are described in more detail hereafter. The device (1) for anchoring an intervertebral implant (2) in the vertebrae is sometimes designated in the present application under the term of "anchor" (1) with reference to its anchoring function, without inducing any limitation.

In various embodiments, the anchor (1) includes a body comprising at least one plate (10), preferably a rigid plate, elongated along a longitudinal axis. This longitudinal axis of the anchor (1) extends between a first end, designated here as an "anterior end", intended to penetrate into a vertebra and a second end, designated here as a "posterior end". It will be noted that the "posterior" and "anterior" designation of the ends of the anchor (1), of the implant and of the instrumentation are used in the present application with reference to the direction along which the implant is inserted into the rachis (the "approach route" as detailed in the present application), which is generally the same direction as the one used for inserting the anchor (1). Thus, for the anchor (1), the first so-called anterior end is the one intended to be inserted first and intended to penetrate into a vertebra for attaching an implant. As regards the implant, its wall or its end designated as posterior is the one including an opening of a passage for inserting the anchor, whether this wall is actually posterior to the implant or not during its deployment. In the case of corpectomy cages, but also for intersomatic cages or disc prostheses or plates described in the present application, this posterior end may actually be positioned towards the rear of the patient or not, notably for the cages which are essentially intended for an implantation via a posterior or transforaminal route. As regards the instrumentation, the so-called anterior end is the one intended to abut upon the implant (or is at least the closest thereto) during implantation.

Certain embodiments of implants, including certain embodiment details of the present application and relating to an intersomatic cage, are laid out for insertion into the discal space via a transforaminal route and the posterior end will therefore be positioned on a lateral and rear side of the vertebrae while the anterior end will be positioned in proximity to the opposite front and lateral side. Nevertheless, the terms of "anterior" and "posterior" are used here anyway since they are more easy to understand from a point of view of the implantation and may be used in a practical and common way with the anchor (1), with the implant, with the instrumentation, regardless of the selected implantation route (approach route). Therefore the terms of "anterior" and "posterior" are not intended to simply refer to the patient or to one of his/her anatomic characteristics, but to the direction of insertion of the anchor into the implant (regardless of whether this implant is itself implanted along an antero-posterior axis or not. On the other hand, by the terms of "height" and "thickness" are generally designated here the dimensions of the elements along an orientation parallel to the axis of the rachis (once implanted therein) and the terms of "upper" and "lower" (or above and below) are generally also defined according to this orientation (vertical when the patient is standing), without any limitative implication for this disclosure. Also, the terms of "vertical" and "horizontal" are used in a non-limiting way with reference to the axis of the rachis by considering the standing patient. On the other hand, by the terms of "width" and "length" are designated dimensions along a plane perpendicular to the axis of the rachis (a transverse plane), with the width generally being in the medio-lateral direction while the length will be in the antero-posterior direction, without this standard definition having any limiting implication for this disclosure. It will also be noted that reference is made here to a longitudinal axis between two ends and that this longitudinal axis possibly corresponds to an antero-posterior axis of the anchor (1), but that this axis is in fact oblique generally since the anchor is often inserted from the periphery of the rachis into a vertebral structure (a vertebral body most often and generally in a vertebral plate). Further, this axis of the anchor even follows a curved path in many embodiments and may therefore designated as antero-posterior relatively to the ends of the anchor rather than with reference to the rachis. Also, the axis of the passage may be designated by using the same references when it is oblique and when it may be curvilinear or rectilinear. It will also be noted that this definition may also be extended to the implant and to the instrumentation, generally with reference to the direction of insertion of the anchor (1) and/or of the implant. It will also be noted that the term of "approximately" or "substantially" is regularly used in the present description, notably relating to a characteristic such as an orientation or a direction, so as to indicate that the relevant characteristic may in fact be slightly different and not be exactly as designated (for example, the expression "substantially perpendicular" should be construed as "at least approximately perpendicular" since it may be possible to select an orientation which is not exactly perpendicular in order to be nevertheless able to substantially fulfill the same function). Further, terms such as "approximately" may also be used for or apply to the technical characteristics that may be "in general" ("generally"), and often "preferably", as indicated, but other embodiments or configurations may be within the scope of the present disclosure.

At least one portion of the bodies (2, 3) of the implant according to various embodiments includes at least one abutment (42, 43) (sometimes limited to a single surface) mating an abutment portion (or also a surface) of a locking means (or device, for example a catch, latch, clip, clamp, lock, retainer or similar structure) (4) laid out for locking the bodies (2, 3) relatively to each other. Also, in various embodiments, the anchoring device (1) includes at least one abutment (14) (sometimes limited to a single surface) mating an abutment portion (or also a surface) of a locking means (or device, for example a catch, latch, clip, clamp, lock, retainer or similar structure) (4) laid out for locking the anchor (1) relatively to the implant (or vice versa). The abutments (14, 42, 43) of the bodies (2, 3) and/or of the anchor (1) preferably comprise at least one abutment surface not oriented parallel to the sliding axis (of the bodies) and to the longitudinal axis (of the anchor), respectively, in order to efficiently oppose the movements along these axes. This (or these) surface(s) is(are) typically complementary to at least one surface (or portion) of an abutment of the locking means (4). This locking means (4) may be located on or in the implant itself. Indeed, in order to address one or more problems of the prior art, this disclosure provides various representative embodiments of novel layouts of the anchors, implants and instrumentations, by providing a locking means (or device) (4) which equips the implant itself ("equips" also meaning here that the locking means may be distinct from the implants or integrated into the latter, or even in one piece, or provided integral with the latter, although it is generally preferred that it be distinct and housed inside the implant). This locking means (4) thus provides many advantages (some of which are detailed hereafter), for example in addressing at least one portion of the problems mentioned in the present application. This locking means (4) preferably comprises a body retained in the implant and provided with at least one flexible portion and with at least one abutment (31), cooperating with said abutment (14, 42, 43), generally by means of the contact of their mating abutment surfaces. In various embodiments, advantage is taken of this flexibility for automatic locking but the present application describes other embodiments. The (spinal) vertebral implant according to various embodiments include at least one vertebral contact surface through which the implant is intended to be placed in contact with at least one vertebral surface and at least one outer surface (for example a peripheral, lateral surface or even inside the discal space, the term of "outer" being used with reference to the fact that the anchor penetrates into the vertebra from the outside of the implant while entering through this surface and passing through the inside of the implant).

It will be noted that the term of "flexible" is used for designating the fact that in some embodiments the locking means passes from a rest configuration to a bent or flexed configuration and returns to the rest position or to a position close to the rest position. The present application describes how this flexibility (or elasticity as discussed hereafter) may be obtained in various embodiments and it will be understood that this relative term finds its definition in the fact that a lock (locking means or device (4)) capable of undergoing flexure or torsion and of returning to its initial position (e.g. rest position) or at the very least approximately to its initial position is generally used (if it plasticizes, provision may be made for this being negligible for the locking function). Further, it is generally selected in a rigid and solid material capable of supporting strong stresses which may be exerted thereon when the bodies (2, 3) and/or the anchor (1) are locked. Thus, preferably a locking means in a biocompatible material such as in titanium for example, is preferred and an alloy is generally used. In order to provide the intended flexibility, one therefore acts upon the elasticity of a portion of the lock, i.e. it is provided so that it does not (or only very little) exceed its elasticity limit in order to avoid irreversible deformation (being accompanied by a failure for a fragile material or by plastic deformation for a ductile material). Therefore it is understood that the term of flexibility may be used here in the sense of elasticity by preferably providing that it remains in values below the elastic limit of the lock or similar structure, for example by resorting beforehand to buckling, creep, compression, torsion, flexure, and/or shearing measurement steps etc. Conversely, an anchor (1) of various embodiments also may be designated as being preferably "rigid" or "stiff" since it is generally preferred that a bone anchoring device (1) should not deform when it is inserted into the implant and/or planted into the vertebrae, in order to improve the reliability of the system by limiting risks of play of the anchor (1) in the vertebra and of non-desired withdrawal. These terms of "rigid" and "stiff" which are relative terms will therefore be understood by one skilled in the art in their functional definition covering all materials and/or layouts while avoiding as much as possible too large flexibility or elasticity, as well as the risks of buckling, creep, compression, torsion, flexure, shearing, etc. Further, this relative flexibility of the locking means (4) is generally allowed in many embodiments by the sufficiently thin dimensions of the flexible portion and by the fact that the lock may be retained or secured (or held fixed or in one piece) onto the implant on a portion and that the portion(s) forming the abutment(s) have a possibility of displacement in the implant, by the fact that beyond the retained or secured portion of the implant, the other so-called free portions, of the locking means (comprising the flexible portion and the abutment) have at least one degree of freedom (not parallel to the axis of the anchor and of its passage in the implant), by the fact that the implant includes a housing (42, 43), the size of which at these free portions is greater than the size of these free portions providing a clearance allowing the passage from the open position to the closed position, and vice versa, for example such as visible by comparing the housing (42) of FIG. 26A with the housing (43) of FIG. 26B, or for example as shown on FIG. 26F. This layout is particularly advantageous in many embodiments and the lock is generally dimensioned according to its material in order to allow flexure/torsion with return since the lock is thereby secured in the implant. Further, in various embodiments, the free portions in the implant only have a single degree of freedom not parallel to the sliding axis of the bodies (2, 3) and/or to the axis of the anchor (1), which allows the lock (4) once it is engaged with its mating abutment (14, 42, 43) not to move in the direction of the withdrawal or advance of the bodies (2, 3) and/or of the anchor (1), thereby securing the locking.

This type of layout of at least one locking means provides many advantages in some embodiments. Indeed, the implant comprising a locking means may allow enhancement of the invasivity and/or reliability of the system, since the locking system (4) may be of reduced dimensions relatively to the size of the implant while providing a reliable lock and the anchor may be of a more reduced size than in the absence of a locking means provided in (or on) the implant. Conversely, the abutments used and especially the mutual engagement elastic (flexibility) mechanism, may be of larger dimensions, without this inducing a problem of congestion and/or invasivity of the implant and/or of the anchor. Thus, the system may be more reliable since the bodies (2, 3) and/or the anchor (1) may be effectively locked with abutments of satisfactory dimensions, for example greater than those known from the prior art. Indeed, in many embodiments and/or deployments it may be important to provide an effective locking means since the bodies and/or the anchors may be retained only by this mechanism, unlike other known anchoring devices of the prior art (which addresses the problem of reliability and has many additional advantages, such as cost and simplicity for application for example). Thus, in may embodiments of the present application, a locking means with suitable dimensions and layout is generally provided for undergoing significant stresses, as detailed in the present application.

Figure 5A:
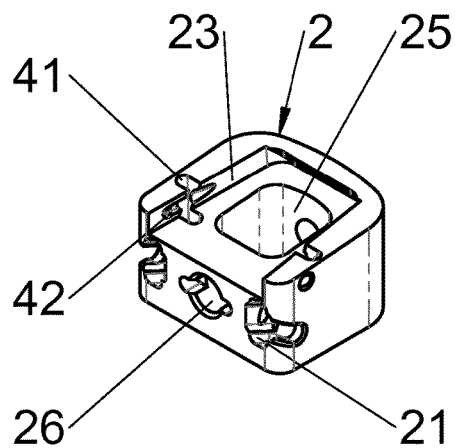
Figure 5B:
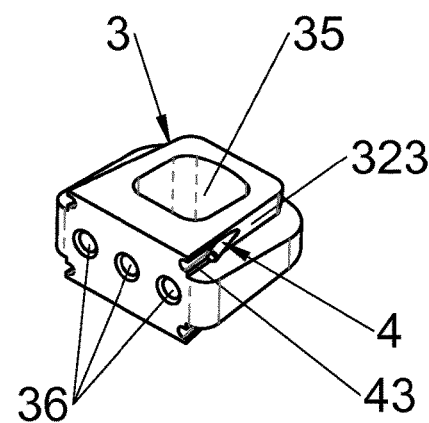
Figure 5C:
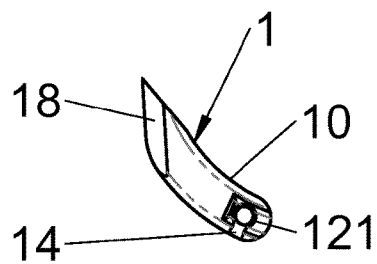
Figure 5D:
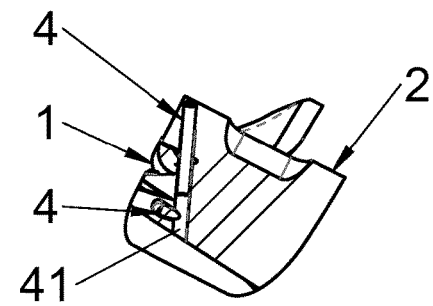
Figure 5E:
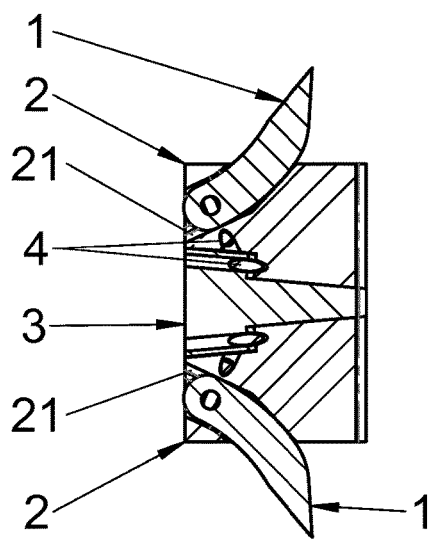
Figure 5F:
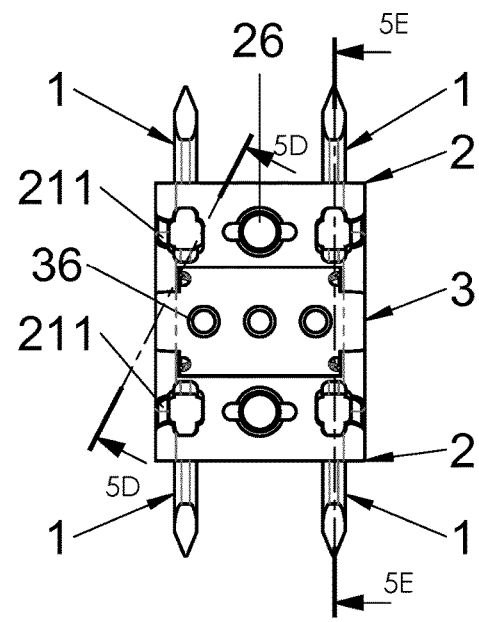
Figure 8A:
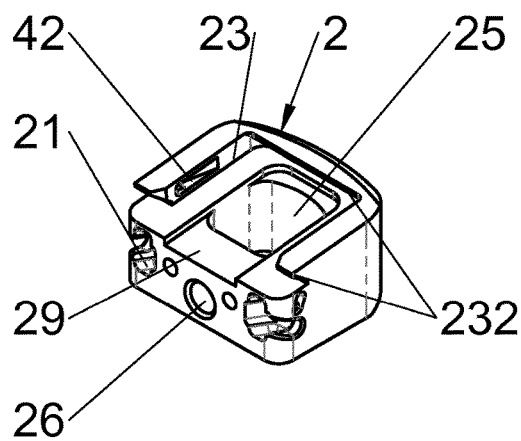
Figure 8B:
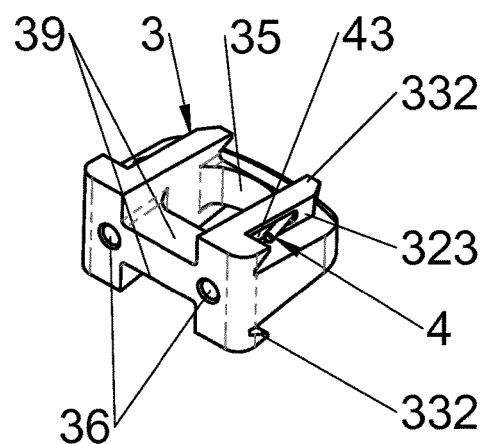
Figure 8C:
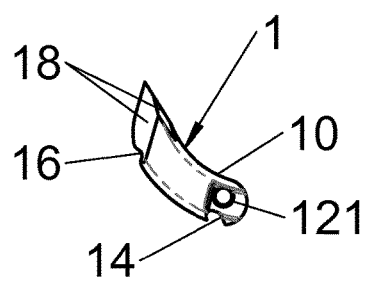
Figure 8D:
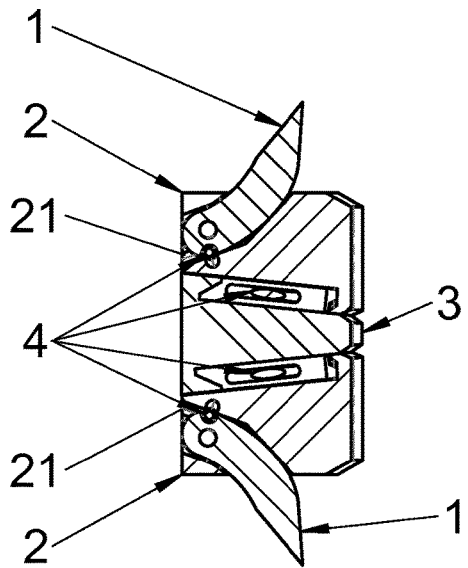
Figure 8E:
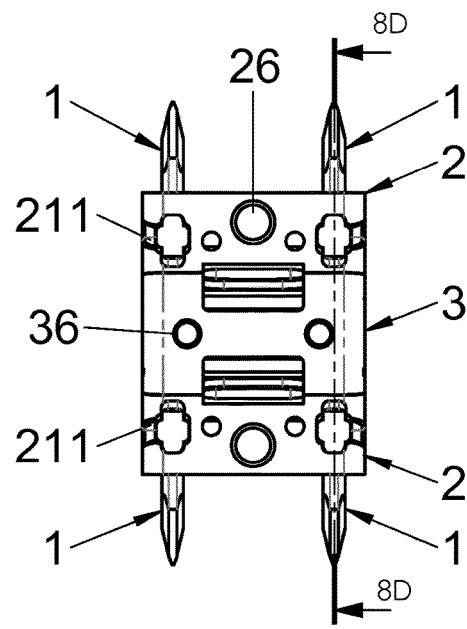

This type of layout of the locking means may also provide the additional advantage of allowing the abutments to be provided in a solid material, even if the implant is in a more flexible material. Indeed, for example, in the case of intersomatic cages or corpectomy cages, it is frequent that the material be relatively tender such as for example PEEK (acronym of polyetheretherketone). On the other hand, the bone anchoring devices generally are provided in a solid material in many embodiments, notably when they are intended to be directly planted into the bone without making any housing beforehand for receiving them therein. Thus, the use of a device in a rigid material is preferred which will support the impaction in the bone and which will provide good stability, such as for example in titanium. Thus, an anchor in a solid and often rigid material may have the risk of damaging the more flexible material of the implant if the abutments of the anchor have to bear (i.e., in abutment) against structures or surfaces of the implant. In various embodiments of the present application, this risk is limited by allowing the anchor to abut upon the locking means. Preferably, it is then provided that this locking means be also itself in a solid material, i.e. a material which has a low risk of being damaged by the anchor bearing upon it. For example a locking means may be selected in the same material as the one of the anchor (for example titanium). In addition to avoiding any damage to the implant (which, depending on the extent, may jeopardize the whole system), this advantage is accompanied by increased reliability of maintaining the anchor in the implant. In certain embodiments, said abutment (14) of the device (1) is a female abutment cooperating with a male abutment of the locking means (4). For example, said abutment (14) of the device may be a recess, a notch, an opening, an irregularity or any other recessed form in a surface of the anchoring device (1), intended to cooperate with a protrusion forming the abutment (31) of the locking means (3). For example, FIGS. 5C and 6C represent as an illustration and not as a limitation, such a female abutment of the anchor. Alternatively, in certain embodiments (not shown), said abutment (14) of the device (1) may be a male abutment cooperating with a female abutment of the locking means (4). For example, said abutment (14) of the device (1) forms a protrusion jutting out from a surface of the anchoring device (1) and intended to cooperate with a recess in a surface of the locking means (4). The shape of such a male means, for example forming a protrusion on a surface of the anchor, may vary, as well as the position of this male means on the anchor may also vary according to various embodiments. Also, for locking the bodies, a male abutment may be provided, jutting out from one of the bodies (2, 3) for engaging into a female abutment portion of the locking means (4). Nevertheless, it is generally preferred to provide a female abutment in the body (2, 3) for receiving an abutment portion of the locking means (4). Indeed, the solid locking means generally will better support the stresses in spite of its small dimension relatively to the implant and therefore it is generally preferred that the locking means form a male means received in a female abutment (42, 43) of the bodies (2, 3) so that the dimensions of this abutment, larger than those of the locking means (4), limit the risks of deformation of the flexible material of the bodies (2, 3) in contact with the solid lock (4).

This type of layout may also allow a single and same locking means to provide two different types of abutments. Indeed, it is possible to provide a single abutment surface in order to oppose the movement of the bodies (2, 3) and/or of the anchor (1) in a single direction (the direction of the sliding for assembling or disassembling, or the direction of penetration into the implant and the vertebra or the direction for taking the anchor out of the implant or the vertebra) or to provide two opposite surfaces for opposing movements in both directions. Thus, in certain embodiments, said abutment surface present on the abutment (14) of the device is oriented facing the posterior end of the anchoring device (1) so that the abutment portion of the locking means (4) gives the possibility of opposing the taking of the device out of said passage. Alternatively, said abutment surface present on the abutment (14) of the device may be oriented facing the anterior end of the anchoring device (1) so that the abutment portion of the locking means (4) gives the possibility of opposing excessive advance of the device (1) in said passage. Advantageously, both of these non-exclusive alternatives may be combined so that the abutment includes both an abutment surface oriented facing the posterior end of the anchoring device (1) and an abutment surface present on the abutment (14) of the device is oriented facing the anterior end of the anchoring device (1). Thus, the locking means (4) gives the possibility of opposing both involuntary removal and excessive advance of the anchor. It is then possible to provide that the respective abutments of the anchor (1) and of the locking means (4) oppose the advance and/or removal of the anchor. Of course the same applies to the bodies (2, 3) and the travel of their mutual sliding may thus be limited. Thus, it is possible to do without means limiting the travel of the anchor in the implant and/or the sliding of the bodies relatively to each other, even if it is generally preferred in some embodiments to provide such means.

Another advantage is that a single and same locking means (4) may, in various embodiments, be used for locking two bodies relatively to each other but also the anchor relatively to one of these bodies, which for example is advantageous in terms of congestion and cost. Further, the layout of a single and same locking means with a flexible portion may sometimes allow simultaneous locking of a shim (3) with two plates (2) and both of these plates (2) with an anchor (1).

Figure 3A:
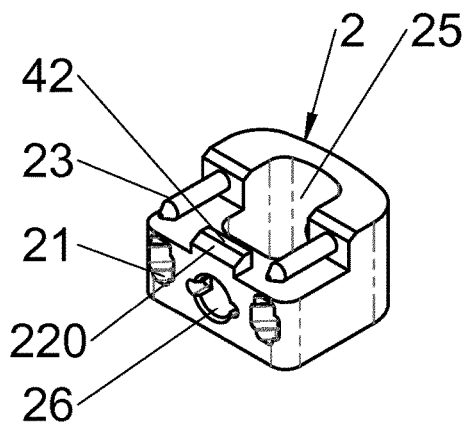
Figure 3B:
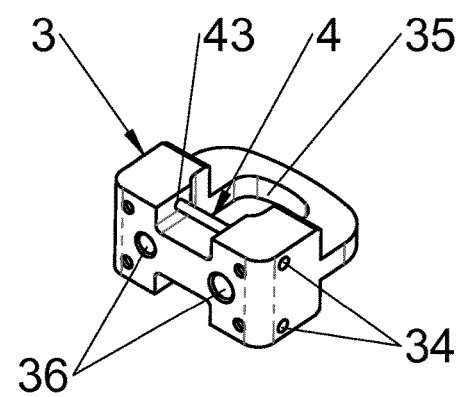
Figure 3C:
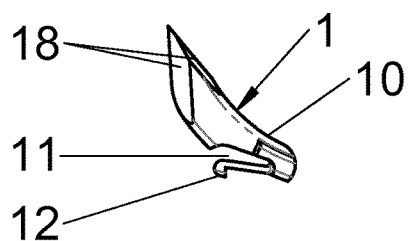
Figure 3D:
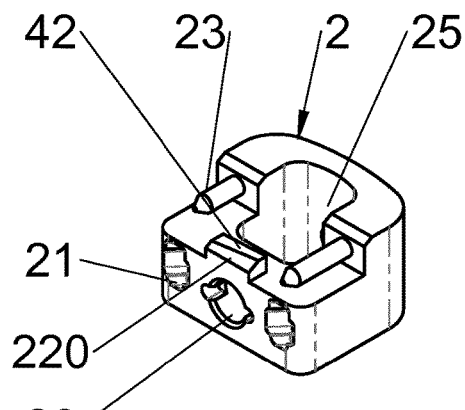

In various embodiments, a (at least one) locking means (4) is formed by a stick or a rod (4) (cylindrical or with various possible shapes) retained in a housing (42, 43), of one of the bodies (2, 3) (whether this is a plate or a shim, although most of the figures generally illustrate the lock retained in the plate). This housing is flared at the flexible portion in order to provide a displacement of the abutment portion along a direction not parallel to the sliding axis. The other body then includes a housing (43, 42) positioned facing the one in which the lock has its displacement, but over a more restricted portion corresponding to the closed position. This type of embodiment further has the advantage of great ease for application while providing reliable locking. Of course, the locking means may have other shapes, orientations or layouts and the illustrative examples provided in the present application are non-limiting. For example, in certain embodiments, said (at least one) locking means (4) is oriented substantially parallel to the vertical axis and its abutment portion moves elastically, between the open position and the closed position, along a direction perpendicular to the vertical axis and not parallel to the sliding axis, for example along a direction also perpendicular to the sliding axis (for example in a plane transverse to the vertical axis). Illustrative and non-limiting examples of such embodiments are illustrated in the figures of plates 1A, 1B, 1D, 2A, 2B, 2D, 7A, 7B, 9A, 9B, 9C, 9D, 9E and 11A, 11B, 11D. In other embodiments, said (at least one) locking means (4) (of the bodies (2, 3) for example) positioned in the closed position in a plane substantially perpendicular to the vertical axis and its abutment portion is positioned outside this plane where it is in the open position, generally by moving along a direction not parallel to the sliding axis. Illustrative and non-limiting examples of such embodiments are illustrated in FIG. 3B, either in combination with FIG. 3A wherein the lock (4) moves elastically by flexure by means of a flat surface (220) of the abutment (42) of the body (2), or with FIG. 3D in which the lock (4) moves elastically by torsion by means of a tilted surface (220) of the abutment (42) of the body (2). In other embodiments, said locking means (4) is positioned, in the open position, in a plane substantially perpendicular to the vertical axis, preferably along a direction parallel to the sliding axis, and its abutment portion is positioned outside this plane when it is in the closed position. An illustrative and non-limiting example of such an embodiment is illustrated in FIG. 7D. Preferably, in these type of embodiments, for example when the lock (4) is parallel to the sliding axis, it will be provided on the body which is intended to be inserted secondly (or lastly), i.e. on the shim (3) rather on the plate (2) in the case of three bodies, so that insertion of the bodies allows the lock to be pushed back into the open position instead of having the latter interfere with this insertion. In other embodiments, said (at least one) locking means (4) is oriented in a transverse plane substantially perpendicular to the vertical axis and its abutment portion moves elastically between the open position and the closed position, substantially in this transverse plane. Illustrative and non-limiting examples of such embodiments are illustrated in FIGS. 5A, 5B and 8A, 8B. In some embodiments, the locking means (4) are retained on the implant by being disposed in at least one groove around at least part of at least one of the bodies (2, 3) and by the abutment portion of the same or other body. For example, in some embodiments, illustrative and non-limiting examples of which are shown in FIGS. 27A, 27B, 27C, 27D, 27E and 27F or in FIGS. 28A, 28B, 28C, 28D, 28E and 28F, the locking means (4) may be disposed at the periphery of the implant, preferably within or along groove made in the periphery of the implant. Such external layout may make the locking means visible from outside the implant and allow visual control of the locking function by the surgeon during the implantation. Furthermore, such external layout may facilitate the unlocking thanks to a peripheral access (for example a groove allowing to introduce, from outside the implant, a tool between the lock (4) and the implant, or thanks to an access (29, 39) between the plates (2) and the shim (3), as described in the present application. Such external layout also may allow to limit the encumbrance of the locking means (4) within the implant and requires less recess in the implant which may be more robust and reliable. Such external layout also may allows the flexibility of the locking means (4) to rely on a portion having a larger extent than many internal layouts do. For example, the locking means (4) may be held in the implant in a portion (249) which is at the opposite side of the implant (the anterior face for example) compared to the location of the stops (42, 43) in which the stop portion of the locking means (the posterior face for example) is moving between the open and closed positions. The distance between the held portion and the locking portion of the locking means thus may allow the flexibility to span over a large portion. Thus, in some embodiments, even with an internal layout, the locking means thus have a holding (or held) portion located on a side of the implant while the stop portion is located on an opposite side of the implant. In some embodiments, the locking means are disposed within the horizontal plane (of the implant) and have a shape matching at least part of the periphery of the implant (for example matching a groove in the periphery). It may match the periphery of the plates (2) as for example shown in FIG. 27A or 28A, or the periphery of the shim (3) (not shown). The locking means (4) may then have a general U shape, with the two ends of the U being folded or curved toward the interior of the U, for example as shown in FIG. 27C. The locking means (4) may also have general L shape, with the one end of the L being folded or curved toward the other end, therefore forming a U-shape, for example as shown in FIG. 28C. This curvature or folding of the end(s) may preferably be at an angle of approximately 90° to provide a stop portion (for example oriented toward the interior of the implant), for cooperating with a stop (14, 42, 43) of a body (2, 3) or the anchor (1). The flexibility of the locking means then allows the stop portion to move transversally to open and close back for retaining the bodies (2, 3) or anchor (1). Such opening and closing of the locking means (4) disposed in the horizontal plane thus may induce a movement of the stop portion in the horizontal plane and perpendicularly to the insertion axis. However, in particular in the case of a L shape, as for example in FIG. 28C, it may be possible to provide various orientations of the locking means so that the opening and closing occurs in various directions, preferably not parallel to the insertion axis, as discussed in the present application. The folding or curvature of the stop portions may be angled at more than 90° so as to improve the ability of retaining the bodies (2, 3) or the anchor (1). The stop portions may comprise tapered ends (48) so as to facilitate the sliding of the bodies (2, 3) or anchor (1) before the locking, for example as visible in FIGS. 27C and 28C. The U shape may be provided with a fixation part (49), as a protrusion in FIG. 27C but possibly a recess, intended to cooperate with a complementary holding part (249) on the implant, as a recess receiving said protrusion in FIG. 27A, but possibly a stud entering said recess. Similarly, the L shape may comprise a branch (49) of the L intended to be held in a housing (249) of the implant, while the other branch of the L may comprise a curved and tapered stop portion (48) that is free to move within the implant (inside the recesses 42, 43). Other fixations are of course possible so as to retain the locking means, preferably at the level of its fixed part (held within the implant). It should be noted that in the examples of FIGS. 27E and 28E, the external/oppositely-held locking means (4) are used to lock the plates with respect to the shim, but that similar locking means may be used for locking the anchors, in various embodiments. These types of locking means may, as other locking means described herein, be in a radio-opaque material, so that they can be used for checking the position and orientation of the implant within the spine of the patient. For a better reliability, they may also be metallic, for example in titanium, as in other embodiments. In addition, it should be noted that the shapes of U or L described above are non-limiting because the shape of the external surrounding locking means may vary depending on shape of the implant and because they may be disposed in grooves of various shapes. Such shapes may be as a C or may be any convenient shape fitting the implant. Furthermore, internal locking means, for example, with a help portion opposite the locking portion with respect to the implant may also have different shapes, as for example a T shape in which the two uppers branches of the T may be used to each lock one side of the implant, while the lower branch is used as a flexible portion. However, any convenient shape of such internal locking means may be used, preferably for limiting the encumbrance within the implant.

In some embodiments, the locking means (4) of the implant are colored, for example anodized, so as to help their visualization before, during or after the surgery. The colored locking means will be preferably, but not exclusively, used in external layouts as detailed above. In some of these embodiments, a color code can be used so as to associate a color of the locking means with another feature of the implant, such as a size and/or a shape of the implant. For example, implants able to impose lordosis of different angles may comprise locking means of different colors to help their recognition.

Preferably, in the case of intersomatic or corpectomy cages, the implant is hollow, by means of at least one opening extending from said upper surface down to said lower surface, as particularly visible in most of the figures illustrating corpectomy cages in a non-limiting way. Such an opening of the implant between its surfaces in contact with the vertebral structures adjacent to the replaced vertebral segment allows insertion of cement and/or bone growth inside the implant and provides a wide continuous grafting space, giving the possibility of adding a bone graft or substitute for consolidating the operated vertebral segment. The insertion of cement or a graft may moreover allow the locking of the various bodies making up the implant. Thus, in certain embodiments, as illustrated in most of the figures, the peripheral wall includes at least one conduit (25, 35) for allowing insertion of cement and/or a graft and/or bone substitute into the implant, in order to facilitate bone growth through the opening of the implant. Further, it is generally provided that the various bodies of the implant provide such an opening ensuring continuity of the grafting space. Thus, the plates (2) preferably include a central opening (25) providing communication between the upper and lower surfaces and with a central opening (35) of the shim (3), for example as visible in most of the figures and notably in FIGS. 1A and 1B or 2A and 2B. On the other hand, in various embodiments, at least one portion of the bodies (2, 3) also includes at least one lateral opening (24) and/or an anterior opening and/or a posterior opening (29, 39) in order to provide communication of the grafting space with the periphery of the implant, such as for example visible in FIGS. 1A and 1B or FIGS. 9A, 9B, 9C, 9F, 11A, 11B, 11E, 26A, 26B and 26G. It will be noted that this type of peripheral opening (24, 29, 39) further allows insertion of cement, of a graft or bone substitute during the implantation, notably after having placed the implant in the vertebral segment to be treated. Further, it will be noted that the shape of the anterior and/or posterior opening (29, 39) may be laid out so as to mate the implantation instrumentation in order to allow guiding of the elements of the implant, notably the bodies (2, 3) relatively to the instruments used, as detailed hereafter with reference to FIG. 14B.

In some embodiments, the peripheral wall of the implant preferably includes hooking-up means (26, 36) for implantation instrumentation. Various layouts known to one skilled in the art are possible for these hooking-up means (26, 36) and it is not necessary to detail the characteristics thereof. These means (26, 36) are preferably provided both on the plates and on the shims, notably when the possibility of inserting the latter after each other is desired.

In various embodiments, the implant includes, or is associated with, one or more attachment means (1), the deployment of which allows anchoring of the implant to adjacent lower and/or upper vertebral structures. In order to overcome at least one of the drawbacks of the prior art, in some embodiments each of said attachment means (1) is deployed by sliding along at least one portion of the implant. In various embodiments, these attachment means (1) are deployed by sliding inside the implant through a passage (21) following an oblique path (generally through the plates (2) of the implant) between the periphery of one of the upper or lower vertebral contact surfaces. In various embodiments, these attachment means (1) preferably include at least one plate (10), at least one portion of which remains in contact with the implant at the end of the deployment in order to ensure good stability of the attachment. This plate (10) preferably is curved and crosses the implant via a curved or rectilinear passage or consisting of at least two rectilinear portions with different orientations. In various embodiments, the curved plate (10) is positioned in a vertical plane inside the passage (21) of the implant and the curvature of the plate (10) is oriented in this vertical plane, as illustrated on many of the figures of the present application. In certain embodiments, the portions of the fixing means which penetrate into the vertebral structures preferably include portions of plates, the width of which provides resistance to movements (from patient movements which are possibly passed onto the implant) allowing good stability in the rachis (better than portions of less significant extent, such as spikes or staples, might allow). In various embodiments, the front end of the anchor is refined and/or pointed, to better penetrate into the vertebrae, for example such as shown in FIG. 26G. Furthermore, in some embodiments, the anchor (1) has, at least at its portion intended to penetrate into the bone (near the front end portion and on a variable extent, preferably up to the front end itself), a H shaped cross section. For example, the plate (10) has a cutout (19) giving its cross section this shape of a H. Illustrative and nonlimiting examples of such embodiments are shown in FIGS. 26C, 26D and 26E. These embodiments of H shaped anchors offer a good resistance surface to oppose the movement in the bone, as can already offer a plate shape as such compared to thinner or fragile shapes such as nails or staples, but this form may have other benefits, such as to facilitate its insertion into the bone as it is cut (19) will result in a thinner cross section, which can also be sharpened on its edges (18), for example as shown in FIG. 26D. By combining such a cutout (19) in the plate (10) and a sharpening or thinning (18) of the front end, an anterior end thinner than the rest of the plate may be obtained, for example as visible in the FIG. 26G where it is understood that the front end may facilitate the penetration into the bone tissue. Furthermore, this H-shape may allow to preserve a good rigidity of the anchor (1) and therefore improves the reliability of the attachment (while limiting the size and invasiveness). Finally, such a shape may provide additional bone contact surfaces compared with a simple plate shape. Thus, the anchor in contact with the cortical and/or cancellous bone may be better retained, which may promote the resistance to movement of the cage.

Generally at least one attachment means (1) is provided for each of the upper and lower vertebral structures to the treated vertebral segment, as illustrated in most of the figures, but it is possible to only attach the implant on only one of these vertebral structures. On the other hand, it is understood that attachment means according to the embodiments of the present application may be provided, which will be different for both of these vertebral structures or even at least one attachment means different from those of the present application. It will be noted that the attachment means are generally rigid or stiff, for example in metal or in an alloy for providing good stability, even if a possibility of flexure of a portion of the anchor is provided in certain embodiments (in some cases, it is the particular layout which allows the restricted flexure and not the material). Thus, in various embodiments, each of said bone anchoring means (1) being deployed by sliding inside the implant, along a curvilinear path, through a passage (21) and between the outside of the peripheral wall and one of the upper or lower surfaces of the implant, and comprising at least one curved plate (10) on the one hand, for which at least one posterior portion remains inside the passage (21) at the end of the deployment and at least one anterior end juts out from one of the upper and lower surfaces of the implant on the other hand for penetrating into one of said vertebral structures at the end of the deployment. Preferably, the posterior end of the anchor (1) does not jut out from the periphery of the implant or only juts out by an insignificant proportion i.e. limiting the risks of damaging the surrounding tissues.

In certain of these embodiments, the bone anchoring means (1) are locked in the implant with at least one locking means (4) retained in at least one of the bodies (2, 3) and at least one abutment portion of which is laid out for passing from a so-called open position allowing sliding of the bone anchoring means (1) in their passage (21) to a so-called closed locking position, preventing sliding of the bone anchoring means (1) by the contact between at least said abutment portion and at least one abutment (14) of the bone anchoring means (1), said abutment (14) being oriented not parallel to the path covered by said passage (21) and said abutment portion passing from the open position to the closed position, for example with mechanisms of the type of those described in the present application. For example, the abutment portion passes from the open position to the closed position, elastically by flexure or torsion, by means of at least one flexible portion of the locking means (4) allowing withdrawal of said abutment portion from the locking means (4) in the open position during the sliding of the bone anchoring means (1) on the one hand and elastic return of said abutment portion into the closed position when it is found facing said abutment (14) of the bone anchoring means (1) on the other hand. In a similar way to the locking means (4) of the bodies, the locking means (4) of the anchor (1) preferably is retained in the implant, for example in a housing (41) that opens into a portion of the passage (21) of the anchor (1) for cooperating with an abutment of the latter in order to lock it in the implant. The various figures of the present application show illustrative and non-limiting examples of the orientation and configuration of this lock (4) of the anchors in the implant. In certain of these embodiments, a same locking means (4) locks at least two bodies (2, 3) and at least one bone anchoring means (1) at the same time. In other embodiments from among these embodiments, the bodies (2, 3) and the bone anchoring means (1) are locked by different locking means (4).

In certain embodiments, the anterior end of an anchor (1) includes at least one spike and/or at least one sharpened portion (18) facilitating penetration into the vertebral structures. FIG. 1C, 2C, 3C 4C, 5C, 6C, 26C or 26D show examples of such sharpened portions and one skilled in the art understands from the disclosures of the present application that this sharpening may be provided on one or more of the faces and/or on one or more of the edges of the plate (10), at least at the anterior end, but preferably not on the portions of the anchor which remain in the implant (in order to avoid cutting the latter). Also, it is generally preferred that the anterior end should be sharp in order to better penetrate the bone tissues, but various embodiments are possible, notably with or without this type of sharpening. These attachment means (1) therefore generally include at least one sharp end jutting out from one of the upper and lower surfaces of the implant in order to penetrate into one of said vertebral structures at the end of the deployment of the anchors in the vertebral structures.

Figure 1A:
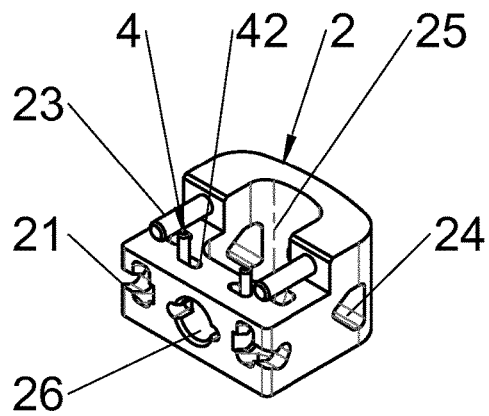
Figure 1B:
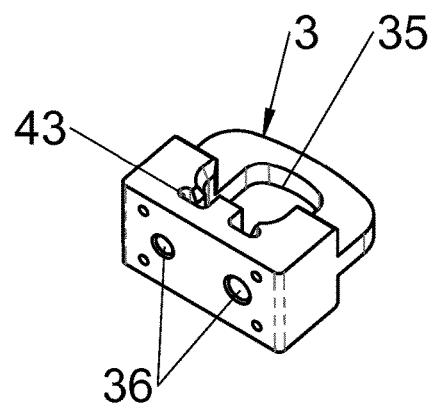
Figure 1C:
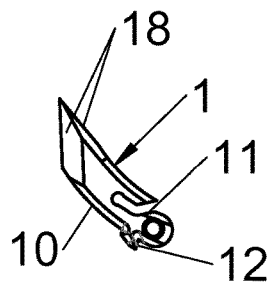
Figure 1D:
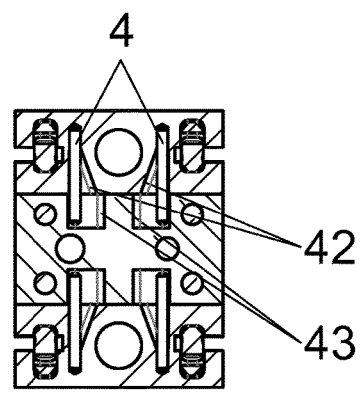
Figure 1E:
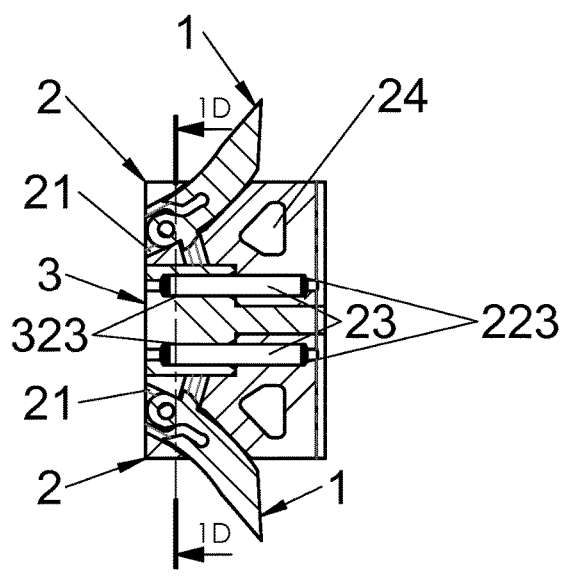
Figure 1F:
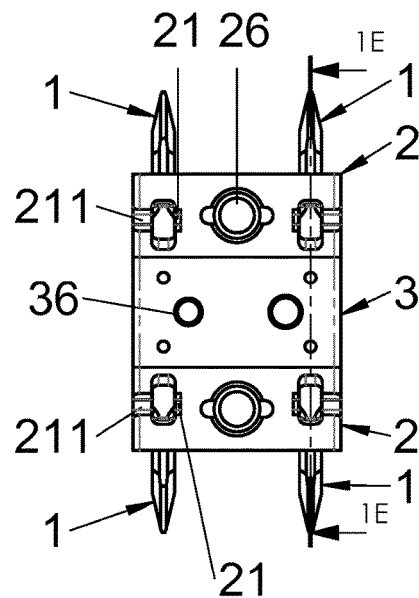
Figure 2G:
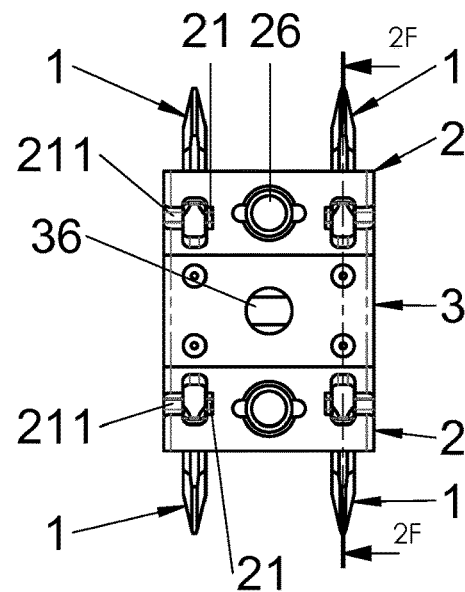
Figure 3E:
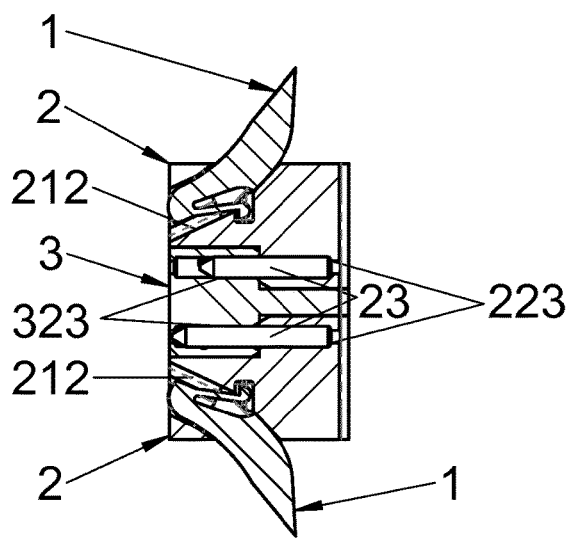
Figure 3F:
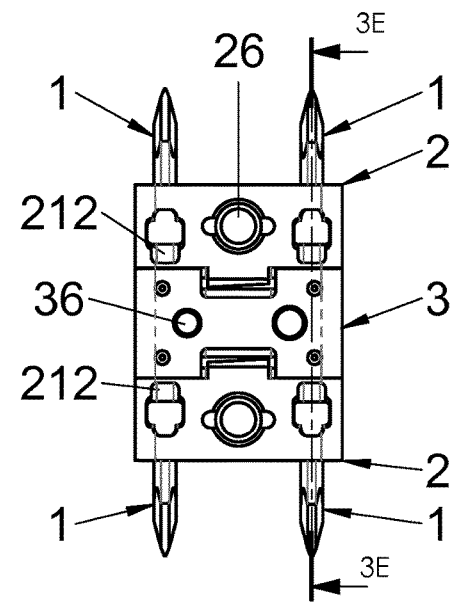

In certain embodiments, said curved plate (10) includes, in proximity to its posterior end, at least one abutment surface (211) preferably not parallel to the surface of the plate for limiting the penetration of the bone anchoring means (1) in the implant. An example of such an abutment is illustrated in FIGS. 1F and 2G showing a lateral tab at the posterior end of the anchor, capable of abutting against the lateral edge of the passage (21) and of limiting penetration of the anchor (1) into the implant. More generally, in certain embodiments, at least one posterior portion of the curved plate (10) of at least one of the bone anchoring means (1) is laid out in order to be retained inside the passage. This retention may be obtained by the fact that the dimensions of the anchor (1) are equal to or slightly greater than that of the passage at this posterior end, without requiring any other structure. FIG. 7E represents an illustrative and non-limiting example of such an anchor not including any additional abutment structure. On the other hand, in various embodiments, the anchor (1) includes at least one notch engaging into the wall of the passage (21) of the implant for immobilizing the bone anchoring means (1) at the end of the deployment. Such a notch may be positioned on any face of the plate (10) and be provided for sinking into the wall of the passage (21) or for cooperating with a housing provided in a wall of this passage (21). For example, the plate (10) may include a flexible tab provided with a notch (12) at its end, like for example in FIG. 3C, for immobilizing the anchor relatively to the implant. This notch may include an abutment surface opposing the withdrawal of the anchor like in FIG. 3C or limiting the advance of the anchor in the passage, or filling both of these roles at the same time. In certain embodiments, at least one exterior portion of the curve plate (10) includes at least one abutment (12) mating an abutment in the passage (21) of the implant for immobilizing the bone anchoring means (1) at the end of the deployment, said curved plate (10) including, on at least one posterior portion, a slot (11) crossing the whole of its thickness giving the possibility of providing elasticity to this posterior portion and allowing mutual engagement of these abutments, like this is for example visible in FIGS. 1C and 2C. It will be noted that this type of notch (12) of FIGS. 1C, 2C and 3C may allow, in certain embodiments, the clearing of the notch out of the implant during withdrawal of the bone anchoring means (1). Such a withdrawal may be obtained by pushing the flexible tab or by compressing the slot (11) for example by actuating an irregularity (for example a housing) on the posterior end of the anchor. For this, the implants may include, for example, access (212) to the posterior end of the anchor (1), such as for example a housing located in proximity to the entry of the passage (21) and capable of receiving the end of a tool for actuating the irregularity at the posterior end of the anchor (1). Illustrative examples of such accesses are illustrated in a non-limiting way in FIGS. 1F and 2G, with the housing on the side of the entry of the passage (21) for allowing compression of the slot and withdrawal of the anchor (1), or in FIGS. 3E and 3F with the housing (212) above or below the passage (21) for accessing the flexible tab provided with the notch (12). Also, the locking means (4) of the bodies (2, 3) and/or of the anchors (1) of the implant may be made accessible in a similar way in order to facilitate ablation of the implant if required. Thus, in some embodiments, the implant and/or the anchor may comprise at least one access (112, 212) to at least one locking means (4) for placing the latter in the open position so as to obtain a release. Note that in the case of a locking means (4) of the anchor (1), such an access may be provided on the implant and/or on the anchor (1) itself. Indeed, the anchor may include a groove, a cutout or have a shape for introducing a tool to the level of the abutment portion of the locking means (4), where it has a clearance in the implant near where it locks the anchor (1), for actuating the lock (4) to release the anchor (1). For example, in FIGS. 26C and 26D, the anchor (1) has a groove (112) on the side comprising the abutment (14) which cooperates with the latch (4). This groove (112) forms an access for pushing on the latch to release the anchor, as seen for example in FIG. 26F. These examples of access (112, 212) are of course illustrative and not limiting as they may have different forms and various locations on the anchor and/or any body of the implant. Similarly, in the examples of FIGS. 3E and 3F, the anchor and implant comprise complementary shapes and this arrangement allows the insertion of a tool to the level of the locking catch. On the other hand, the abutment surfaces of the lock (4) and of the implants may be provided for allowing withdrawal of a body (for example the shim) by pushing back the lock (4) in the same way as upon inserting this body. Similarly, the shapes of the stop (14) of the anchor (1) and the abutment portion of the latch (4) may be provided to facilitate removal of the anchor, such as a latch of cylindrical shape cooperating with a complementary recess on one side, an edge or a portion of the anchor (1). Thus, by pulling on the anchor, it may be possible to unlock and withdraw it, while it may be avoided that it is removed too easily under the effect of forces exerted on it when the patient moves. Finally, various embodiments of the anchor (1) comprises traction means (121) for pulling on the anchor to withdraw it. Such means may be a notch, a slit or a hole, preferably at the rear end of the anchor, for example as seen in many of the figures including FIG. 2C, 4C, 5C, 8C, 26C, 26D or 26F. It will be noted that the various embodiments for locking the anchors in the implant generally relate to a given anchor while the implant may be attached with several anchors at the same time. These various embodiments are therefore not exclusive of one another.

It will also be noted that various embodiments give the possibility of having the attachment means pre-mounted on the implants in order to facilitate the preparation of the implantation during the surgical operation. On the other hand, in certain embodiments, said curved plate (10) includes, on an anterior portion intended to penetrate the vertebral structures, at least one tooth, one notch or indentation for improving the retention of the anchor in the penetrated tissues, such as for example an indentation (16) in proximity to the sharpened anterior end (18) of the anchor in FIG. 11C. As detailed above in the present application, certain embodiments of the present disclosure relate to attachment means inserted along a curvilinear path and/or an implant including such attachment means. Such a path is advantageous since it allows anchoring of the implant by using the same approach route as the one used for inserting the implant into the treated vertebral segment and therefore allows easier access facilitating the impaction of the attachment means in the vertebrae, notably along an approach axis (at least approximately) perpendicular to the axis of the rachis.

Figure 4A:
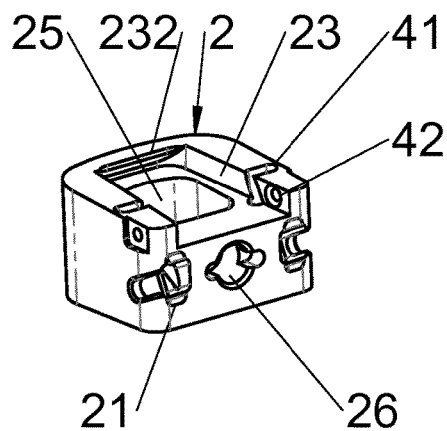
Figure 4B:
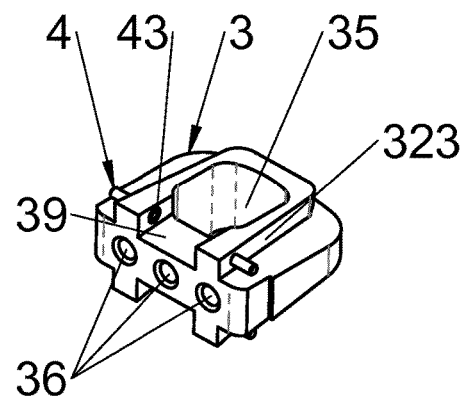
Figure 4C:
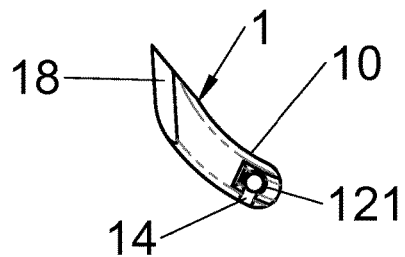
Figure 4D:
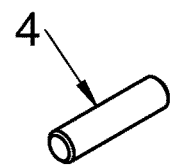
Figure 4E:
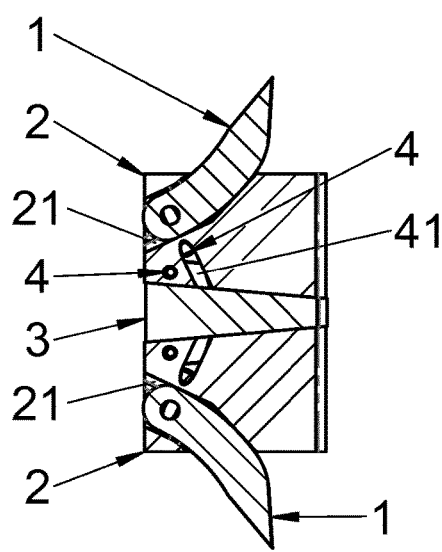
Figure 4F:
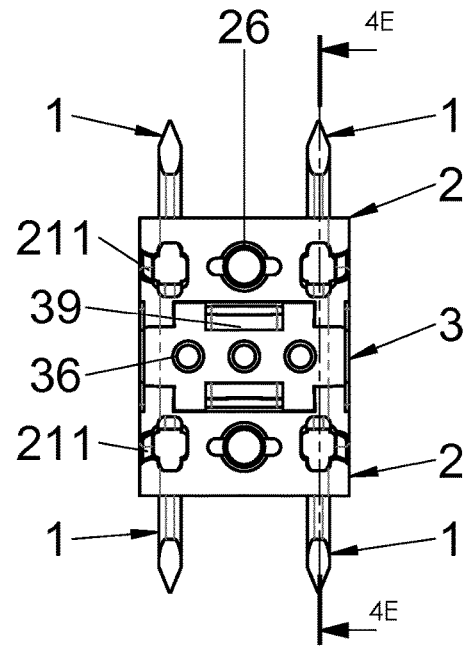
Figure 10A:
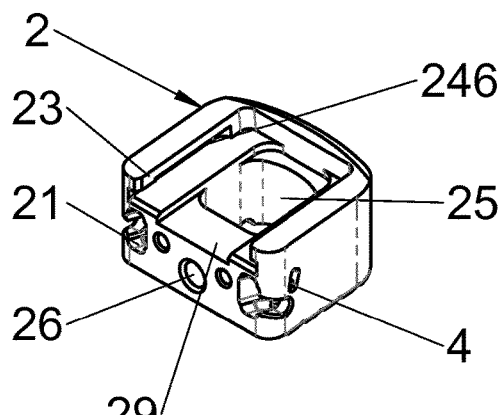
Figure 10B:
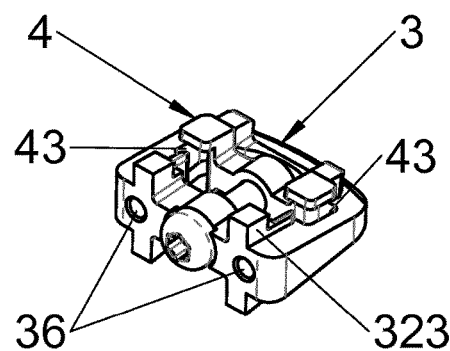
Figure 10C:
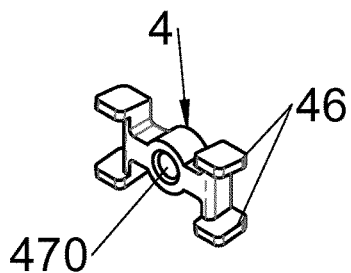
Figure 10D:
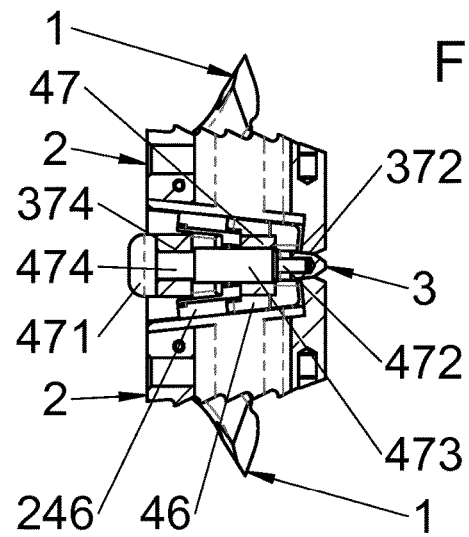
Figure 10E:
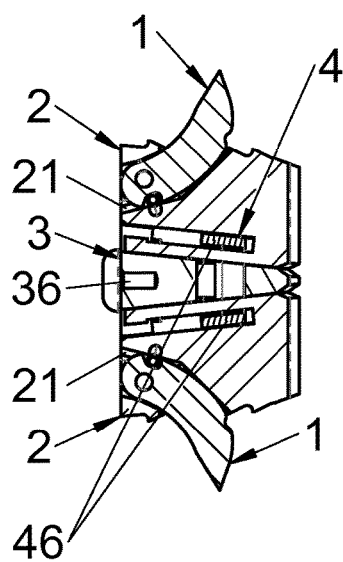
Figure 10F:
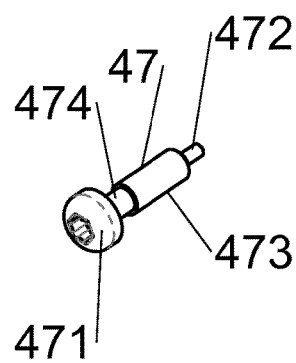
Figure 10G:
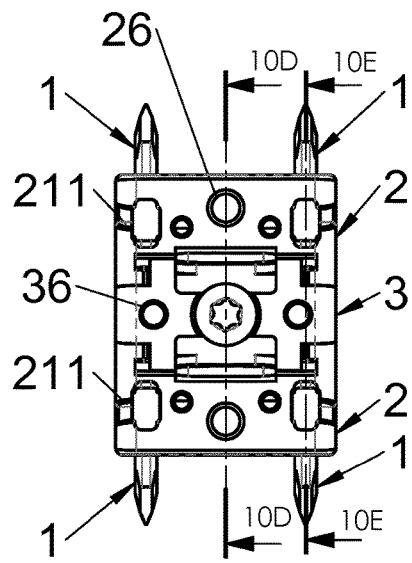
Figure 12A:
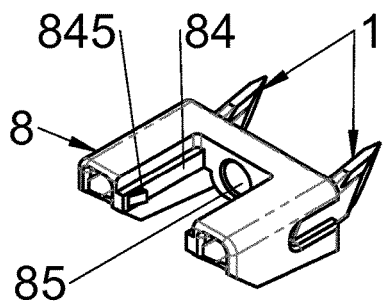
FIG. 12A illustrates a perspective view of a loader of bone anchoring devices according to various embodiments.
Figure 12B:
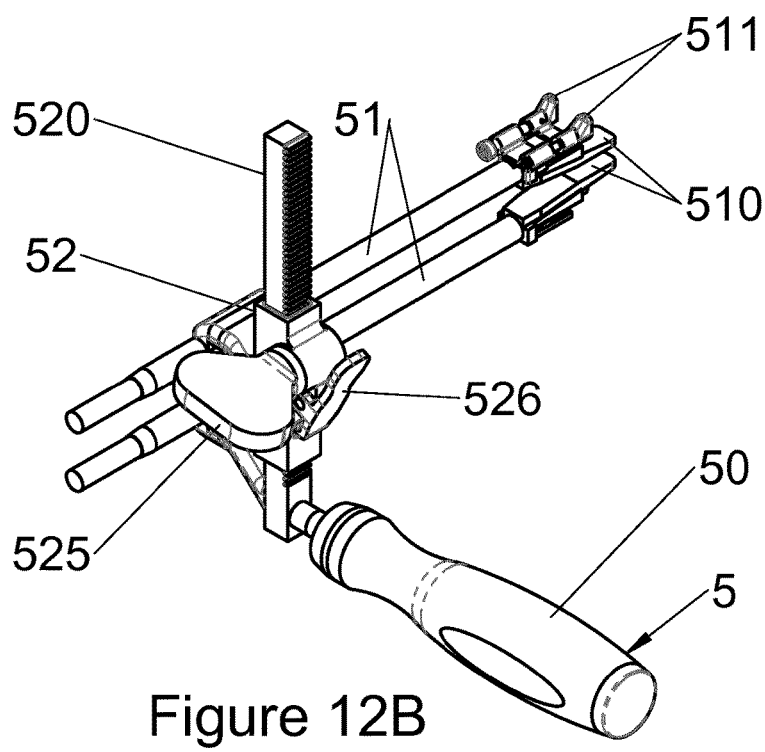
FIGS. 12B and 12C illustrate perspective views of an implant holder, before and after mounting loaders on the implant holder, respectively, according to various embodiments.
Figure 12C:
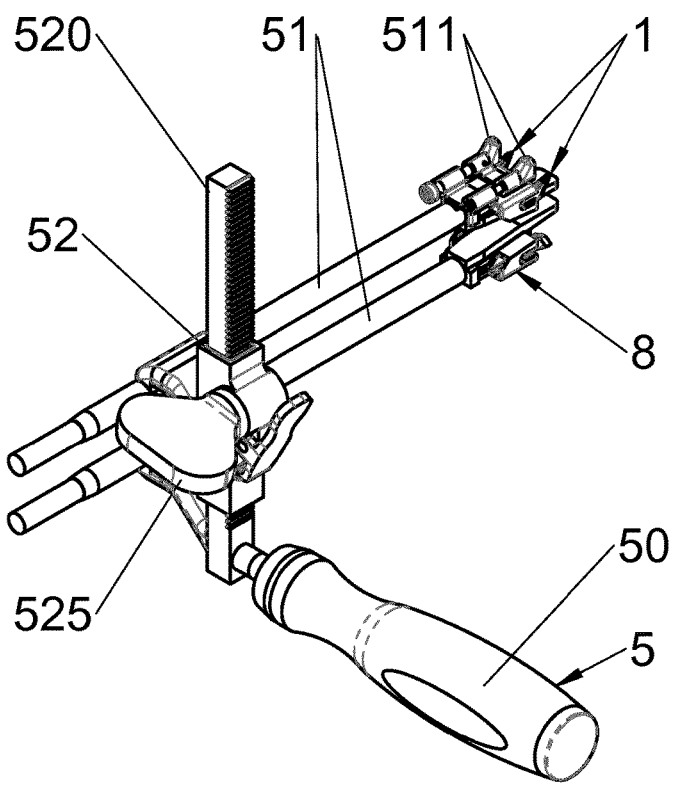

Various embodiments of the present application relate to other types of vertebral implants, other than those discussed above and comprising a locking means (4) locking the bodies by elastic return after flexure or torsion. These other types of vertebral implants, for example corpectomy or fusion, are also intended to be inserted into the rachis along at least one approach route, for replacing a vertebral segment. These implants extend, along a vertical axis, between upper and lower surfaces of the implant each intended to be placed in contact with respectively a vertebral upper and lower structure, of said vertebral segment. These implants also include at least one first body (2) and at least one second body (3) each having, at least one face having shapes and dimensions mating those of at least one face of the other body (3, 2). These mating faces form fitting means for allowing mutual engagement of said bodies (2, 3) along a sliding axis not parallel to the vertical axis. On the other hand, these implants include at least one locking means (4) retained in at least one of the bodies (2, 3) and at least one abutment portion of which is capable of passing from a so-called open position allowing sliding for mutual engagement of said bodies (2, 3) to a so-called closed position, locking said bodies (2, 3) engaged together through the contact between at least said abutment portion and at least one abutment (42, 43) of at least one of said bodies (2, 3). Generally, this abutment (42, 43) is also oriented not parallel to the sliding axis. In certain of these embodiments, said abutment portion passes from the open position to the closed position, by translationally actuating the locking means (4) along a direction not parallel to the sliding axis. Locking is therefore obtained by translation of the locking means (4), generally by means of actuation of the locking means (4) itself, for example with the end of a tool. FIGS. 4A, 4B and 4E represent illustrative and non-limiting examples of such implants. In these examples, the locking means is oriented along an axis perpendicular to the vertical axis and not parallel to the sliding axis (for example perpendicular to the sliding axis for better locking). The lock (4) is for example slideably mounted in a housing (43) of the shim (3) and capable of being pushed into an abutment housing (42) of a plate (2). In order to slide such a block (4), an access (39) is provided from one face (preferably a posterior face) of the implant. FIG. 4B illustrates the shim (3) with its lock (4) in the closed position while the latter will of course be in the open position before assembling this shim (3) with the plate (2) of FIG. 4A. It will be noted that in these examples, the locking means (4) of the anchor (1) is a lock (4) distinct from that of the bodies, which is provided with a flexible portion and mounted in a housing (41) of the implant and that it is laid out for engaging with an abutment (14) of the anchor (1). The same applies in the illustrative and non-limiting examples of FIGS. 6A, 6B, 6D, 6E, 6F and 6G. It will be noted that FIGS. 6G and 6D show that the anchor (1) is locked with a lock (4) housed in a conduit (41) with an oblique orientation inside the implant (in the plates (2) in this example). On the other hand, it will be noted that in FIGS. 6A, 6B and 6F, the illustrated lock example (4) of the bodies (2, 3) may be translationally actuated parallel to the vertical axis. FIG. 6B shows a means (38) for accessing the locking means, for example with a tool for sliding the locking means and putting it in the closed position as illustrated in FIG. 6B. From FIGS. 4B and 6B it is for example understood that various orientations of a lock (4) which may be actuated translationally, are possible and that the illustrated examples are non-limiting since various orientations or configurations are possible, from the moment that an access (38, 39) is provided for actuating the lock (4) not parallel to the sliding axis. On the other hand, in certain embodiments, an actuating means (47) is directly provided on the lock (4) in order to be able to have it pass from the open position to the closed position (and possibly from the closed position to the open position if the possibility of unlocking is desired). In certain of these embodiments, said abutment portion passing from the open position to the closed position, with an actuating means (47) actuated in rotation around an axis parallel to the sliding axis and causing translation of the locking means (4) along a direction parallel to the sliding axis. FIGS. 10C and 10F show an example of such a lock (4) and of such an actuating means (47), respectively. A channel (470) is laid out in the lock (4) for receiving the actuating means (47). FIG. 10B shows an example wherein such a lock (4) is mounted in the shim (3) and allows locking of two plates (2) as illustrated in FIGS. 10D and 10E for example. It is understood that the lock (4) may be mounted in a plate (2) also according to the configuration of the implant. In some embodiments, the actuating means (47) causes translation of the lock (4) parallel to the sliding axis. Actuation means (47) may comprise locking means for locking the actuation and therefore locking the locking means. Such lockable actuation means (47) may be as a screw mechanism as illustrated herein, but may have various structural arrangements. In the example showed, tapping of the channel (470) is achieved for cooperating with threading (473) of the actuating means, so that actuation of rotation about the axis of the actuating means (47) for example on a screw head (471) capable of receiving the end of a tool (a flat, cruciform Allen or torx tool for example), parallel to the sliding axis, causes translation of the lock (4) parallel to the sliding axis. Such a lock (4) retained in a body (2, 3) then includes at least one abutment (46) coming into contact with at least one portion of another body (3, 2). For example, fins (46) of the lock mounted on the shim (3) slide in order to be blocked on the plate (2), for example by cooperating with grooves of the plates with dimensions substantially identical with or slightly greater than those of the fins, but preferably with slightly tilted orientations relatively to the sliding axis. Thus, locking is obtained not only parallel to the sliding axis, but also parallel to the vertical axis since the fins (46) retain the plates (2) by means of the grooves of the latter. It will be noted that in the example of FIGS. 10F and 10D, the actuating means (47) includes a thinned anterior end (472) and not threaded, laid out for cooperating with a mating housing (372) in the peripheral wall of the shim (3) at its anterior edge, in order to maintain the actuating means in the sliding axis. Further, the actuating means includes in the example of FIG. 10F, the screw head (471) and the threaded portion (473) and they are separated by a non-threaded portion (474) with an outer diameter at most equal to the diameter of the interior thread of the threaded portion (473), so that for inserting the actuating means (47) into the shim (3) like in FIG. 10D, for example, the threaded portion (473) is screwed into a mating tapped hole (374) in the posterior wall of the shim (3) and, at the end of the screwing, the non-threaded portion (474) is the one which is found at this tapped hole (374) and the shim (3) then allows the actuating means (47) to freely rotate, the threaded portion of which drives the lock (4). Various other configurations and embodiments are possible from the mechanisms described above. For example, an actuating means (47) mounted on a body (2, 3) and driven into rotation in a similar way to that of the examples of FIGS. 10B, 10C, 10D and 10F may include at least one radial fin (for example two diametrically opposite fins) forming the locking means and the actuation into rotation then allows this fin to pass from a horizontal orientation corresponding to an open position to a non-horizontal position, for example a vertical position, in which it juts out from at least one of the upper and lower surfaces of the body in which the actuation means is mounted, in order to come into contact with a wall (for example the inside of the posterior peripheral wall) of the other body and thus lock both bodies like a pivoting latch. It will be noted that such a locking means is reversible and that a notch may be provided on the wall against which the fin will come into contact, so that the switching into an open position is more difficult than switching into a closed position. Further, provision may be made for the fin to also include a notch cooperating with a mating circular groove of the path of this notch so that such a lock limits the risks of lifting the bodies (2, 3). In certain alternatives of such embodiments, such a radial fin may also be laid out for pushing upon a slideably mounted lock (4) in a housing, like in various embodiments such as those of the examples of FIGS. 4B and 6B. Locking similar to that of a latch on a locking switch is then obtained driven by a key and it is possible to provide it reversible also according to the configurations (for example, the available size) in the implant. It will also be noted that such radial fins may include flexible tabs not parallel to the fins and laid out in order to be compressed when the fins are in the closed position on the one hand, for example when the body (2, 3) is held by an instrument at the actuating means (47) which coincides with or forms a means for hooking up (26, 36) the implant and, to be released elastically on the other hand when the instrument releases the actuating means (47), so that the fins are pushed back into the non-horizontal position corresponding to the closed position of the lock. An automatic mechanism for actuating the locking is then obtained. In other alternative embodiments, the actuating means may be translationally actuated along a direction substantially parallel to the sliding axis. With such a sliding actuating means, an anterior end surface of this actuating means may be provided not perpendicular to the sliding axis so that this tilted surface cooperates with a mating surface of the locking means (4). Such locking means (4) may then be slideably mounted along a direction not parallel to the sliding axis and be driven in translation not parallel to the sliding axis by the thrust exerted on the actuation means and the contact of the tilted surfaces. In other alternatives, such a locking means (4) with a tilted surface may then be freely mounted rotatably about an axis parallel to the sliding axis and be driven into rotation about this axis parallel to the sliding axis by the thrust exerted on the actuating means and the contact of the tilted surfaces.

Figure 9A:
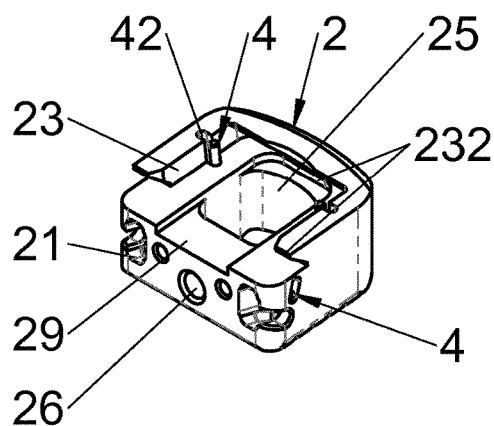
Figure 9B:
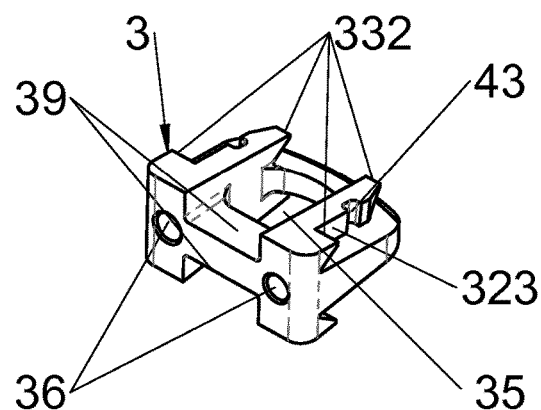
Figure 9C:
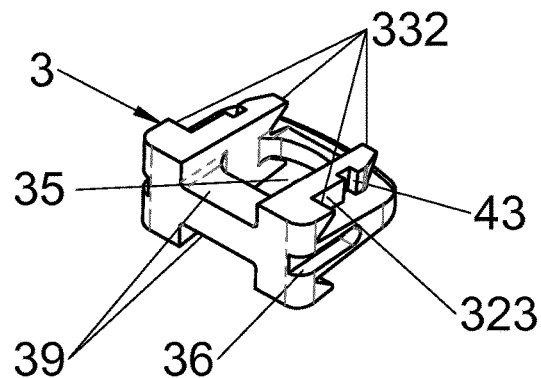
Figure 9D:
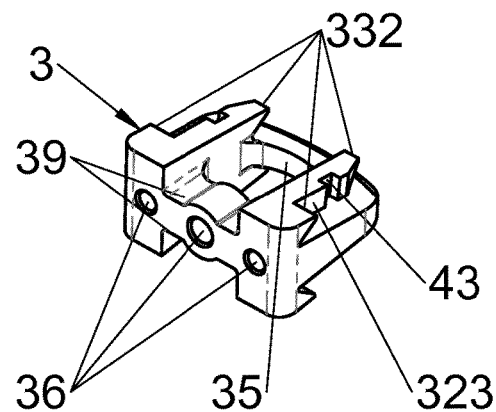
Figure 9E:
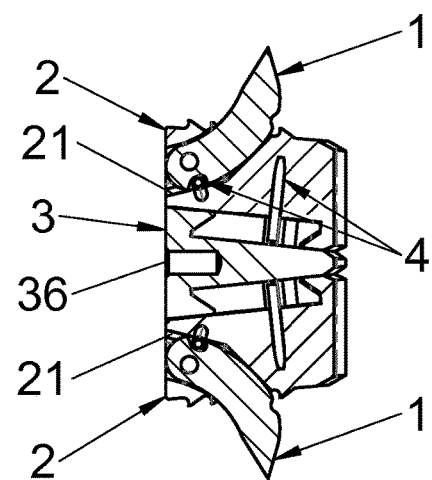
Figure 9F:
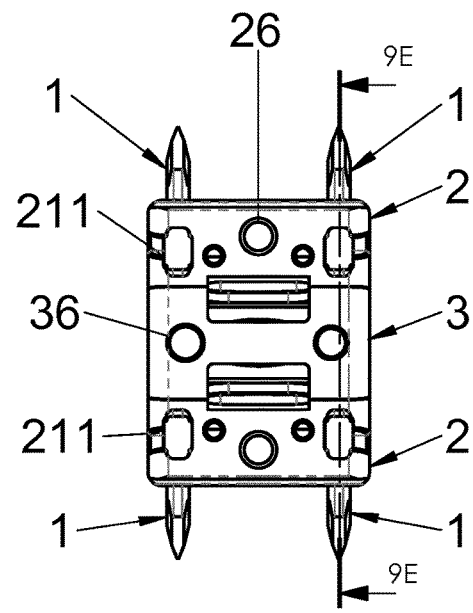

Various embodiments of the present application relate to instrumentation for inserting an implant into a rachis and preferably for attaching the implant in the adjacent vertebral structures. Such instrumentation in some embodiments may include an implant holder (5) comprising means for its grasping by hand, such as a handle (50) for example, and retaining means which mate hooking-up means (26, 36) present on the implant. Various types of retaining means and of hooking-up means are known from the prior art, such as for example rods of the implant holder, either threaded or not, penetrating into the housings, either tapped or not, of the implant, or arms of the implant holder cooperating with lateral edges and/or upper and/or lower faces of the implant, for example by inserting said arms into grooves of the implant. The present application does not describe these known means and the examples of housings (26, 36) illustrated in the figures are not limiting, since various configurations are possible. Moreover it will be noted that FIGS. 9C and 11B show examples of a groove (36) capable of cooperating with an arm of an implant holder. Further, it will be noted that the number, the shape and the position of the hooking-up means (26, 36) may vary, as visible in the figures of the present application and notably in FIG. 9D illustrating an exemplary alternative embodiment with three hooking-up means instead of two like in FIG. 9B or for example FIGS. 26A and 26B showing holes (26, 36) of variable and non-aligned positions on the plates (2) and the shim (3). In various embodiments, the implant holder (5) is intended to be used with implants of the type of those described in the present application, and preferably has means (52, 520, 525) for distraction of these vertebrae. The term of "distraction" is used in its definition known in the field of vertebral implants which designates the fact that two vertebral structures are moved away from each other. Indeed, for corpectomy implants but also of many other types of implants, it is often useful to have a tool capable of imposing a determined height in the space into which the implant has to be inserted. In various embodiments of the present application, the assembly of the bodies (2, 3) allows this determined height of the space to be smaller than the final height of the implant, but it remains often useful to impose this height which is generally greater than that observed in the absence of distraction, since the adjacent tissues tend to collapse or settle down when a vertebral structure is withdrawn. The distraction means (510, 52, 520, 525, 526) may include, in certain embodiments, means (525, 526) for locking the distraction, giving the possibility that the height obtained with the distraction means (510, 52, 520, 525, 526) moving apart the vertebral structures is maintained fixed by the locking means (525, 526) without having to act on the actual distraction means (510, 52, 520, 525, 526), further, as the implant holder (5) is preferably intended to be used with an implant comprising at least two mating bodies (2, 3) and which may be assembled consecutively rather than simultaneously, the implant holder includes at least two arms (51, 61), each of which is capable of retaining one of said bodies (2, 3) by means of retaining means which mate hooking-up means (26, 36). Preferably, in various embodiments the implant holder (5) includes two first arms (51) for holding two first bodies or plates (2) and at least one other arm (61) for holding at least one other intermediate body (3). The distraction means (510, 52, 520, 525, 526), for example, may then preferably laid out for moving the two first arms away from each other. In the illustrative and non-limiting examples of FIGS. 12B, 12C, 13A, 13B, 13C, 15A, 15B, 15C, 16A and 16B, the distraction means (510, 52, 520, 525, 526) are formed with a sort of rack mechanism and include a body (52) in which a bar (520) is slideably mounted, provided with notches cooperating with a notched knurl (525), the rotation of which in the body causes translation of the bar (520) in the body (52). The body is secured to one of the arms (51) of the implant holder, while the notched bar (520) is secured to the other arm (51) so that actuation of the knurl causes the arms (51) to move away or closer to each other. In these examples, the notched knurl (525) forms an actuator as well as a lock, but it is generally preferred to add an additional locking means, for example such as pivoting latch (56) and provided with a notch engaging with those of the bar (520), for example when it is actuated or by the elastic return of a means (such as a spring for example) when its actuation is interrupted. Further, it will be noted that in the illustrated examples for these embodiments, the distraction means include spatulas or plates (510) capable of penetrating into the implantation space and of supporting at least one portion of the bodies (2, 3) of the implant. In certain embodiments, these distraction means of the first bodies (2) such as the spatulas (510) for example also form guiding means for the second body which will be inserted subsequently. Indeed, in some embodiments these distraction means may include surfaces for guiding the bodies in order to facilitate their approach to each other and their sliding.

Figure 13A:
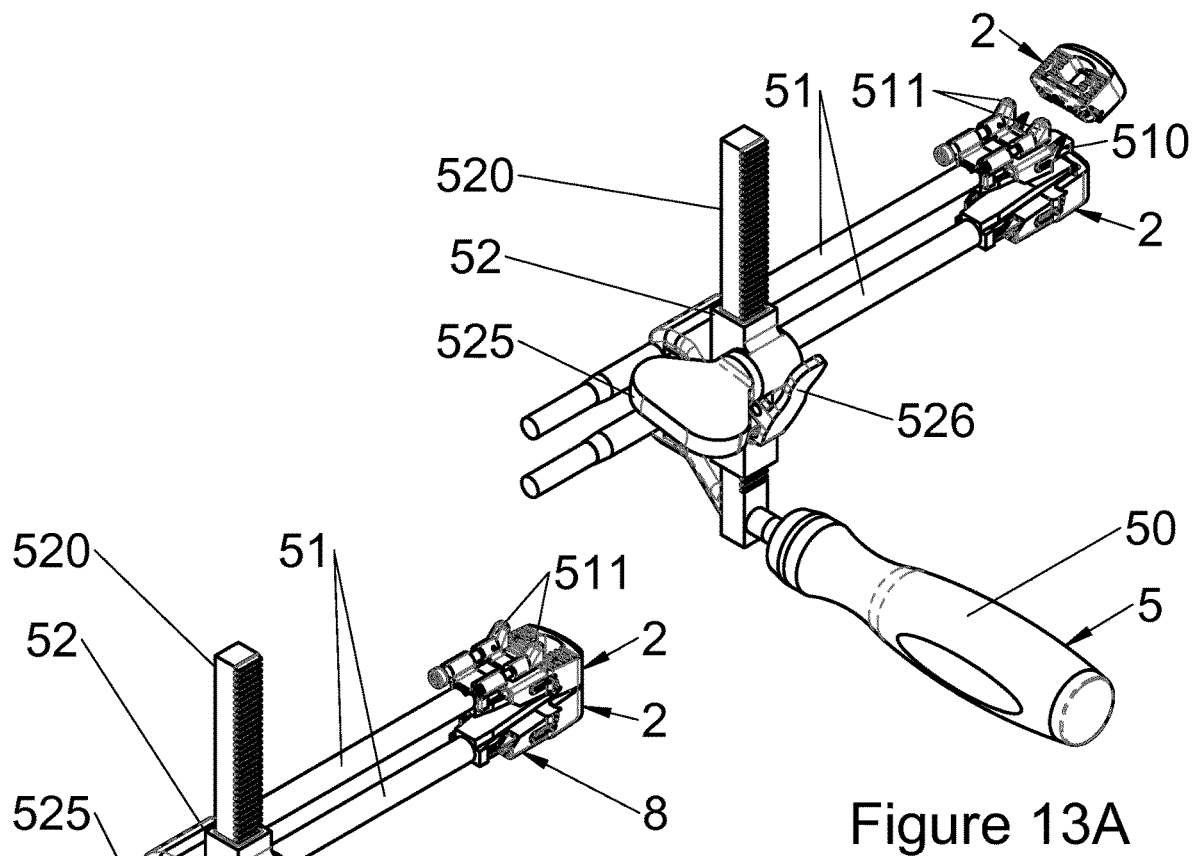
FIGS. 13A, 13B and 13C illustrate perspective views of an implant holder, respectively, during the mounting of the first bodies on the implant holder, and then before and during the adjustment of the abutments of the implant holder, according to various embodiments.
Figure 13B:
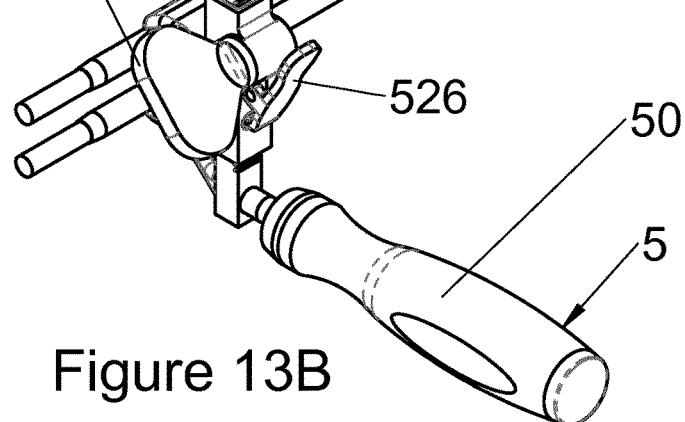
Figure 13C:
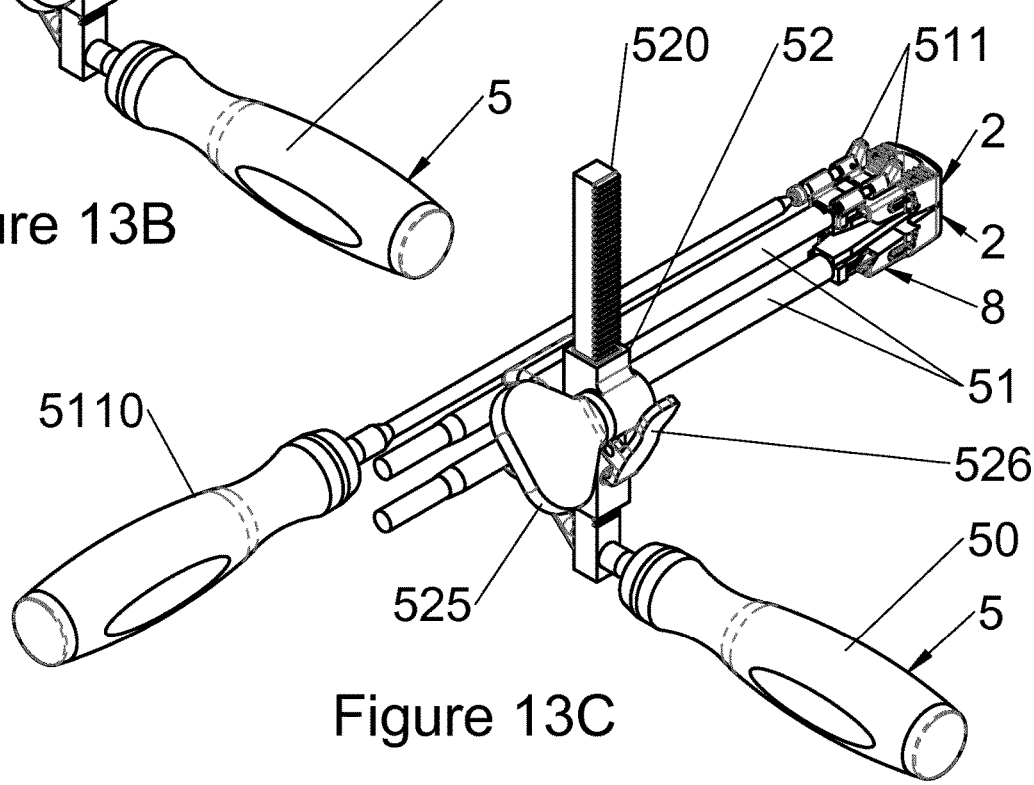

In certain embodiments, the implant holder (5) includes means (511) for adjusting the insertion depth of the implant. These adjustment means (511) may for example include position pads adjustable along the axis of the arms (51) of the implant holder limiting the distance with which the implant holder may penetrate into the vertebral implantation space. The instrumentation moreover may in some embodiments provide an adjustment instrument (5110) of these means (511) for adjusting travel, as for example illustrated in FIG. 13C. In this example, the adjustment is carried out as shown in FIG. 13C after having mounted the first body (2) on the implant holder (5), as illustrated for example in FIG. 13A.

In various embodiments, the instrumentation includes a loader (8) comprising a body provided with at least one housing for receiving a bone anchoring device (1), for example of the type of the various embodiments described in the present application. Such a loader (8) may in some embodiments include a means (84, 845, 85) for retention by the implant holder so that it is mounted on the implant holder and exhibits the bone anchoring device (1) in an adequate position for attaching the implant. For example, the implant holder may cooperate with a hole (85) of the loader and/or with guiding faces (84) of the loader, for example comprising grooves and/or ribs. A notch (845) may be provided on these guiding faces (84) in order to immobilize the loader on the implant holder (5). It will be noted that in the example of FIG. 13A, the anchors (1) are loaded into the loader (8) which is mounted on the implant holder (5) before the bodies (2) are mounted on the implant holder (5).

In various embodiments, the instrumentation is intended for use with implants having at least three bodies (2, 3) and includes an arm (61) for bearing the intermediate body (shim), for example by means of retaining means which mate hooking-up means (36) of the shim (3). In some of these embodiments, this arm (61) is preferably on a shim holder (6) distinct from the implant holder (5), so as to be able to be used once sufficient distraction has been achieved, for example as illustrated in FIGS. 14A, 14B, 14C, 15A, 15B, and 15C. The shim holder (6) in some embodiments preferably includes means for grasping it by hand, such as a handle (60) for example. Further, in these examples, the shim holder includes guiding means (62, 64). In certain embodiments, these guiding means include guiding means (62) relatively to the arm(s) (51) of the implant holder (5). It will be noted that the borne shim (3) also typically has a shape which follows the same profile as these guiding means (62) of the implant holder. This shape may be obtained by cutouts or anterior and/or posterior openings (29, 39) as discussed above with reference to the insertion of cement, of a graft or a substitute, for example as visible on FIG. 26A, 26B or 26G. Thus, in some of these embodiments the shim (3) and the shim holder (6) are guided so as to remain properly aligned along the arms (51) of the implant holder. In certain of these embodiments, the arm (61) includes at its end bearing the shim (3) other guiding means (64), for example for cooperating with guiding means (510) of the implant holder, such as the spatulas described above for example. In the illustrated examples, notably in FIG. 14B, it is actually understood that the end of the shim holder (6), by the presence of its guiding means (64) will easily slide on the spatulas (510). Further, in some embodiments this improved sliding may facilitate distraction when the guiding means (64) with a planar shape slides over the planar and sloped surface of the spatulas (510). In certain of these embodiments, the shim (3) is retained on the shim holder (6) by retaining means (63) giving the possibility of attachment, such as for example a screw (630) or a pin introduced into the shim, for example by means of an instrument (630), as for example illustrated in FIG. 14C. The illustrative and non-limiting examples of FIGS. 15A and 15B show the sliding of the shim holder (6) between the arms (51) of the implant holder allowing insertion of the shim (3) between the plates (2) of the implant.

In certain embodiments, the instrumentation includes at least one impacting device giving the possibility of planting the bone anchoring means into the vertebral structures through the implant. Such a device is designated under the term of impactor (7), illustrative and non-limiting examples of which are illustrated in FIGS. 15C, 16A, 16B and 16C. The impactor (7) in some embodiments includes a body (70) which may generally grasped by hand and a posterior impacting end (73) on which it is possible to strike, so that the body (70) transmits the shock to at least one thrust end (72), opposite to the impacting end, and thus allows the anchors (1) to be planted into the vertebrae (for example by means of a tool such as a hammer for example). Preferably, means (71) for guiding the impactor relatively to the implant holder (and/or to the shim holder) are provided, as for example visible in the example of FIG. 15C. In these illustrated examples, the impactor (7) includes two fingers (72) at its thrust end for pushing both anchors (1) at the same time. These fingers are preferably laid out so as to penetrate into the body of the loader (8) retaining the anchors (1) on the implant holder (5) and to thus pass through the loader for pushing the anchors (1) as far as the peripheral wall of the implant. FIGS. 16A and 16B show illustrative and non-limiting examples of such a mechanism for impaction of the anchors (1) in the vertebrae.

It will be noted that the force exerted on the vertebral structures generally will be as significant the force which therefore has to be exerted on the arms (51) of the implant holder, which usually is significant. It is therefore preferable that the arms be of a sufficiently reduced length and/or with a sufficiently large stiffness so that the moving apart achieved at the distraction means is actually passed on to the implant itself. In various embodiments, the bodies of the implant include mating tilted faces relatively to the plane transverse to the vertical axis and even if the moving apart is not perfectly imposed by the instrumentation, the insertion of the shim gives the possibility of making up for it. Nevertheless, various embodiments of the instrumentation aim at limiting this separation gap problem (for example in order to avoid embrittlement or damaging of the bodies of the implant during the implantation). For example, in certain embodiments such as in the cases of an implant holder of the type of those described above or of those described below and notably those illustrated in the illustrative and non-limiting examples of FIGS. 17 to 20, the instrumentation includes a distractor (9) (or retractor) inserted between the arms of the implant holder (5). With such a distractor it is possible to move the arms (51) apart by exerting thrust on the latter as far as close to their end holding the implant. In the illustrated examples, such a distractor (9) comprises two arms (90) fitting the arms (51) of the implant holder (5) and between which at least two crossbars (91) are connected together through a central hinge (92) at the location where they cross each other. In these examples, these two crossbars (91) are also each connected at one of their ends to one of the arms (90) of the distractor (9) through a fixed hinge (93) and each include at their other end, a free hinge or a guide for sliding along the other arm. In the illustrated examples, this other end of each crossbar (91) is provided with a free hinge connecting it to a rod connected to a second central hinge. In some emodiments, a central and longitudinal axis (99) is connected to the central hinge (92) of the crossbar (91) and the arms (90) are maintained fixed relatively to the arms of the implant holder, so that by pushing on this axis (99) in the longitudinal direction, the central hinge (92) advances towards the implant while moving the crossbars (91) apart, which push, through their fixed hinges (93), the arms (90) of the distractor (9) thereby allowing the arms (51) of the implant holder (5) to be moved apart. The illustrative and non-limiting examples of FIGS. 17A, 17C, 17D and 17E represent the use of such a retractor on various embodiments of an implant holder of the type of the one of FIG. 7B. It will be noted that in various embodiments, the distractor (9) forms a shim holder, as for example illustrated in FIG. 17E, but in a general way, the shim holder (6) of various embodiments often also ensures a distraction function, such as for example represented in the examples of FIGS. 19B and 19C or 20A and 20B or as understood, from the cooperation between the spatulas (510) of the implant holder (5) with the guiding means (64) of the shim holder (6), for example with reference to FIGS. 12B and 14B. The illustrative and non-limiting examples of FIGS. 18A and 18B represent such an implant holder (5) which include distraction means (52, 520, 525) for moving the arms (51) apart each holding a body (2) of the implant, comprising a body (52) secured to one of the arms (51) and in which slides a bar (520) secured to the other arms (51). In some embodiments, a knurl or handle (525), for example knurled handle, may drive the bar (520) in translation by a rack mechanism as described in the embodiments above and/or lock the gap of both arms (51). In certain embodiments, alternatively (or optionally additionally) to the distractor (9) described above, the implant holder includes a means (54, 540) for pushing a shim holder (6), which forms a means for distraction of the arms (51) of the implant holder. In these embodiments, illustrative and non-limiting examples of which are illustrated in FIGS. 18A, 18B and 18C and also 19A, 19B, 19C and then 20A, 20B, 20C, 20D and 20E, the pushing means (54, 540) gives the possibility of pushing the shim holder (6) between the arms (51) so as to move them apart by means of the contact of the guiding means (64, 641) with the implant holder (5). In the examples of FIGS. 18A, 18B and 18C, the pushing means (54, 540) includes a knurl (54) which may be driven into rotation and provided with a notched axis driving the shim holder (6) through a rack mechanism, by means of a notched portion (654) of the arm (61) of the shim holder (6). Other mechanisms are possible for exerting the thrust, but the rack mechanism gives at least one mechanism having the possibility of finely handling the thrust. As illustrated in the examples of FIGS. 19A, 19C and then 20A and 20B, by pushing the shim holder (6) alone between the arms (51) of the implant holder, its guiding means (64, 641) move said arms (51) apart, for example by means of a spacer (641) at the end of the shim holder (6). Preferably, this moving apart is facilitated by the shape complementarity of the spacer (641) with the arms (51) of the implant holder, for example equipped with guiding spatulas (510) as detailed above. Once the gap has been obtained, it may be locked by means of a locking means (525) such as for example the knurl or handle (525) of the implant holder (5). The shim holder may then be provided with the shim (3) for inserting the latter between the plates (2), thus moved apart, as for the examples illustrated in FIGS. 20C, 20D and 20E.

In certain embodiments, the instrumentation aims at facilitating the implantation of an implant and notably the insertion of shims (3) between the plates (2). Illustrative and non-limiting examples of such embodiments are illustrated in FIGS. 21A, 21B, 22A, 22B, 23A, 23B, 24A, 24B and 25A. The implant holder, as for example visible in FIG. 22A, generally includes two arms (51) bearing the plate (2) of the implant, for example with adjustment means (511) as discussed above and for example with loaders (8) containing the anchors (1) as discussed above. In the example illustrated in FIG. 22B, distraction is obtained by the fact that the arms (51) are each secured to an upright (52) and these uprights are slideably mounted on a bar (520) displaced out of the plane of the arms (51). Between both uprights (52), a handle (525) is mounted on the bar and contains two threadings or tappings with reversed threads and each cooperating with a tapping or a threading respectively, corresponding to one of the uprights (52). Thus, by actuating the handle (525) in rotation, the moving away or the moving closer of the two uprights (52) is caused relatively to the other along the axis of the bar (520). In certain embodiments, the distraction means (52, 520, 525) are displaced outside the plane of the arms (51), as for example visible in FIG. 22B. This displacement allows the addition of a pistol mechanism (53) on at least one, but preferably on each, of the arms (51) of the implant holder, as for example visible in FIGS. 21A and 21B. Such pistols (53) are for example attached on the arms (51) via a base containing a locking latch (535) as for example illustrated in FIG. 22A. The pistol mechanism (53) may include a first fixed handle (530) and a second handle (531) pivotally mounted relatively to the first handle (530) about an axis (5310) perpendicular to the axis of this first handle (530). The second handle (531) in some embodiments extends beyond the axis (5310) with a rod provided with indentation intended to receive a lug of the shim holder (6), as for example visible in FIGS. 21A, 21B, 23B and 24B (or conversely a lug for cooperating with an indentation). In certain alternatives, elastic means (532) are provided between the first handle (530) and the second handle (531) for pushing back the latter relatively to the former in the absence of any force exerted on the latter. By actuating the pistols, i.e. by bringing the second handle (531) closer to the first handle (530), in some embodiments the implant holder (6) is pushed towards the implant. This mechanism may be used for facilitating the moving apart of the arms (51) on the one hand but also the insertion of the shim (3) between the plates (2), notably for overcoming the risk of difficult insertion due to the fact that a cantilever of the arms (51) may result in insufficient spacing of the plates (2) before insertion of the shim (3). In these illustrated examples, two pistol mechanisms are provided for improving the distribution of the thrust on the shim holder, but a single pistol mechanism is sometimes possible. In the case of some embodiments having two mechanisms, the actuation of the two second handles (531) may be achieved at the same time for pushing the shim holder (6), but this may allow better control of the insertion. Further, such pistol mechanisms may, in certain embodiments, also facilitate the impaction of the anchors (1), as for example illustrated in the illustrative and non-limiting examples of FIGS. 24B and 24A. Indeed, it is possible to provide that the impactor also includes a lug (753) for cooperating with the indentation of the pistol (53) (or vice versa). Generally it is preferred to retain an impacting end (73) for striking the impactor (7) since the penetration into the bone tissues may require this, but the pistol may facilitate the handling and limit the undesirable jumps of the impactor along the implant holder (5). It will be noted that it is possible, in various embodiments, to provide a dual impactor giving the possibility of pushing the anchors of both plates (2) at the same time, although it is generally preferred to gradually control the proper course of the operation and generally an impactor is therefore used for one vertebral structure at a time.

Various embodiments of the present application relate to a vertebral attachment device (1) for a vertebral implant, intended to be inserted, from the periphery of the rachis, through a passage (21) between the outside of a peripheral wall of the implant and one of the upper or lower surfaces of the implant in contact with a vertebral structure. In some embodiments, the device (1) includes a body comprising at least one curved, rigid and elongated plate (10) along a longitudinal axis extending between an anterior end and a posterior end, the plate (10) being configured so that its anterior end penetrates into a vertebral structure while its posterior end remains in the passage (21) of the implant. In some embodiments, a plate (10) is provided with at least one abutment (14) capable of receiving a locking means (4) with which the implant is equipped and an abutment portion of which juts out in said passage (21) when the locking means (4) is in a so-called closed position, locking the anchoring device in the implant, said abutment portion being set back out of the passage (21) when the locking means (4) is in an open position. In some embodiments, the passing of the locking means (4) from the open position to the closed position or vice versa may be achieved according to the various mechanisms described in the present application, whether they are automatic or by actuation. For example, an elastic portion of this locking means (4) allows its removal during the passage of the attachment device (1) and its elastic return when its abutment portion is found facing the abutment (14) of the attachment device (1) at the end of the deployment of the latter through the implant.

After comprehending the present disclosure, those skilled in the art will understand that the present disclosure allows embodiments in many other specific forms without departing from the scope of the claimed inventions. Therefore, the present embodiments should be considered as illustrations, but may be modified within the field defined by the scope of the appended claims, and the claims should not be limited to the details given above.

The invention claimed is:

1. A spinal segment replacement implant having a vertical axis and comprising:
   a first body and a second body;
   a second body contact face disposed on the first body;
   a first body contact face disposed on the second body;
   interfitting retainers disposed along opposing lateral edges of the first body contact face and opposing lateral edges of the second body contact face, the interfitting retainers being configured for sliding assembly of the first body with the second body along a sliding axis oblique to the vertical axis;
   a first recess disposed in the second body;
   a second recess disposed in the second body;
   a groove formed in an exterior surface of the second body; and
   an elongated lock configured to fit in the groove with a first end of the lock disposed in the first recess and a second end of the lock movably disposed in the second recess.

2. The implant of claim 1 in which the second end of the lock is tapered.

3. The implant of claim 1 in which the first body comprises a third recess that is oriented obliquely to the sliding axis and disposed proximal to one of the opposing lateral edges of the first body.

4. The implant of claim 3 in which the implant has:
   a disassembled configuration in which the first body and the second body are separated; and
   an assembled configuration in which the interfitting retainers of the first body and the interfitting retainers of the second body are engaged, with the lock disposed in the groove, the first end of the lock disposed in the first recess, and the second end of the lock disposed in the second recess and the third recess.

5. The implant of claim 1 in which the lock is U shaped.

6. The implant of claim 5 in which the first end of the lock is fixed in the first recess.

7. The implant of claim 6 in which the lock is flexible.

8. The implant of claim 7 in which the lock comprises radio opaque material.

9. A spinal segment replacement implant having a vertical axis and comprising:
   a first body and a second body;
   a second body contact face disposed on the first body;
   a first body contact face disposed on the second body;
   interfitting retainers disposed along opposing lateral edges of the first body contact face and opposing lateral edges of the second body contact face; the interfitting retainers being configured for sliding assembly of the first body with the second body along a sliding axis oblique to the vertical axis;
   a first recess disposed along a first one of the opposing lateral edges of the second body contact face and a second recess disposed along a second one of the opposing lateral edges of the second body contact face;

a groove formed in an exterior surface of the second body; and an elongated lock configured to fit in the groove with a first end of the lock movably disposed in the first recess and a second end of the lock movably disposed in the second recess.

10. The implant of claim 9 in which the first end of the lock and the second end of the lock are tapered.

11. The implant of claim 9 in which the first body comprises:

a third recess that is oriented obliquely to the sliding axis and disposed proximal to the first one of the opposing lateral edges of the first body; and a fourth recess that is oriented obliquely to the sliding axis and disposed proximal to the second one of the opposing lateral edges of the first body.

12. The implant of claim 11 in which the implant has:

a disassembled configuration in which the first body and the second body are separated; and an assembled configuration in which the interfitting retainers of the first body and the interfitting retainers of the second body are engaged, with the lock disposed in the groove, the first end of the lock disposed in the first recess and the third recess, and the second end of the lock disposed in the second recess and the fourth recess.

13. The implant of claim 12 in which the lock comprises a protrusion, the second body comprises a fifth recess disposed proximal to an anterior face of the second body, wherein in the assembled configuration, the protrusion is disposed in the fifth recess.

14. The implant of claim 9 in which lock is U shaped.

15. The implant of claim 14 in which the lock is flexible.

16. The implant of claim 9 in which the groove is disposed along the first one of opposing lateral sides of the second body and the second one of opposing lateral sides of the second body, the first recess and the second recess are disposed proximal to a posterior face of the second body, and the second body comprises a fifth recess disposed proximal to an anterior face of the second body.

17. A spinal segment replacement system comprising:

a spinal implant comprising:

a first body and a second body;

a second body contact face disposed on the first body;

a first body contact face disposed on the second body;

interfitting retainers disposed along opposing lateral edges of the first body contact face and opposing lateral edges of the second body contact face, the interfitting retainers being configured for sliding assembly of the first body with the second body along a sliding axis oblique to the vertical axis;

a first recess disposed in the second body;

a second recess disposed in the second body;

a groove formed in an exterior surface of the second body; and an elongated lock configured to fit in the groove with a first end of the lock disposed in the first recess and a second end of the lock movably disposed in the second recess; and a plurality of anchors, each anchor of the plurality of anchors comprising a penetration end configured for penetration of a surface of a spinal segment abutting the first body contact face or the second body contact face, a driving end configured for impacting the anchor into the surface of the spinal segment, a longitudinal axis extending between the penetration end and the driving end, and an anchor abutment disposed between the penetration end and the driving end and oriented angularly to the longitudinal axis.

18. The spinal segment replacement system of claim 17, wherein the first body and the second body include a plurality of anchor passages, wherein each anchor passage of the plurality of anchor passages extend from an access surface on the first body or the second body to the first body contact face or the second body contact face.

19. The spinal segment replacement system of claim 18, further comprising an insertion stop disposed along the driving end of each anchor of the plurality of anchors and configured to limit insertion of each anchor through a passage of the plurality of passages.

* * * * *